United States Patent
Sciotti et al.

(10) Patent No.: US 7,563,788 B2
(45) Date of Patent: Jul. 21, 2009

(54) SUBSTITUTED IMIDAZO[1,2-A]PYRIDINES AS ANTIBACTERIAL AGENTS

(75) Inventors: Richard John Sciotti, Saline, MI (US); Jeremy Tyson Starr, Ann Arbor, MI (US); Christopher Richardson, Remuera (NZ); Gordon William Rewcastle, Glendowie (NZ); Huifen Chen, Plymouth, MI (US); Brian Desmond Palmer, West Harbour (NZ); Hamish Scott Sutherland, Titirangi (NZ); Julie Ann Spicer, Pakuranga Heights (NZ)

(73) Assignee: Pfizer Inc., New York, NY (US)

( * ) Notice: Subject to any disclaimer, the term of this patent is extended or adjusted under 35 U.S.C. 154(b) by 87 days.

(21) Appl. No.: 10/598,841

(22) PCT Filed: Mar. 7, 2005

(86) PCT No.: PCT/IB2005/000596

§ 371 (c)(1),
(2), (4) Date: Sep. 13, 2006

(87) PCT Pub. No.: WO2005/089763

PCT Pub. Date: Sep. 29, 2005

(65) Prior Publication Data

US 2007/0191394 A1   Aug. 16, 2007

Related U.S. Application Data

(60) Provisional application No. 60/554,510, filed on Mar. 19, 2004, provisional application No. 60/630,777, filed on Nov. 23, 2004.

(51) Int. Cl.
| | |
|---|---|
| *C07D 413/06* | (2006.01) |
| *C07D 413/10* | (2006.01) |
| *C07D 471/04* | (2006.01) |
| *A61K 31/5355* | (2006.01) |
| *A61K 31/506* | (2006.01) |
| *A61K 31/497* | (2006.01) |
| *A61K 31/4355* | (2006.01) |
| *A61P 31/04* | (2006.01) |

(52) U.S. Cl. .......... 514/233.2; 514/274; 514/272; 514/253.02; 514/300; 544/127; 544/310; 546/121

(58) Field of Classification Search ............. 546/118; 514/303, 252.16, 233.2; 544/127, 362
See application file for complete search history.

(56) References Cited

U.S. PATENT DOCUMENTS

| | | |
|---|---|---|
| 4,096,264 A | 6/1978 | Bochis et al. |
| 4,105,767 A | 8/1978 | Bochis et al. |
| 4,250,174 A | 2/1981 | Bochis et al. |

OTHER PUBLICATIONS

Revankar et al.: "Synthesis and Antimicrobial Acrivity of Certain Imidazo '1,2-al pyrimidines" J. Med Chem. vol. 18, No. 12, 1975, pp. 1253-1255, XP002329731.
Akihiko Tanitame et al,: "Synthesis and antibacterial activity of a . . .", Bioorg. Med Chem Lett. 15(2005) 4299-4303.
Akihiko Tanitame et al: "Synthesis and antibacterial activity of novel and potent DNA gyrase inhibitors with asole ring", Biorg. Med. Chem, 12(2004) pp. 5515-5524.

*Primary Examiner*—James O Wilson
*Assistant Examiner*—Susanna Moore
(74) *Attorney, Agent, or Firm*—Gregg C. Benson; J. Michael Dixon

(57) ABSTRACT

Compounds of formula I and methods for their preparation are disclosed. Further disclosed are methods of making biologically active compounds of formula I as well as pharmaceutically acceptable compositions comprising compounds of formula I. Compounds of formula I as disclosed herein can be used in a variety of applications including use as antibacterial agents.

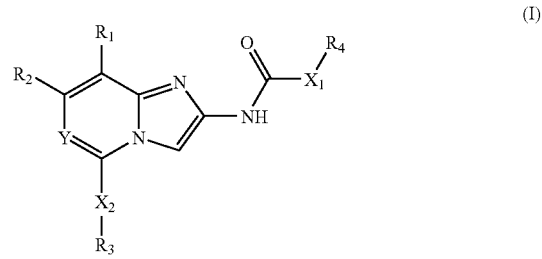

(I)

10 Claims, No Drawings

SUBSTITUTED IMIDAZO[1,2-A]PYRIDINES AS ANTIBACTERIAL AGENTS

CROSS REFERENCE TO RELATED APPLICATION

This application is a submission under 35 U.S.C. 371 of PCT/IB2005/000596 filed on Mar. 7, 2005, which claims priority to U.S. Provisional Application Nos. 60/554,510, filed on Mar. 19, 2004 and 60/630,777 filed on Nov. 23, 2004.

FIELD OF THE INVENTION

The invention relates to compounds which exhibit antibacterial activity, methods for their preparation, as well as pharmaceutically acceptable compositions comprising such compounds.

BACKGROUND OF THE INVENTION

Antibacterial resistance is a global clinical and public health problem that has emerged with alarming rapidity in recent years and undoubtedly will increase in the near future. Resistance is a problem in the community as well as in health care settings, where transmission of bacteria is greatly amplified. Because multiple drug resistance is a growing problem, physicians are now confronted with infections for which there is no effective therapy. The morbidity, mortality, and financial costs of such infections pose an increasing burden for health care systems worldwide. Strategies to address these issues emphasize enhanced surveillance of drug resistance, increased monitoring and improved usage of antimicrobial drugs, professional and public education, development of new drugs, and assessment of alternative therapeutic modalities.

As a result, alternative and improved agents are needed for the treatment of bacterial infections, particularly for the treatment of infections caused by resistant strains of bacteria, e.g., penicillin-resistant, methicillin-resistant, ciprofloxacin-resistant, and/or vancomycin-resistant strains.

SUMMARY OF THE INVENTION

These and other needs are met by the present invention, which is directed to a compound of formula I

I or a pharmaceutically acceptable salt thereof, wherein:
$X_1$ is $CH_2$, NH, or O;
$X_2$ is absent, or
is $(CH_2)_{x'}$, NH, O, , or , wherein "⌇" are points of attachment, or is a tether 2, 3 or 4 atoms in length, selected from $\sim CH_2-CH_2-N\sim$, $\sim CH_2-O\sim$,
                $|$
                $R$
$\sim CH_2-CH_2-O\sim$, $\sim O-CH_2-CH_2-N\sim$,
                                        $|$
                                        $R$
$\sim O-CH_2-CH_2-O\sim$,
$\sim N-CH_2-CH_2-N\sim$
   $|$              $|$
   $R$              $R$ wherein R is H or $(C_1-C_6)$alkyl, and
wherein "⌇" are points of attachment and x' is an integer selected from 1, 2, or 3;
Y is N, C—H, C—F, or C—OMe;
$R_1$ is H or halo;
$R_2$ is $(C_3-C_6)$cycloalkyl,
$(CH_2)_x$-aryl,
$(CH_2)_x$-heterocyclo, or
$(CH_2)_x$-heteroaryl,
wherein x is 0, 1, or 2;
$R_3$ is H,
$(C_1-C_6)$alkyl,
$(C_3-C_6)$cycloalkyl,
aryl,
heterocyclo,
heteroaryl,
$C(O)NR_aR_b$,
$C(O)R_a$,
$CO_2R_a$,
$C(O)C(O)NR_aR_b$,
$NO_2$,
$SO_2R_a$,
$SO_2NR_aR_b$,
$C(R_c)=NOR_a$,
$C(R_c)=NR_a$, wherein "⌇" indicates the point of attachment, wherein "⌇" indicates the point of attachment,
and wherein
$R_a$ is H,
$(C_1-C_6)$alkyl, ($C_3$-$C_6$)cycloalkyl,
($CH_2$)$_y$-aryl,
($CH_2$)$_y$-heterocyclo, or
($CH_2$)$_y$-heteroaryl,
wherein y is 0, 1, or 2;
$R_b$ is H,
($C_1$-$C_6$)alkyl,
($C_3$-$C_6$)cycloalkyl,
aryl,
heterocyclo, or
heteroaryl;
$R_c$ is H,
($C_1$-$C_6$)alkyl,
($C_3$-$C_6$)cycloalkyl,
aryl,
heterocyclo, or
heteroaryl; and
$R_4$ is ($C_1$-$C_6$)alkyl, ($C_1$-$C_6$)alkyl-O—($C_1$-$C_6$)alkyl, cyclopropyl, $CH_2$-cyclopropyl, or cyclobutyl.

The compounds of Formula I exhibit antibacterial activity. They may be used to treat bacterial infections in mammals, especially humans. The compounds may also be used for veterinary applications, such as treating infections in livestock and companion animals.

The compounds exhibit activity against selected strains of Gram-positive bacteria, Gram-negative bacteria, and anaerobic bacteria. They may be used to treat common infections such as otitis media, sinusitis, pharyngitis/tonsilitis, bronchitis, urinary tract infections, skin infections, pneumonia, septicemia, etc. In order to simplify administration, the compounds will typically be admixed with at least one excipient and formulated into pharmaceutical dosage forms. Examples of such dosage forms include tablets, capsules, solutions/suspensions for injection, and solutions/suspensions for oral ingestion.

Examples of Compounds encompassed by Formula I, in which Y is C—H include:
a) 3-[2-(3-Ethyl-ureido)-7-pyridin-3-yl-imidazo[1,2-a]pyridin-5-yl]-[1,2,4]oxadiazole-5-carboxylic acid methylamide;
b) 1-{5-[5-(2-Dimethylamino-ethyl)-[1,2,4]oxadiazol-3-yl]-7-pyridin-3-yl-imidazo[1,2-a]pyridin-2-yl}-3-ethyl-urea;
c) 1-Ethyl-3-[5-(5-methoxy-[1,2,4]oxadiazol-3-yl)-7-pyridin-3-yl-imidazo[1,2-a]pyridin-2-yl]-urea;
d) 1-Ethyl-3-[5-(3-methoxy-[1,2,4]oxadiazol-5-yl)-7-pyridin-3-yl-imidazo[1,2-a]pyridin-2-yl]-urea;
e) 1-Ethyl-3-[5-(3-methylamino-[1,2,4]oxadiazol-5-yl)-7-pyridin-3-yl-imidazo[1,2-a]pyridin-2-yl]-urea;
f) 1-Ethyl-3-{5-[5-(2-hydroxy-ethyl)-[1,3,4]oxadiazol-2-yl]-7-pyridin-3-yl-imidazo[1,2-a]pyridin-2-yl}-urea;
g) 1-Ethyl-3-[5-(5-methyl-[1,3,4]oxadiazol-2-yl)-7-pyridin-3-yl-imidazo[1,2-a]pyridin-2-yl]-urea;
h) 1-{5-[5-(2-Dimethylamino-ethyl)-[1,3,4]oxadiazol-2-yl]-7-pyridin-3-yl-imidazo[1,2-a]pyridin-2-yl}-3-ethyl-urea;
i) 1-Ethyl-3-[5-(5-methyl-[1,2,4]oxadiazol-3-yl)-7-pyridin-3-yl-imidazo[1,2-a]pyridin-2-yl]-urea;
j) 1-Ethyl-3-[5-(5-methyl-[1,3,4]thiadiazol-2-yl)-7-pyridin-3-yl-imidazo[1,2-a]pyridin-2-yl]-urea;
k) 1-Ethyl-3-{5-[5-(2-hydroxy-ethyl)-[1,3,4]thiadiazol-2-yl]-7-pyridin-3-yl-imidazo[1,2-a]pyridin-2-yl}-urea;
l) 1-{5-[5-(2-Dimethylamino-ethyl)-[1,3,4]thiadiazol-2-yl]-7-pyridin-3-yl-imidazo[1,2-a]pyridin-2-yl}-3-ethyl-urea;
m) 2-(3-Ethyl-ureido)-7-pyridin-3-yl-imidazo[1,2-a]pyridine-5-carboxylic acid methyl ester;
n) 2-(3-Ethyl-ureido)-7-pyridin-3-yl-imidazo[1,2-a]pyridine-5-carboxylic acid ethylamide;
o) 1-[5-(2-Dimethylamino-acetyl)-7-pyridin-3-yl-imidazo[1,2-a]pyridin-2-yl]-3-ethyl-urea;
p) 1-Ethyl-3-(7-pyridin-3-yl-5-trifluoromethoxymethyl-imidazo[1,2-a]pyridin-2-yl)-urea;
q) 1-Ethyl-3-(5-propionyl-7-pyridin-3-yl-imidazo[1,2-a]pyridin-2-yl)-urea;
r) 1-Ethyl-3-[5-(1-methylimino-propyl)-7-pyridin-3-yl-imidazo[1,2-a]pyridin-2-yl]-urea;
s) 1-(5-Cyclopropanecarbonyl-7-pyridin-3-yl-imidazo[1,2-a]pyridin-2-yl)-3-ethyl-urea;
t) 1-[5-(Cyclopropyl-methoxyimino-methyl)-7-pyridin-3-yl-imidazo[1,2-a]pyridin-2-yl]-3-methyl-urea;
u) 1-[5-Cyclopropanecarbonyl-7-(2-oxo-1,2-dihydro-pyridin-4-yl)-imidazo[1,2-a]pyridin-2-yl]-3-ethyl-urea;
v) 1-Ethyl-3-[7-(2-oxo-1,2-dihydro-pyridin-4-yl)-5-propionyl-imidazo[1,2-a]pyridin-2-yl]-urea;
w) 1-Ethyl-3-[5-(2-methanesulfonyl-ethyl)-7-pyridin-3-yl-imidazo[1,2-a]pyridin-2-yl]-urea;
x) 1-Ethyl-3-[5-(5-methyl-4H-[1,2,4]triazol-3-yl)-7-pyridin-3-yl-imidazo[1,2-a]pyridin-2-yl]-urea;
y) 1-Ethyl-3-[5-(1-methyl-1H-pyrazol-4-yl)-7-pyridin-3-yl-imidazo[1,2-a]pyridin-2-yl]-urea;
z) 1-[5-(2-Dimethylamino-ethoxy)-7-pyridin-3-yl-imidazo[1,2-a]pyridin-2-yl]-3-ethyl-urea;
aa) 1-Ethyl-3-[7-pyridin-3-yl-5-(2-[1,2,4]triazol-1-yl-ethoxy)-imidazo[1,2-a]pyridin-2-yl]-urea;
bb) 1-{5-[4-(2-Dimethylamino-ethyl)-thiazol-2-yl]-7-pyridin-3-yl-imidazo[1,2-a]pyridin-2-yl}-3-ethyl-urea;
cc) N-Methyl-2-[2-(3-methyl-ureido)-7-pyridin-3-yl-imidazo[1,2-a]pyridin-5-yloxy]-acetamide;
dd) 1-Ethyl-3-[5-(6-hydroxy-pyridin-3-yl)-7-pyridin-3-yl-imidazo[1,2-a]pyridin-2-yl]-urea;
ee) 1-{5-[4-(2-Dimethylamino-ethyl)-oxazol-2-yl]-7-pyridin-3-yl-imidazo[1,2-a]pyridin-2-yl}-3-ethyl-urea;
ff) 1-[5-(2-Dimethylamino-ethoxy)-7-pyridin-3-yl-imidazo[1,2-a]pyridin-2-yl]-3-ethyl-urea;
gg) 1-Ethyl-3-[5-(2-pyrazol-1-yl-ethyl)-7-pyridin-3-yl-imidazo[1,2-a]pyridin-2-yl]-urea;
hh) 2-[2-(3-Ethyl-ureido)-7-pyridin-3-yl-imidazo[1,2-a]pyridin-5-yl]-thiazole-4-carboxylic acid amide;
ii) 1-Ethyl-3-[5-(2-oxo-2-pyridin-2-yl-ethyl)-7-pyridin-3-yl-imidazo[1,2-a]pyridin-2-yl]-urea;
jj) 1-Ethyl-3-[5-(2-oxazol-2-yl-ethyl)-7-pyridin-3-yl-imidazo[1,2-a]pyridin-2-yl]-urea;
kk) 1-Ethyl-3-[5-(2-methylamino-pyrimidin-5-yl)-7-pyridin-3-yl-imidazo[1,2-a]pyridin-2-yl]-urea;
ll) 1-(5-Cyclopropyl-7-pyridin-3-yl-imidazo[1,2-a]pyridin-2-yl)-3-ethyl-urea; and
mm) N-{2-[2-(3-Ethyl-ureido)-7-pyridin-3-yl-imidazo[1,2-a]pyridin-5-yl]-ethyl}-acetamide.

Examples of compounds encompassed by Formula I, in which Y is N include:
a) 3-[2-(3-Ethyl-ureido)-7-pyridin-3-yl-imidazo[1,2-c]pyrimidin-5-yl]-[1,2,4]oxadiazole-5-carboxylic acid methylamide
b) 1-{5-[5-(2-Dimethylamino-ethyl)-[1,2,4]oxadiazol-3-yl]-7-pyridin-3-yl-imidazo[1,2-c]pyrimidin-2-yl}-3-ethyl-urea;
c) 1-Ethyl-3-[5-(5-methoxy-[1,2,4]oxadiazol-3-yl)-7-pyridin-3-yl-imidazo[1,2-c]pyrimidin-2-yl]-urea;
d) 1-Ethyl-3-[5-(3-methoxy-[1,2,4]oxadiazol-5-yl)-7-pyridin-3-yl-imidazo[1,2-c]pyrimidin-2-yl]-urea;
e) 1-Ethyl-3-[5-(3-methylamino-[1,2,4]oxadiazol-5-yl)-7-pyridin-3-yl-imidazo[1,2-c]pyrimidin-2-yl]-urea;
f) 1-Ethyl-3-{5-[5-(2-hydroxy-ethyl)-[1,3,4]oxadiazol-2-yl]-7-pyridin-3-yl-imidazo[1,2-c]pyrimidin-2-yl}-urea;

g) 1-Ethyl-3-[5-(5-methyl-[1,3,4]oxadiazol-2-yl)-7-pyridin-3-yl-imidazo[1,2-c]pyrimidin-2-yl]-urea;
h) 1-{5-[5-(2-Dimethylamino-ethyl)-[1,3,4]oxadiazol-2-yl]-7-pyridin-3-yl-imidazo[1,2-c]pyrimidin-2-yl}-3-ethyl-urea;
i) 1-Ethyl-3-[5-(5-methyl-[1,2,4]oxadiazol-3-yl)-7-pyridin-3-yl-imidazo[1,2-c]pyrimidin-2-yl]-urea;
j) 1-Ethyl-3-[5-(5-methyl-[1,3,4]thiadiazol-2-yl)-7-pyridin-3-yl-imidazo[1,2-c]pyrimidin-2-yl]-urea;
k) 1-Ethyl-3-{5-[5-(2-hydroxy-ethyl)-[1,3,4]thiadiazol-2-yl]-7-pyridin-3-yl-imidazo[1,2-c]pyrimidin-2-yl}-urea;
m) 1-{5-[5-(2-Dimethylamino-ethyl)-[1,3,4]thiadiazol-2-yl]-7-pyridin-3-yl-imidazo[1,2-c]pyrimidin-2-yl}-3-ethyl-urea;
n) 2-(3-Ethyl-ureido)-7-pyridin-3-yl-imidazo[1,2-c]pyrimidine-5-carboxylic acid methyl ester;
o) 2-(3-Ethyl-ureido)-7-pyridin-3-yl-imidazo[1,2-c]pyrimidine-5-carboxylic acid ethylamide;
p) 1-[5-(2-Dimethylamino-acetyl)-7-pyridin-3-yl-imidazo[1,2-c]pyrimidin-2-yl]-3-ethyl-urea;
q) 1-Ethyl-3-(7-pyridin-3-yl-5-trifluoromethoxymethyl-imidazo[1,2-c]pyrimidin-2-yl)-urea;
r) 1-Ethyl-3-(5-propionyl-7-pyridin-3-yl-imidazo[1,2-c]pyrimidin-2-yl)-urea;
s) 1-Ethyl-3-[5-(1-methoxyimino-propyl)-7-pyridin-3-yl-imidazo[1,2-c]pyrimidin-2-yl]-urea;
t) 1-(5-Cyclopropanecarbonyl-7-pyridin-3-yl-imidazo[1,2-c]pyrimidin-2-yl)-3-ethyl-urea;
u) 1-[5-(Cyclopropyl-methoxyimino-methyl)-7-pyridin-3-yl-imidazo[1,2-c]pyrimidin-2-yl]-3-ethyl-urea;
v) 1-[5-Cyclopropanecarbonyl-7-(2-oxo-1,2-dihydro-pyridin-4-yl)-imidazo[1,2-c]pyrimidin-2-yl]-3-ethyl-urea;
x) 1-Ethyl-3-[7-(2-oxo-1,2-dihydro-pyridin-4-yl)-5-propionyl-imidazo[1,2-c]pyrimidin-2-yl]-urea;
y) 1-Ethyl-3-[5-(2-methanesulfonyl-ethyl)-7-pyridin-3-yl-imidazo[1,2-c]pyrimidin-2-yl]-urea;
z) 1-Ethyl-3-[5-(5-methyl-4H-[1,2,4]triazol-3-yl)-7-pyridin-3-yl-imidazo[1,2-c]pyrimidin-2-yl]-urea;
aa) 1-Ethyl-3-[5-(1-methyl-1H-pyrazol-4-yl)-7-pyridin-3-yl-imidazo[1,2-c]pyrimidin-2-yl]-urea;
bb) 1-[5-(2-Dimethylamino-ethoxy)-7-pyridin-3-yl-imidazo[1,2-c]pyrimidin-2-yl]-3-ethyl-urea;
cc) 1-Ethyl-3-[7-pyridin-3-yl-5-(2-[1,2,4]triazol-1-yl-ethoxy)-imidazo[1,2-c]pyrimidin-2-yl]-urea;
dd) 1-{5-[4-(2-Dimethylamino-ethyl)-thiazol-2-yl]-7-pyridin-3-yl-imidazo[1,2-c]pyrimidin-2-yl}-3-ethyl-urea;
ee) N-Methyl-2-[2-(3-methyl-ureido)-7-pyridin-3-yl-imidazo[1,2-c]pyrimidin-5-yloxy]-acetamide;
ff) 1-Ethyl-3-[5-(6-hydroxy-pyridin-3-yl)-7-pyridin-3-yl-imidazo[1,2-c]pyrimidin-2-yl]-urea;
gg) 1-{5-[4-(2-Dimethylamino-ethyl)-oxazol-2-yl]-7-pyridin-3-yl-imidazo[1,2-c]pyrimidin-2-yl}-3-ethyl-urea;
hh) 1-[5-(2-Dimethylamino-ethoxy)-7-pyridin-3-yl-imidazo[1,2-c]pyrimidin-2-yl]-3-ethyl-urea;
ii) 1-Ethyl-3-[5-(2-pyrazol-1-yl-ethyl)-7-pyridin-3-yl-imidazo[1,2-c]pyrimidin-2-yl]-urea;
jj) 2-[2-(3-Ethyl-ureido)-7-pyridin-3-yl-imidazo[1,2-c]pyrimidin-5-yl]-thiazole-4-carboxylic acid amide;
kk) 1-Ethyl-3-[5-(2-oxo-2-pyridin-2-yl-ethyl)-7-pyridin-3-yl-imidazo[1,2-c]pyrimidin-2-yl]-urea;
ll) 1-Ethyl-3-[5-(2-oxazol-2-yl-ethyl)-7-pyridin-3-yl-imidazo[1,2-c]pyrimidin-2-yl]-urea;
mm) 1-Ethyl-3-[5-(2-methylamino-pyrimidin-5-yl)-7-pyridin-3-yl-imidazo[1,2-c]pyrimidin-2-yl]-urea;
nn) 1-(5-Cyclopropyl-7-pyridin-3-yl-imidazo[1,2-c]pyrimidin-2-yl)-3-ethyl-urea;
oo) N-{2-[2-(3-Ethyl-ureido)-7-pyridin-3-yl-imidazo[1,2-c]pyrimidin-5-yl]-ethyl}-acetamide; and
op) 1-[7-(2-Amino-pyridin-4-yl)-imidazo[1,2-a]pyridin-2-yl]-3-ethyl-urea.

A more specific embodiment of the invention is directed to those compounds of Formula I in which:
a) Y is CH and $R_1$, $R_2$, $R_3$, $R_4$, $X_1$, and $X_2$ are as above;
b) Y is N and $R_1$, $R_2$, $R_3$, $R_4$, $X_1$, and $X_2$ are as above;
c) Y is CH, $X_2$ is absent, and $X_1$ is NH;
d) Y is N, $X_2$ is absent, and $X_1$ is NH;
e) Y is N, $R_2$ is heteroaryl, $X_2$ is absent, and $X_1$ is NH;
f) Y is CH, $R_2$ is heteroaryl, $X_2$ is absent, and $X_1$ is NH;
g) Y is N, $R_2$ and $R_3$ are each heteroaryl, $X_2$ is absent, and $X_1$ is NH;
h) Y is CH, $R_2$ and $R_3$ are each heteroaryl, $X_2$ is absent, and $X_1$ is NH;
i) Y is N, $R_2$ is heteroaryl, $X_2$ is absent, $R_3$ is represented by $CO_2R_a$, $COR_a$ or $C(O)NR_aR_b$ and $X_1$ is NH;
j) Y is CH, $R_2$ is heteroaryl, $X_2$ is absent, $R_3$ is represented by $CO_2R_a$, $COR_a$ or $C(O)NR_aR_b$ and $X_1$ is NH;
k) Y is N, $R_2$ is heteroaryl, $X_2$ is absent, $R_3$ is H, and $X_1$ is NH;
l) Y is CH, $R_2$ is heteroaryl, $X_2$ is absent, $R_3$ is H, and $X_1$ is NH
m) Y is N, $R_2$ is heteroaryl, $X_2$ is absent, $R_3$ is H, $X_1$ is NH and $R_4$ is ethyl, isopropyl, trifluoroethyl, or cyclopropyl;
n) Y is CH, $R_2$ is heteroaryl, $X_2$ is absent, $R_3$ is H, $X_1$ is NH and, and $R_4$ is ethyl, cyclobutyl, isopropyl or trifluoroethyl; or;
o) Y is N, $R_2$ is pyridinyl or pyrimidinyl, $X_2$ is absent, $R_3$ is H, $X_1$ is NH and $R_4$ is ethyl, isopropyl, trifluoroethyl, or cyclopropyl.
p) Y is CH, $R_2$ is pyridinyl or pyrimidinyl, $X_2$ is absent, $R_3$ is H, $X_1$ is NH and $R_4$ is ethyl, isopropyl, trifluoroethyl, or cyclopropyl.

Additional compounds encompassed by Formula I include:

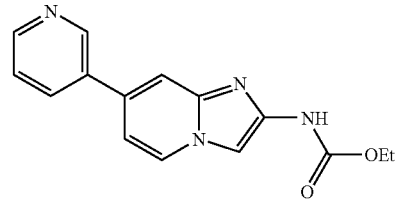

(7-Pyridin-3-yl-imidazo[1,2-a]pyridin-2-yl)-carbamic acid ethyl ester;

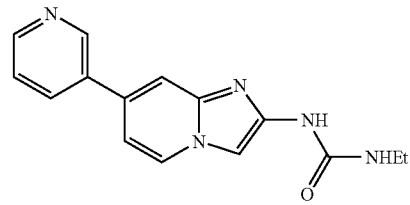

1-Ethyl-3-(7-pyridin-3-yl-imidazo[1,2-a]pyridin-2-yl)-urea;

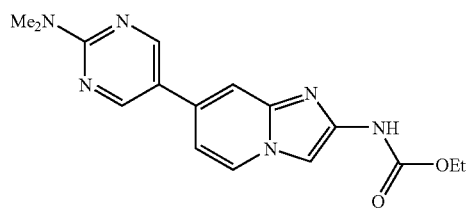

[7-(2-Dimethylamino-pyrimidin-5-yl)-imidazo[1,2-a]pyridin-2-yl]-carbamic acid ethyl ester;

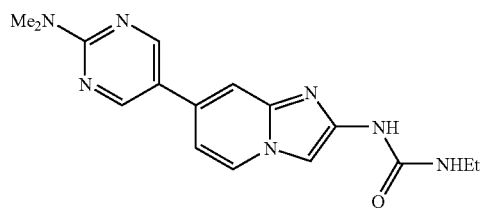

1-[7-(2-Dimethylamino-pyrimidin-5-yl)-imidazo[1,2-a]pyridin-2-yl]-3-ethyl-urea;

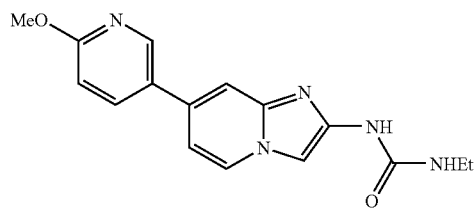

1-Ethyl-3-[7-(6-methoxy-pyridin-3-yl)-imidazo[1,2-a]pyridin-2-yl]-urea;

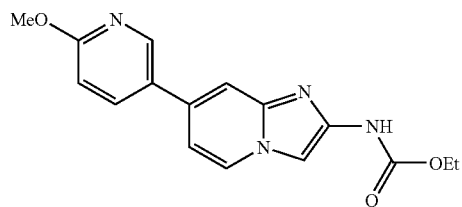

[7-(6-Methoxy-pyridin-3-yl)-imidazo[1,2-a]pyridin-2-yl]-carbamic acid ethyl ester; or

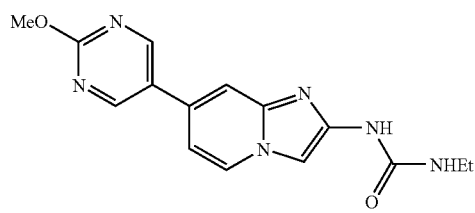

1-Ethyl-3-[7-(2-methoxy-pyrimidin-5-yl)-imidazo[1,2-a]pyridin-2-yl]-urea.

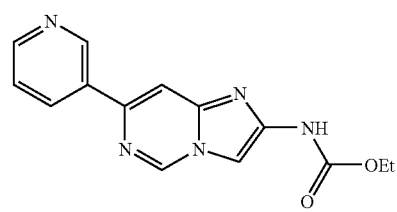

(7-Pyridin-3-yl-imidazo[1,2-c]pyrimidin-2-yl)-carbamic acid ethyl ester;

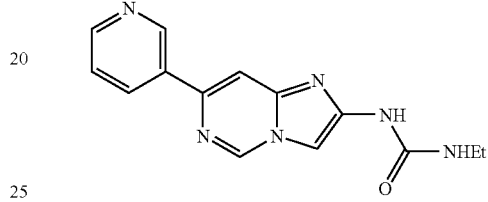

1-Ethyl-3-(7-pyridin-3-yl-imidazo[1,2-c]pyrimidin-2-yl)-urea;

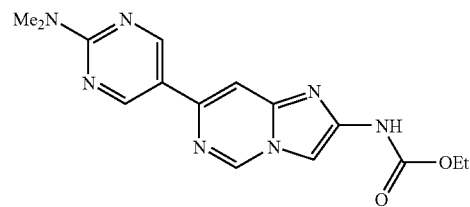

[7-(2-Dimethylamino-pyrimidin-5-yl)-imidazo[1,2-c]pyrimidin-2-yl]-carbamic acid ethyl ester;

1-[7-(2-Dimethylamino-pyrimidin-5-yl)-imidazo[1,2-c]pyrimidin-2-yl]-3-ethyl-urea;

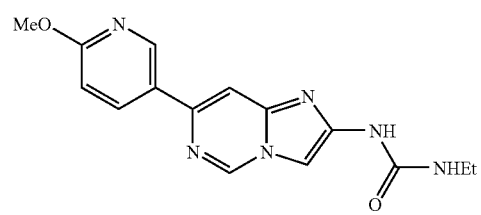

1-Ethyl-3-[7-(6-methoxy-pyridin-3-yl)-imidazo[1,2-c]pyrimidin-2-yl]-urea;

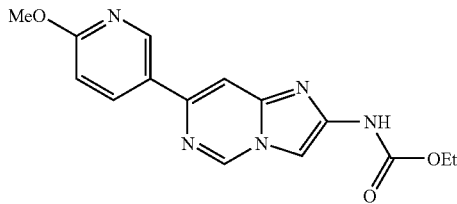

[7-(6-Methoxy-pyridin-3-yl)-imidazo[1,2-c]pyrimidin-2-yl]-carbamic acid ethyl ester; or

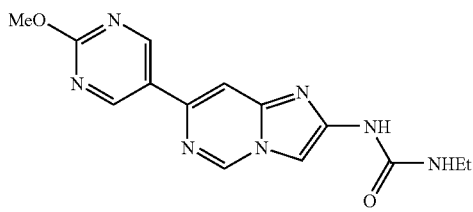

1-Ethyl-3-[7-(2-methoxy-pyrimidin-5-yl)-imidazo[1,2-c]pyrimidin-2-yl]-urea.

DETAILED DESCRIPTION OF THE INVENTION

Reference will now be made in detail to compositions or embodiments and methods of the invention.

The term "($C_1$-$C_6$)alkyl" as used herein refers to a straight or branched hydrocarbon from 1 to 6 carbon atoms and includes, for example, methyl, ethyl, n-propyl, isopropyl, n-butyl, sec-butyl, isobutyl, tert-butyl, n-pentyl, n-hexyl, and the like. The ($C_1$-$C_6$)alkyl group optionally can be substituted with one or more of the substituents selected from cycloalkyl, heterocycloalkyl, aryl, heteroaryl, ($C_1$-$C_6$)alkoxy, ($C_1$-$C_6$)thioalkoxy, halo, oxo, thio, cyano, haloalkyl, haloalkoxy, —OH, —$NO_2$, —$NH_2$, aminoalkyl, —$CO_2H$, —$CO_2$($C_1$-$C_6$)alkyl, —CO($C_1$-$C_6$)alkyl, —C(O)N($C_1$-$C_6$)alkyl or

The term "($C_1$-$C_3$)alkyl" as used herein refers to a straight or branched hydrocarbon of from 1 to 3 carbon atoms and includes, for example, methyl, ethyl, n-propyl, isopropyl, and the like. The ($C_1$-$C_3$)alkyl group optionally can be substituted with one or more of the substituents selected from cycloalkyl, heterocycloalkyl, aryl, heteroaryl, ($C_1$-$C_6$)alkoxy, ($C_1$-$C_6$)thioalkoxy, halo, oxo, thio, —OH, cyano, haloalkyl, haloalkoxy, —$NO_2$, —$NH_2$, aminoalkyl, —$CO_2H$, —$CO_2$($C_1$-$C_6$)alkyl, —CO($C_1$-$C_6$)alkyl, —C(O)N($C_1$-$C_6$)alkyl or

The term "haloalkyl" refers to a branched or straight chained alkyl group containing from 1 to 6 carbon atoms, in which at least one hydrogen atom is replaced with a halogen (i.e. $C_1$-$C_6$ haloalkyl). Examples of suitable haloalkyl's include chloromethyl, difluoromethyl, trifluoromethyl, 1-fluoro-2-chloro-ethyl, 5-fluoro-hexyl, 3-difluoro-isopropyl, 3-chloro-isobutyl, etc.

The term "haloalkoxy" refers to refers to a branched or straight chained alkoxy group containing from 1 to 6 carbon atoms, in which at least one hydrogen atom is replaced with a halogen (i.e. $C_1$-$C_6$ haloalkoxy). Examples of suitable haloalkoxy's include chloromethoxy, difluoromethoxy, trifluoromethoxy, 1-fluoro-2-chloro-ethoxy, 5-fluoro-hexoxy, 3-difluoro-isopropoxy, 3-chloro-isobutoxy, etc.

The term "$C_1$-$C_6$ alkoxy" refers to a straight or branched chain alkoxy group containing from 1 to 6 carbon atoms, such as methoxy, ethoxy, n-propoxy, isopropoxy, n-butoxy, isobutoxy, pentoxy, etc.

The term "$C_1$-$C_6$ thioalkoxy" refers to a straight or branched chain thioalkoxy group containing from 1 to 6 carbon atoms, such as thiomethoxy, thioethoxy, n-thiopropoxy, isothiopropoxy, etc.

The term "amino" refers to —$NH_2$.

The term "aminoalkyl" refers to an amino moiety substituted with one or two $C_1$-$C_6$ alkyl groups. These alkyl groups may be the same or different. Examples of such aminoalkyl groups include aminomethyl, dimethylamino, aminomethylethyl, aminomethylpropyl, etc.

The term "($C_3$-$C_6$)cycloalkyl" means a hydrocarbon ring containing from 3 to 6 carbon atoms, for example, cyclopropyl, cyclobutyl, cyclopentyl, or cyclohexyl. Where possible, the cycloalkyl group may contain double bonds, for example, 3-cyclohexen-1-yl. The cycloalkyl ring may be unsubstituted or optionally may be substituted by one or more substituents selected from ($C_1$-$C_6$)alkyl, ($C_1$-$C_6$)alkoxy, ($C_1$-$C_6$)thioalkoxy, hydroxy, thiol, halo, formyl, carboxyl, amino, aminoalkyl, —$CO_2$($C_1$-$C_6$)alkyl, —CO($C_1$-$C_6$)alkyl, —C(O)N($C_1$-$C_6$)alkyl, aryl, heteroaryl, wherein alkyl, aryl, and heteroaryl are as defined herein, or as indicated above for alkyl. Examples of substituted cycloalkyl groups include fluorocyclopropyl. Any reference in this application to a cycloalkyl group should be construed as referring to a "($C_3$-$C_6$)cycloalkyl The term "halo" includes chlorine, fluorine, bromine, and iodine.

The term "aryl" means a cyclic or polycyclic aromatic ring having from 5 to 12 carbon atoms, and may be unsubstituted or optionally may be substituted with one or more of the substituent groups recited above for alkyl groups. Examples include, but are not limited to phenyl, 2-chlorophenyl, 3-chlorophenyl, 4-chlorophenyl, 2-methylphenyl, 3-methylphenyl, 4-methylphenyl, 2-methoxyphenyl, 3-methoxyphenyl, 4-methoxyphenyl, 2-chloro-3-methylphenyl, 2-chloro-4-methylphenyl, 2-chloro-5-methylphenyl, 3-chloro-2-methylphenyl, 3-chloro-4-methylphenyl, 4-chloro-2-methylphenyl, 4-chloro-3-methylphenyl, 5-chloro-2-methylphenyl, 2,3-dichlorophenyl, 2,5-dichlorophenyl, 3,4-dichlorophenyl, 2,3-dimethylphenyl, 3,4-dimethylphenyl, naphthyl, 4-thionaphthyl, tetralinyl, benzonaphthenyl, and 4'-bromobiphenyl.

The term "heteroaryl" means an aromatic cyclic or polycyclic ring system having from 1 to 4 heteroatoms selected from N, O, and S, and may be unsubstituted or optionally may be substituted with one or more of the substituent groups recited above for alkyl groups. Typical heteroaryl groups include 1,2,4-oxadiazolyl, 1,3,4-oxadiazolyl, 1,2,4-thiadiazolyl, 1,3,4-thiadiazolyl, 2- or 3-thienyl, 2- or 3-furanyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridinyl, 3-, 4-, or 5-pyridazinyl, 2-pyrazinyl, 2-, 4-, or 5-pyrimidinyl, 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-, benzoxazolyl, 2-, 4-, 5-, 6-, or 7-benzimidazolyl, 2-, 4-, 5-, 6-, or 7-benzothiazolyl. The heteroaryl groups may be unsubstituted or substituted by 1 to 3 substituents (if chemically permissible) selected from those described above for alkyl, for example, cyanothienyl and formylpyrrolyl. Preferred aromatic fused heterocyclic rings of from 8 to 10 atoms include but are not limited to 2-, 3-, 4-, 5-, 6-, 7-, or 8-quinolinyl, 1-, 3-, 4-, 5-, 6-, 7-, or 8-isoquinolinyl-, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl. Heteroaryl also includes 2- and 3-aminomethylfuran, 2- and 3-aminomethylthiophene and the like.

The terms "heterocyclic, heterocycloalkyl and heterocyclo" are synonyms and each means a saturated or unsaturated (but not aromatic) monocyclic, fused, bridged, or spiro bicyclic heterocyclic ring systems and may be unsubstituted or optionally may be substituted with one or more of the substituent groups recited above for alkyl groups. Monocyclic heterocyclic rings contain from about 3 to 12 ring atoms, with from 1 to 5 heteroatoms selected from N, O, and S, and preferably from 3 to 7 member atoms, in the ring. Bicyclic heterocyclics contain from about 5 to about 17 ring atoms, preferably from 5 to 12 ring atoms. Bicyclic heterocyclic rings may be fused, spiro, or bridged ring systems. Examples of heterocyclic groups include cyclic ethers (oxiranes) such as ethyleneoxide, tetrahydrofuran, dioxane, and substituted cyclic ethers, wherein the substituents are those described above for the alkyl and cycloalkyl groups. Typical substituted cyclic ethers include propyleneoxide, phenyloxirane (styrene oxide), cis-2-butene-oxide (2,3-dimethyloxirane), 3-chlorotetrahydrofuran, 2,6-dimethyl-1,4-dioxane, and the like. Heterocycles containing nitrogen are groups such as pyrrolidine, piperidine, piperazine, tetrahydrotriazine, tetrahydropyrazole, and substituted groups such as 3-aminopyrrolidine, 4-methylpiperazin-1-yl, and the like. Typical sulfur containing heterocycles include tetrahydrothiophene, dihydro-1,3-dithiol-2-yl, and hexahydrothiophen-4-yl and substituted groups such as aminomethyl thiophene. Other commonly employed heterocycles include dihydro-oxathiol-4-yl, dihydro-1H-isoindole, tetrahydro-oxazolyl, tetrahydro-oxadiazolyl, tetrahydrodioxazolyl, tetrahydrooxathiazolyl, hexahydrotriazinyl, tetrahydrooxazinyl, morpholinyl, thiomorpholinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or $SO_2$ groups are also included. Examples include the sulfoxide and sulfone forms of tetrahydrothiophene.

$R_2$ and $R_3$ may each be represented by an aryl or heteroaryl moiety. For any compound substituted at either position with such a moiety, it is relevant to point that these aryl and heteroaryl's may be substituted. Permissible substituents include other heteroaryl, aryl, arylalkyl, heteroaryl alkyl, aryl alkoxy, heteroaryl alkoxy, aryl thioalkoxy, and heteroaryl thioalkoxy.

When a bond is represented by a symbol such as ----- this is meant to represent that the bond may be absent or present provided that the resultant compound is stable and of satisfactory valency.

When a bond is represented by a line such as "⌇" this is meant to represent that the bond is the point of attachment between two molecular subunits.

The term "patient" and "subject" are synonyms and mean all mammals, including humans. Other examples of patients include cows, dogs, cats, goats, sheep, pigs, and rabbits.

A "therapeutically effective amount" is an amount of a compound of the present invention that, when administered to a patient, provides the desired effect; i.e., lessening in the severity of the symptoms associated with a bacterial infection.

It will be appreciated by those skilled in the art that compounds of the invention having one or more chiral centers may exist in and be isolated in optically active and racemic forms. Some compounds may exhibit polymorphism. It is to be understood that the present invention encompasses any racemic, optically-active, polymorphic, geometric, or stereoisomeric form, or mixtures thereof, of a compound of the invention, which possess the useful properties described herein, it being well known in the art how to prepare such forms (for example, by resolution of the racemic form by recrystallization techniques, by synthesis from optically-active starting materials, by chiral synthesis, or by chromatographic separation using a chiral stationary phase).

Certain compounds of Formula I are also useful as intermediates for preparing other compounds of Formula I.

Some of the compounds of Formula I are capable of further forming pharmaceutically acceptable acid-addition and/or base salts. All of these forms are within the scope of the present invention. Thus, pharmaceutically acceptable acid addition salts of the compounds of Formula I include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, acetate, trifluoroacetate, propionate, caprylate, isobutyrate, oxalate, malonate, succinates suberate, sebacate, fumarate, maleate, mandelate, benzoate, chlorobenzoate, methylbenzoate, dinitrobenzoate, phthalate, benzensoulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M. et al., "Pharmaceutical Salts," *Journal of Pharmaceutical Science,* 1977; 66:1-19).

The acid addition salt of said basic compounds are prepared by contacting the free base form with a sufficient amount of the desired acid to produce the salt in the conventional manner.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge S. M., supra., 1977).

The base addition salts of said acidic compounds are prepared by contacting the free acid form with a sufficient amount of the desired base to produce the salt in the conventional manner.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

A "prodrug" is an inactive derivative of a drug molecule that requires a chemical or an enzymatic biotransformation in order to release the active parent drug in the body.

Specific and preferred values for the compounds of the present invention are listed below for radicals, substituents, and ranges are for illustration purposes only, and they do not exclude other defined values or other values within defined ranges for the radicals and substituents.

Preparation of Invention Compounds

Strategies for the preparation of invention compounds are depicted in Schemes I and II, and more specifically in Schemes 1-7. The numbering conventions for the "R" and "X" substituents, $R_1$, $R_2$, $X_2$, $R_3$, $X_1$, and $R_4$ are as provided for in the compounds of formula I.

Thus, as depicted retrosynthetically in Scheme I, the fused bicyclic core that characterizes the compounds of Formula I can be constructed via reaction of an appropriately substituted pyridinyl (Y=C—H, C—F, C—OMe) or pyrimidinyl (Y=N) derivative, as depicted by structure (1) with (2-chloro-acetyl)-carbamic acid ethyl ester, N-(chloroacetyl)-N'-ethyl-urea or an equivalent, in the presence of an amine base. The requisite appropriately substituted pyridinyl (Y=C—H, C—F, C—OMe) or pyrimidinyl (Y=N) derivatives 1 can be prepared by coupling compound 2, with compound 3, or the like.

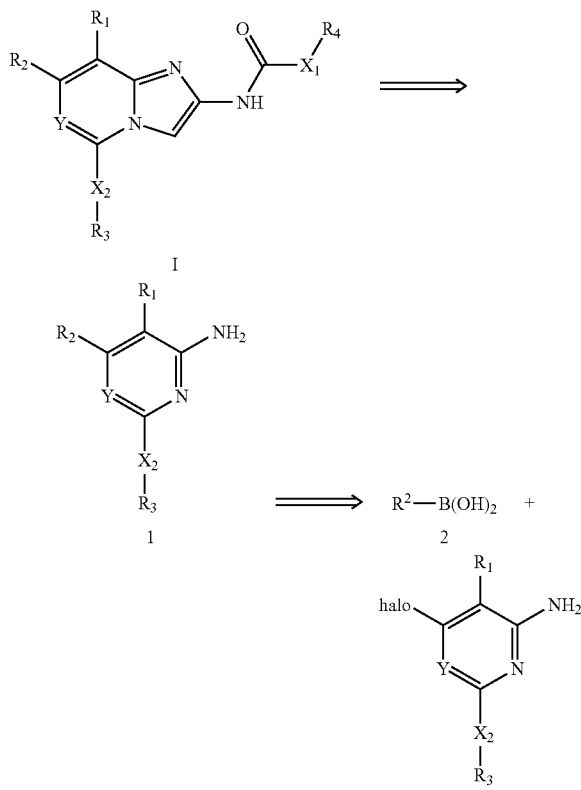

Schemes 1 and 2 exemplify an approach to compounds wherein $R_2$ is aryl, heteroaryl, Y is N, C—H, C—F, or C—OMe, and $X_1$ is NH or O. Thus, in Scheme 1, palladium catalyzed coupling of 4-bromo-pyridin-2-ylamine (1) with borane (2) provides [3,4']bipyridinyl-2'-ylamine (3). Reaction of compound 3 with (2-chloro-acetyl)-carbamic acid ethyl ester or 1-(2-chloro-acetyl)-3-ethyl-urea in the presence of an amine base such as lutidine (although other amine bases known to the practitioner could also be used) provides the invention compounds.

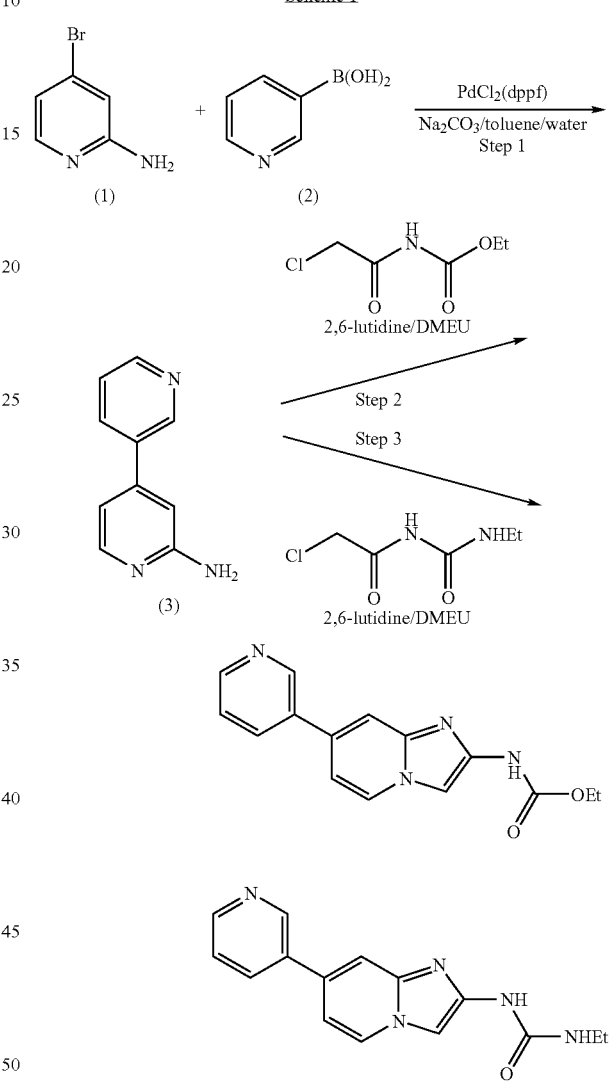

Similarly in Scheme 2, palladium-catalyzed coupling of compound (1) with borane (4) provides [5-(2-amino-pyridin-4-yl)-pyrimidin-2-yl]-dimethyl-amine (5). In a similar fashion as disclosed in Scheme 1, compound 5 can be converted to the invention compounds.

Scheme 2

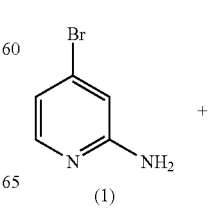

-continued
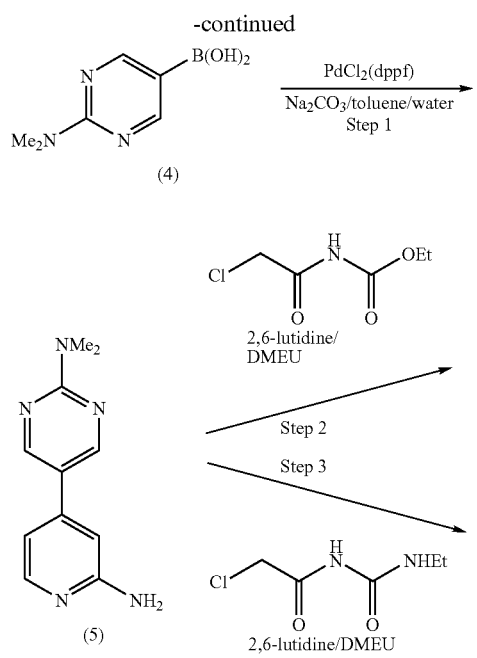
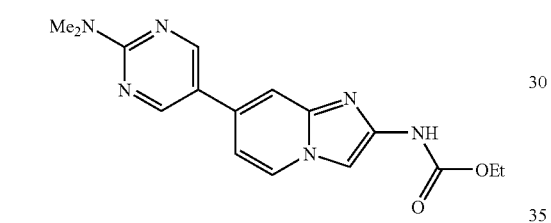
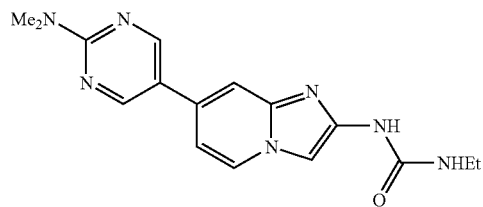
Schemes 3 and 4 provide additional variants of the approach presented in Scheme I.
Scheme 3
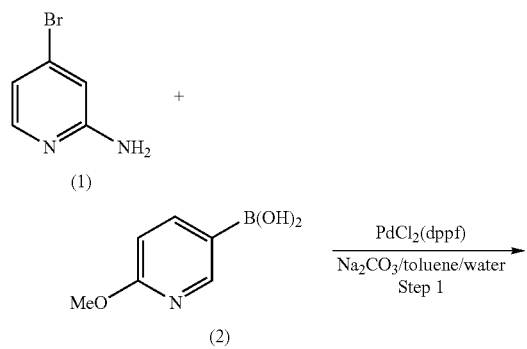
-continued
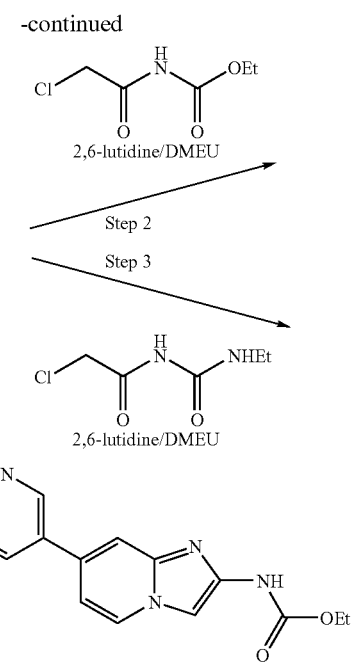
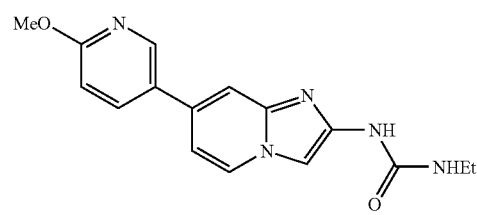
Scheme 4
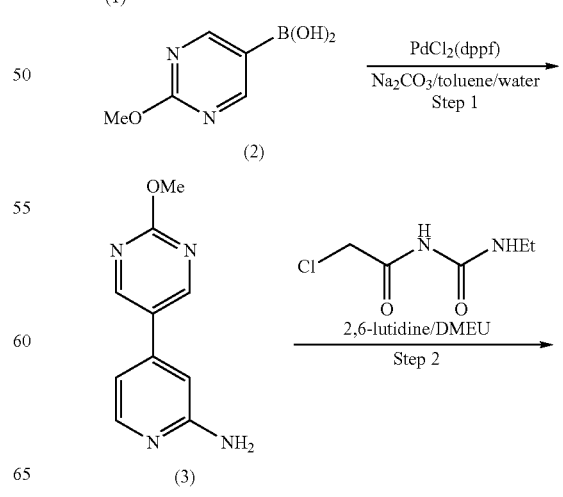

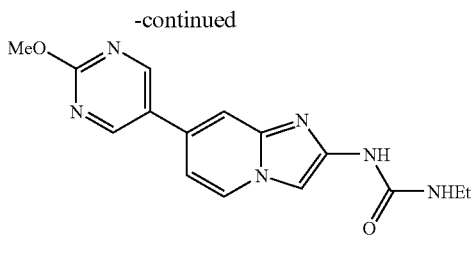

Scheme II discloses a retrosynthetic approach to variously substituted compounds of formula I wherein the combination of $X_2R_3$, is other than H. Initially compound 1, in which the combination of $X_2R_3$ is lower alkyl ester, heteroaryl, amino, or the like, is subjected to a coupling reaction with compound 2, similar to that disclosed in Scheme 1 above, generating compound 3. Compound 3 is then cyclized to compound 4 using bromo-pyruvate. Compound 4 can be rearranged to compound I, using the Lossen, Hofmann or Curtius rearrangements, which are described in Organic Syntheses Based on Named and Unnamed Reactions, Pergamon, Vol. 11, A. Hassner et al. (1994).

Depending upon the final product the reaction may be complete or subsequent functionalization reactions may be carried out as is known in the art to achieve the desired substituent at the $X_2R_3$ position. By way of illustrative example, when the invention compound $X_2$ is absent and $R_3$ is a methyl ester, methods for converting carboxylic esters into oxadiazoles or thiadiazoles are described in Synthesis 2003, 6, 899-905; Journal of Medicinal Chemistry 1991, 34(1), 140-151; Indian Journal of Heterocyclic Chemistry 2002, 12(3), 289-290. Likewise, the conversion of carboxylic esters into oxazoles is described in Synthesis 1998, (9), 1298-1304; Journal of Organic Chemistry 1989, 54(2), 431-434. Methods for preparing triazoles are described in Journal of the Chemical Society, Dalton Transactions 2002, (8), 1740-1746.

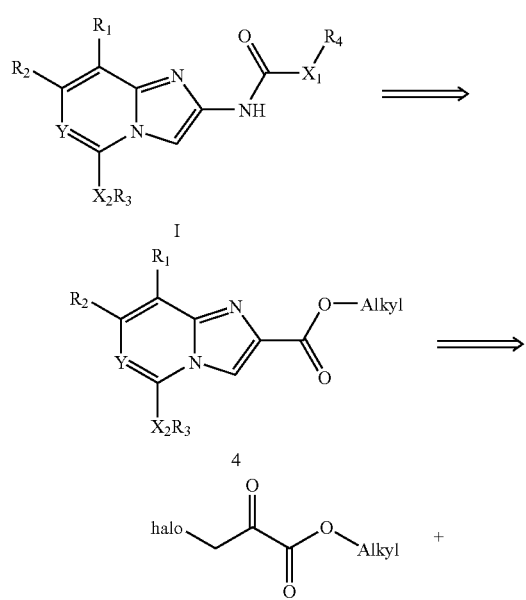

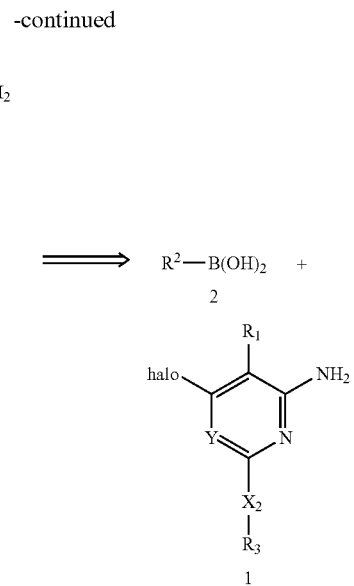

Scheme 5 provides an approach to invention compounds wherein $X_2$ is O, $R_2$ is aryl or heteroaryl (i.e HetAr), and $R_3$ is as defined herein.

Scheme 5

Synthesis (1998), (6), 867-872

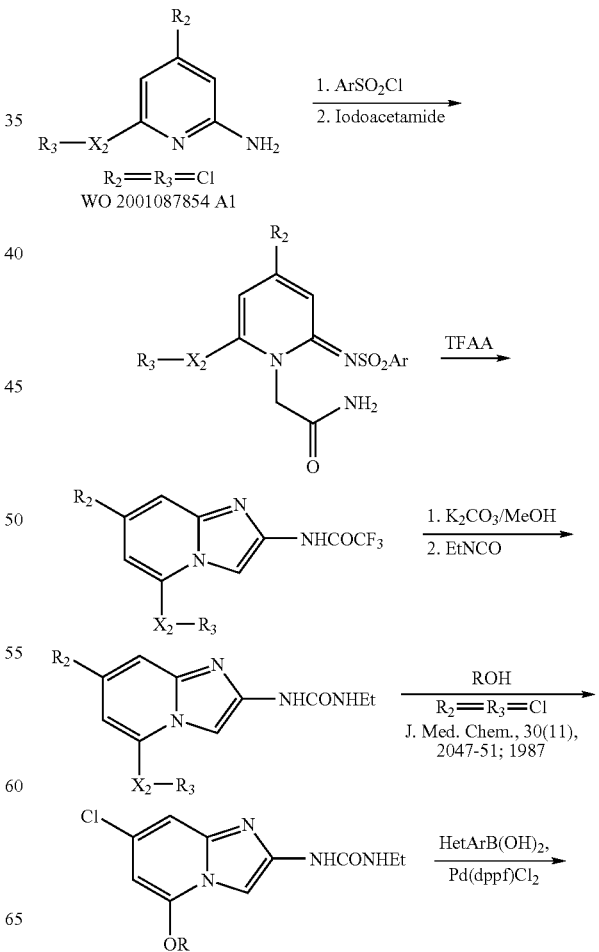

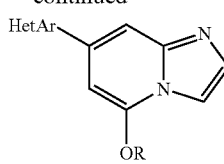

A variant of the Scheme 5 approach is provided in Scheme 6, wherein the $X_2$—$R_3$ (e.g., OR) is introduced at the beginning, rather than the end of the synthesis.

Scheme 6

Australian Journal of Chemistry (1982), 35(10), 2025-34

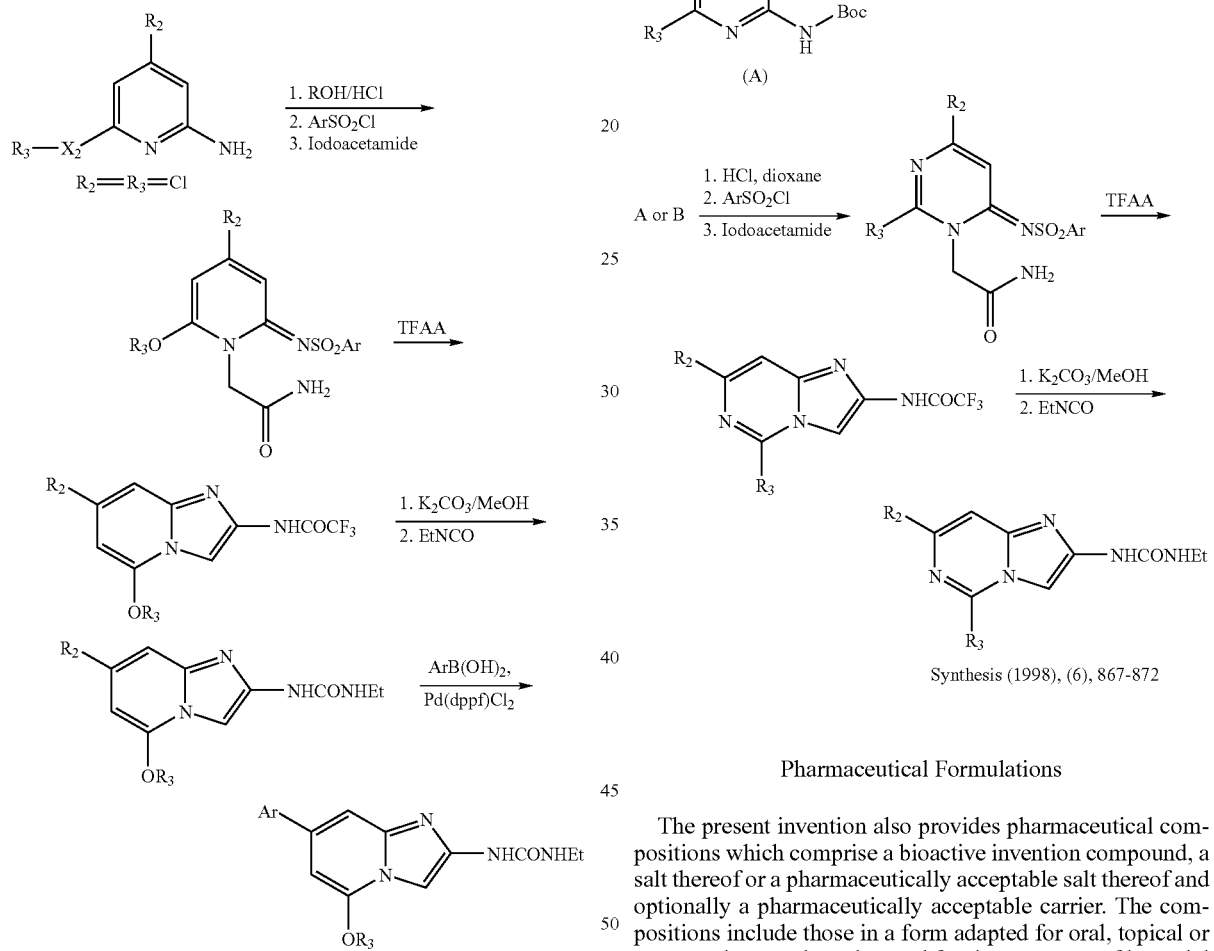

An approach to the preparation of compounds of formula I wherein Y is N is provided in Scheme 7 commencing with intermediates A or B, which may be prepared as disclosed in the art.

Scheme 7

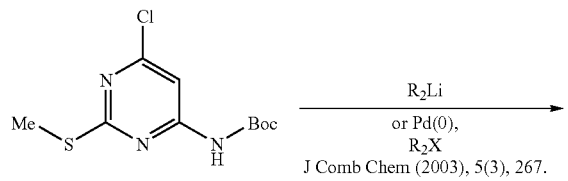

Synthesis (1998), (6), 867-872

Pharmaceutical Formulations

The present invention also provides pharmaceutical compositions which comprise a bioactive invention compound, a salt thereof or a pharmaceutically acceptable salt thereof and optionally a pharmaceutically acceptable carrier. The compositions include those in a form adapted for oral, topical or parenteral use and can be used for the treatment of bacterial infection in mammals including humans.

Compounds of the invention can be formulated for administration in any convenient way for use in human or veterinary medicine, by analogy with other bioactive agents such as antibiotics. Such methods are known in the art and are not described in detail herein.

The composition can be formulated for administration by any route known in the art, such as subdermal, inhalation, oral, topical, parenteral, etc. The compositions may be in any form known in the art, including but not limited to tablets, capsules, powders, granules, lozenges, creams or liquid preparations, such as oral or sterile parenteral solutions or suspensions.

The topical formulations of the present invention can be presented as, for instance, ointments, creams or lotions, eye ointments and eye or ear drops, impregnated dressings and aerosols, and may contain appropriate conventional additives such as preservatives, solvents to assist drug penetration and emollients in ointments and creams. The formulations may also contain compatible conventional carriers, such as cream or ointment bases and ethanol or oleyl alcohol for lotions. Such carriers may be present, for example, from about 1% up to about 98% of the formulation. For example, they may form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice.

Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerin, propylene glycol, or ethyl alcohol; preservatives, for example methyl or propyl p-hydroxybenzoate or sorbic acid, and, if desired, conventional flavoring or coloring agents.

For parenteral administration, fluid unit dosage forms are prepared utilizing the compound and a sterile vehicle, water being preferred. The compound, depending on the vehicle and concentration used, can be either suspended or dissolved in the vehicle or other suitable solvent. In preparing solutions, the compound can be dissolved in water for injection and filter sterilized before filling into a suitable vial or ampoule and sealing. Advantageously, agents such as local anesthetics, preservatives and buffering agents etc., can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain, for example, from about 0.1% to about 99 by weight, of the active material, depending on the method of administration. Where the compositions comprise dosage units, each unit will contain, for example, from about 5-900 mg of the active ingredient. The dosage as employed for adult human treatment will range, for example, from about 10 to 3000 mg per day, for instance 1500 mg per day depending on the route and frequency of administration. Such a dosage corresponds to about 1.5 to 500 mg/kg per day. Suitably the dosage is, for example, from about 5 to 20 mg/kg per day.

Biological Activity

In one embodiment, the invention provides methods of treating or preventing a bacterial infection in a subject, such as a human or other animal subject, comprising administering an effective amount of an invention compound as disclosed herein to the subject. In one embodiment, the compound is administered in a pharmaceutically acceptable form optionally in a pharmaceutically acceptable carrier. As used herein, an "infectious disorder" is any disorder characterized by the presence of a microbial infection, such as bacterial infections. Such infectious disorders include, for example central nervous system infections, external ear infections, infections of the middle ear, such as acute otitis media, infections of the cranial sinuses, eye infections, infections of the oral cavity, such as infections of the teeth, gums and mucosa, upper respiratory tract infections, lower respiratory tract infections, genitourinary infections, gastrointestinal infections, gynecological infections, septicemia, bone and joint infections, skin and skin structure infections, bacterial endocarditis, burns, antibacterial prophylaxis of surgery, and antibacterial prophylaxis in immunosuppressed patients, such as patients receiving cancer chemotherapy, or organ transplant patients. The compounds and compositions comprising the compounds can be administered by routes such as topically, locally or systemically. Systemic application includes any method of introducing the compound into the tissues of the body, e.g., intrathecal, epidural, intramuscular, transdermal, intravenous, intraperitoneal, subcutaneous, sublingual, rectal, and oral administration. The specific dosage of antimicrobial to be administered, as well as the duration of treatment, may be adjusted as needed and will be determined by the subjects physician.

The compounds of the invention may be used for the treatment or prevention of infectious disorders caused by a variety of bacterial organisms. Examples include Gram positive and Gram negative aerobic and anaerobic bacteria, including Staphylococci, for example *S. aureus*; Enterococci, for example *E. faecalis*; Streptococci, for example *S. pneumoniae; Haemophilus*, for example *H. influenza; Moraxella*, for example *M. catarrhalis*; and *Escherichia*, for example *E. coli*. Other examples include *Mycobacteria*, for example *M. tuberculosis*; intercellular microbes, for example *Chlamydia* and *Rickettsiae*; and *Mycoplasma*, for example *M. pneumoniae*.

The ability of a compound of the invention to inhibit bacterial growth, demonstrate in vivo activity, and enhanced pharmacokinetics are demonstrated using pharmacological models that are well known to the art, for example, using models such as the tests described below.

The following examples are provided to illustrate but not limit the claimed invention.

Example 1

Preparation of (7-Pyridin-3-yl-imidazo[1,2-a]pyridin-2-yl)-carbamic Acid Ethyl Ester and 1-Ethyl-3-(7-pyridin-3-yl-imidazo[1,2-a]pyridin-2-yl)-urea

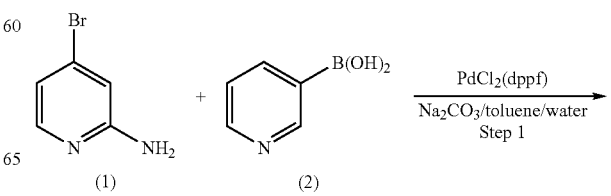

-continued

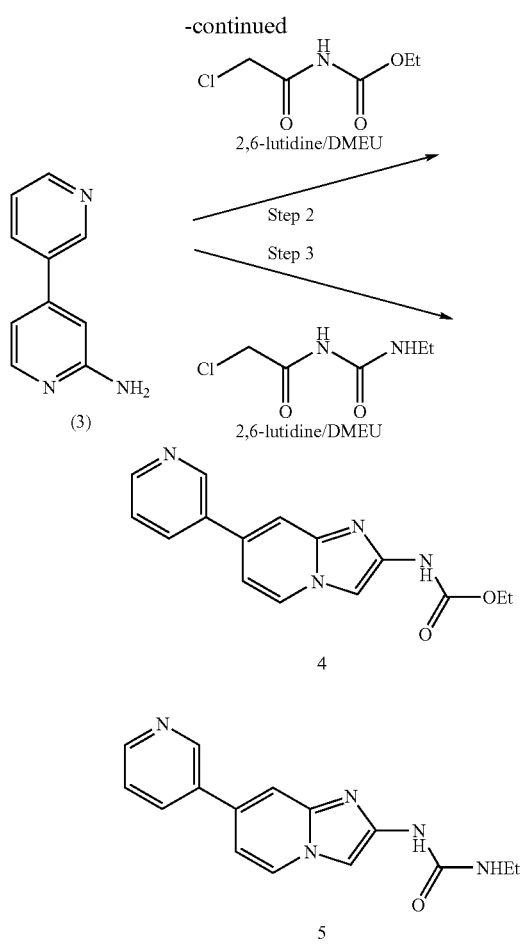

Step 1: Preparation of [3,4']Bipyridinyl-2'-ylamine

2N Na$_2$CO$_3$ (20 mL, 0.04 mol) was added to a suspension of aminopyridine (1) (1.00 g, 5.78 mmol) and boronic acid (2) (1.06 g, 8.67 mmol) in toluene (60 mL) and the mixture was purged with nitrogen gas. Bis(diphenylphosphino)ferrocene-palladium(II) chloride, dichloromethane complex [hereinafter "PdCl$_2$(dppf)"] (0.17 g, 0.21 mmol) was added and the mixture was refluxed under nitrogen for 1.5 hours. Ethyl acetate was added and the solution was washed with water, dried over Na$_2$SO$_4$ and adsorbed onto silica by removal of solvent in vacuo. The residue was chromatographed on silica, eluting with MeOH/EtOAc (1:15) to give product (3) as a powder (0.87 g, 87%). APCI-MS found: [M+H]$^+$=172.

Step 2: Preparation of (7-Pyridin-3-yl-imidazo[1,2-a]pyridin-2-yl)-carbamic Acid Ethyl Ester (Example 1A)

A solution of aminopyridine (3) (0.94 g, 5.49 mmol), ethyl chloroacetylcarbamate (1.09 g, 6.58 mmol) and 2,6-lutidine (0.76 mL, 6.58 mmol) in 1,3-dimethyl-2-imidazolidinone (6 mL) was warmed under nitrogen at 110° C. for 4.5 hours. The mixture was diluted with EtOAc and washed with water (6 times), then adsorbed onto silica by removal of solvent in vacuo. The product was chromatographed on silica. Elution with EtOAc gave foreruns, while MeOH/EtOAc (2:23) eluted product (79 mg, 5%) as a solid, mp 248-252° C. (decomposed).

Step 3: Preparation of 1-Ethyl-3-(7-pyridin-3-yl-imidazo[1,2-a]pyridin-2-yl)-urea (Example 1B)

A solution of aminopyridine (3) (0.73 g, 4.26 mmol), N-(chloroacetyl)-N'-ethylurea (0.84 g, 5.10 mmol) and 2,6-lutidine (0.59 mL, 5.10 mmol) in 1,3-dimethyl-2-imidazolidinone (7 mL) was warmed under nitrogen at 110° C. for 5 hours. The mixture was diluted with EtOAc and washed with water (6×), then adsorbed onto silica by removal of solvent in vacuo. Silica gel chromatography (EtOAc gradient to MeOH/EtOAc (2:23)) provided the product (0.76 mg, 6%) as a solid, mp 290-294° C. (decomposed).

Examples 2-4

Using the general procedure of Example I, but substituting the relevant starting material, the following compounds were prepared:

2A) [7-(2-Dimethylamino-pyrimidin-5-yl)-imidazo[1,2-a]pyridin-2-yl]-carbamic Acid Ethyl Ester

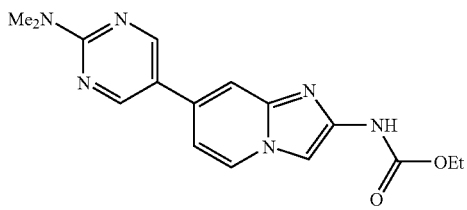

as a solid, mp 270-280° C. (decomposed). $^1$H NMR (400 MHz, DMSO-D6) δ ppm 10.14 (br, 1H), 8.82 (s, 2H), 8.54 (d, J=7.0 Hz, 1H), 7.82 (br s, 1H), 7.68 (d, J=1.8 Hz, 1H), 7.21 (dd, J=7.0, 1.8 Hz, 1H), 4.16 (q, J=7.1 Hz, 2H), 3.18 (s, 6H), 1.25 (t, J=7.1 Hz, 3H).

2B) 1-[7-(2-Dimethylamino-pyrimidin-5-yl)-imidazo[1,2-a]pyridin-2-yl]-3-ethyl-urea

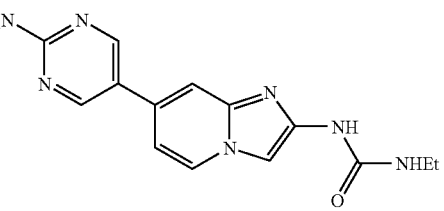

as a solid, mp 259-263° C. (decomposed). $^1$H NMR (400 MHz, DMSO-D6) δ ppm 8.84 (br s, 1H), 8.81 (s, 2H), 8.50 (d, J=7.1 Hz, 1H), 7.71 (s, 1H), 7.65 (d, J=1.8 Hz, 1H), 7.18 (dd, J=7.1, 1.8 Hz, 1H), 6.70 (br, 1H), 3.18 (s, 6H), 3.16 (dq, J=7.1, 5.4 Hz, 2H), 1.08 (t, J=7.1 Hz, 3H).

3A) [7-(6-Methoxy-pyridin-3-yl)-imidazo[1,2-a]pyridin-2-yl]-carbamic Acid Ethyl Ester

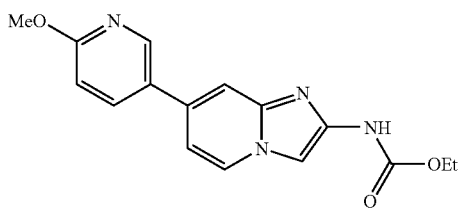

as a solid, mp 273-279° C. (decomposed). $^1$H NMR (400 MHz, DMSO-D6) δ ppm 10.17 (br s, 1H), 8.62 (d, J=2.3 Hz, 1H), 8.56 (d, J=7.1 Hz, 1H), 8.14 (dd, J=8.7, 2.3 Hz, 1H), 7.86 (br s, 1H), 7.70 (br s, 1H), 7.23 (dd, J=7.1, 1.8 Hz, 1H), 6.93 (d, J=8.7 Hz, 1H), 4.16 (q, J=7.1 Hz, 2H), 3.91 (s, 3H), 1.26 (t, J=7.1 Hz, 3H).

3B) 1-Ethyl-3-[7-(6-methoxy-pyridin-3-yl)-imidazo[1,2-a]pyridin-2-yl]-urea

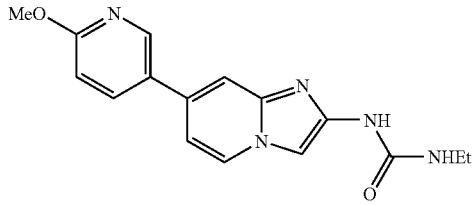

as a solid, mp 222-225° C. (decomposed). $^1$H NMR (400 MHz, DMSO-D6) δ ppm 8.86 (br s, 1H), 8.61 (d, J=2.3 Hz, 1H), 8.52 (d, J=7.1 Hz, 1H), 8.13 (dd, J=8.7, 2.3 Hz, 1H), 7.74 (br s, 1H), 7.67 (br s, 1H), 7.20 (dd, J=7.1, 1.8 Hz, 1H), 6.92 (d, J=8.7 Hz, 1H), 6.69 (br, 1H), 3.91 (s, 3H), 3.16 (dq, J=7.1, 5.7 Hz, 2H), 3.91 (s, 3H), 1.08 (t, J=7.1 Hz, 3H).

4) 1-Ethyl-3-[7-(2-methoxy-pyrimidin-5-yl)-imidazo[1,2-a]pyridin-2-yl]-urea

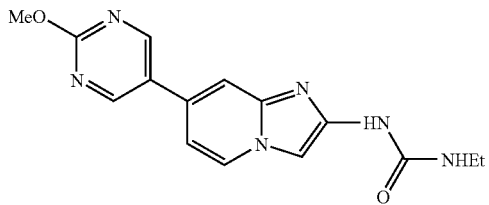

as a solid, mp >300° C. $^1$H NMR (400 MHz, DMSO-D6) δ ppm 9.05 (s, 2H), 8.90 (br, 1H), 8.57 (dd, J=7.0, 0.6 Hz, 1H), 7.80 (br s, 1H), 7.78 (s, 1H), 7.26 (dd, J=7.0, 1.8 Hz, 1H), 6.66 (br, 1H), 3.98 (s, 3H), 3.16 (dq, J=7.2, 5.5 Hz, 2H), 1.08 (t, J=7.2 Hz, 3H).

Example 5

Preparation of (7-Pyridin-3-yl-imidazo[1,2-c]pyrimidin-2-yl)-carbamic Acid Ethyl Esters

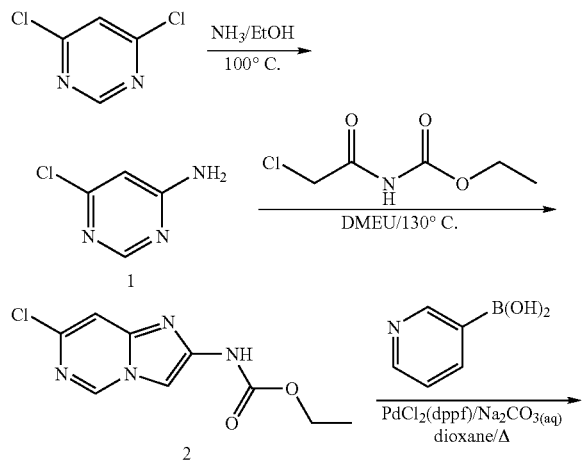

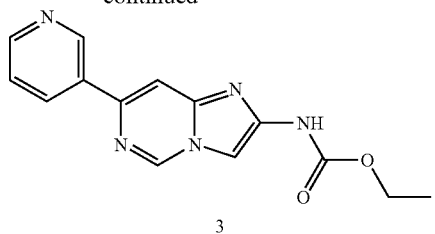

Step 1: Preparation of 6-Amino-4-chloropyrimidine (1)

4,6-Dichloropyrimidine (10.0 g, 67.1 mmol) in ammonia saturated ethanol (40 mL) was heated to 100° C. in a stainless steel pressure vessel for 1.5 h. Removal of the solvent in vacuo gave a solid which was triturated with water (270 mL) then filtered to give 6-amino-4-chloropyrimidine (1) (6.18 g, 71%) as white crystals. APCI-MS Found [M+H]$^+$=130, 132.

Step 2: Preparation of (7-Chloro-imidazo[1,2-c]pyrimidin-2-yl)-carbamic Acid Ethyl Ester (2)

A solution of 6-amino-4-chloropyrimidine (1) (0.504 g, 3.89 mmol) and N-chloroacetylurethane (0.770 g, 4.65 mmol) in 1,3-dimethyl-2-imidazolidinone (10 mL) was heated to 130° C. under nitrogen for 3 h. N-Chloroacetylurethane (0.770 g, 4.65 mmol) was added and the mixture was heated to 130° C. under nitrogen for a further 3.5 h. The black oily solution was poured onto ice (200 g) and the aqueous solution was extracted with ethyl acetate (3×250 mL). The organic fractions were combined, removal of solvent in vacuo gave an oily solid which was triturated with ether. Filtration of the solid and washing with ether gave urethane (2) (88 mg, 9%) as a solid. APCI-MS Found [M+H]$^+$=241, 243.

Step 3: Preparation of (7-Pyridin-3-yl-imidazo[1,2-c]pyrimidin-2-yl)-carbamic Acid Ethyl Ester A mixture of (2) (0.143 g, 0.594 mmol) and 3-pyridineboronic acid (0.110 g, 0.895 mmol) in 1,4-dioxane (10 mL) and aqueous potassium carbonate (2 mol L$^{-1}$, 2 mL) was purged with nitrogen. Bis(diphenylphosphino)ferrocenepalladium (II) chloride, dichloromethane complex (0.030 g, 0.037 mmol) was added and the mixture was refluxed under nitrogen for 16 h. The mixture was filtered through celite and the filter cake was washed with hot dioxane (2×50 mL). Removal of the solvent in vacuo gave a solid which was purified by silica gel chromatography (9:1; ethyl acetate:methanol) to give substituted pyridine (3) (0.104 g) as a solid. HRMS-EI$^+$ Found 283.1067. Calcd for C$_{14}$H$_{13}$N$_5$O$_2$: 283.1069.

Example 6

Preparation of 1-Ethyl-3-{7-[6-(2-morpholin-4-yl-ethoxy)-pyridin-3-yl]-imidazo[1,2-a]pyridin-2-yl}-urea

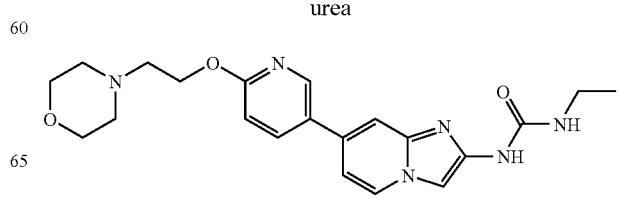

Scheme 1)-Preparation of Pyridyl Side Chain

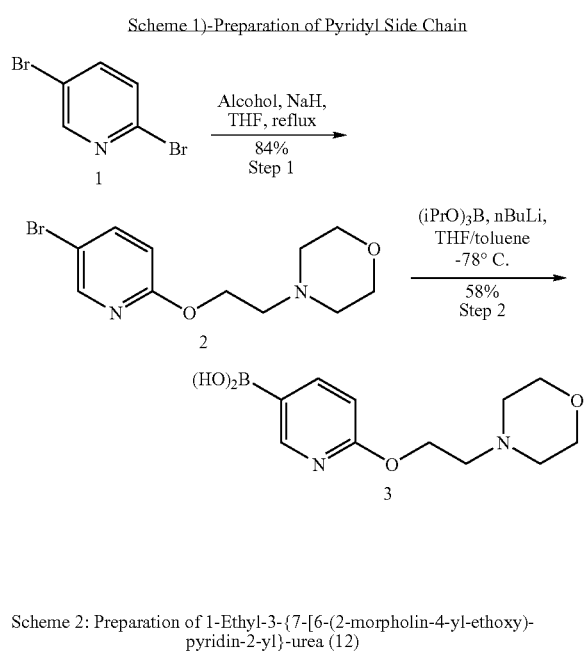

Scheme 2: Preparation of 1-Ethyl-3-{7-[6-(2-morpholin-4-yl-ethoxy)-pyridin-2-yl}-urea (12)

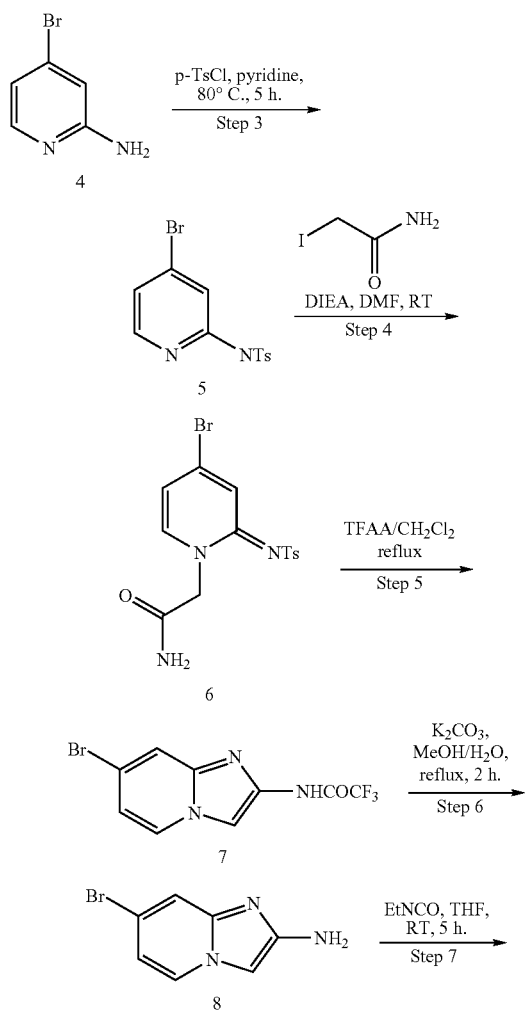

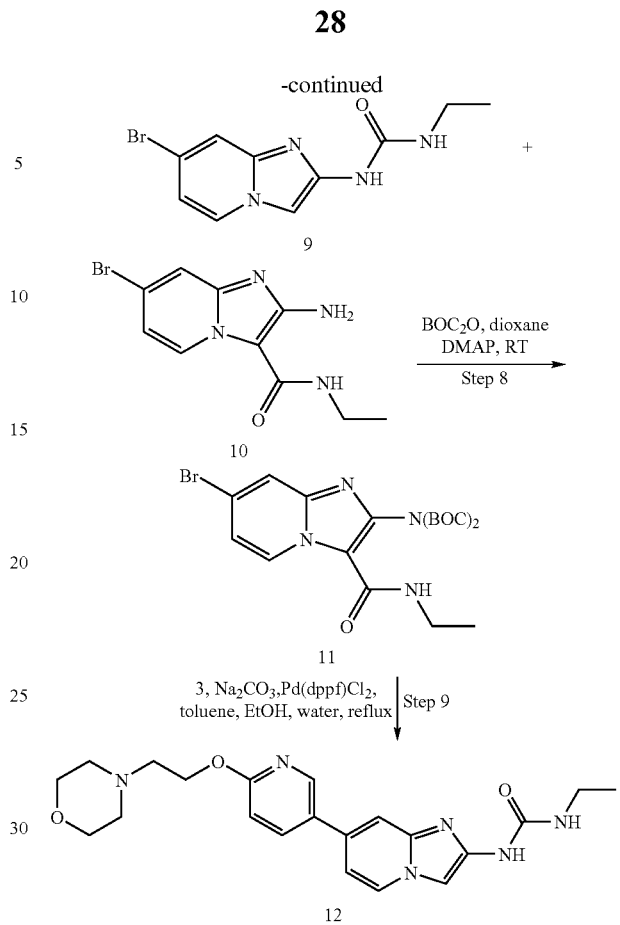

Experimental Procedure

Step 1 (Synthetic Scheme 1):

A solution of 4-(2-hydroxyethyl)morpholine (2.77 g, 21.1 mmol) in dry tetrahydrofuran (5 mL) was added to a refluxing suspension of sodium hydride (557 mg, 23.2 mmol) in tetrahydrofuran (50 mL). This mixture was heated at reflux temperature for 3 h., then 2,5-dibromopyridine (1; 5.00 g, 21.1 mmol) added as a solid (portion wise). The resulting mixture was then heated at reflux for 15 h. After allowing the reaction mixture to cool, it was diluted with ethyl acetate (200 mL), then washed with water (200 mL). The water fraction was back-extracted with ethyl acetate (100 mL). The combined ethyl acetate fractions were washed with water (2×200 mL), then brine (100 mL) and dried over sodium sulfate. The drying agent was removed by filtration and the resultant liquor was concentrated under reduced pressure. The resulting yellow oil was purified by chromatography on silica gel (100% dichloromethane gradient to 10% methanol/dichloromethane). Compound 2 was isolated as a yellow oil (yield: 5.06 g, 84%);

Step 2:

A solution of bromide 2 (5.00 g, 17.4 mmol) and triisopropylborate (3.93 g, 20.9 mmol) in a mixture of dry tetrahydrofuran (9 mL) and dry toluene (36 mL) was placed under nitrogen and cooled to −78° C. (acetone/dry ice). n-Butyllithium (2.5 M in hexanes; 8.36 mL, 20.9 mmol) was added drop wise over 20 minutes and the mixture was allowed to stir for 0.5 h. at −78° C. The reaction mixture was then removed from the cold bath and water (50 mL) added. 2 M hydrogen chloride (25 mL) was then added and the mixture stirred for 1 h at 23° C. After this time further 2 M hydrogen chloride (25 mL) was added and the mixture partitioned into ethyl acetate (100 mL). The aqueous layer was collected, then the ethyl acetate layer extracted with further 2 M hydrogen chloride (25 mL). All acidic fractions were combined, neutralized with conc. ammonia, and the resulting oil extracted into ethyl acetate (8×50 mL). The first fraction contained both the desired product 3 and unreacted starting material 2 by thin layer chromatography and these were separated by chromatography on silica gel (5-10% methanol/dichloromethane). All remaining fractions contained pure boronic acid 3. All pure fractions were then combined to give compound 3 as a foam (yield: 2.56 g, 58%); $^1$H NMR [400 MHz, $(CD_3)_2SO$] δ 8.26 (d, J=1.3 Hz, 1H), 8.10 (s, 2H), 7.99 (dd, J=8.3, 2.0 Hz, 1H), 6.75 (d, J=8.3 Hz, 1H), 4.38 (t, J=5.8 Hz, 2H), 3.56 (t, J=4.7 Hz, 4H), 2.66 (t, J=5.9 Hz, 2H), 2.45 (t, J=4.6 Hz, 4H).

Step 3 (Synthetic Scheme 2):

2-Amino-4-bromopyridine 4 (5.00 g, 28.9 mmol) and p-toluenesulfonyl chloride (6.10 g, 31.8 mmol) were dissolved in dry pyridine (100 mL) and heated at 80° C. for 5 h. The pyridine was removed under reduced pressure to give a solid. The solid was suspended in ethyl acetate, then collected by filtration and washed with ethyl acetate to give the tosylate 5 as a crystalline solid (yield: 7.50 g, 79%); $^1$H NMR [400 MHz, $(CD_3)_2SO$] δ 11.6 (v br s, 1H), 7.99 (br d, J=5.6 Hz, 1H), 7.78 (d, J=8.3 Hz, 2H), 7.37 (d, J=7.0 Hz, 2H), 7.27 (br s, 1H), 7.17 (br d, J=5.2 Hz, 1H), 2.36 (s, 3H).

Step 4:

Tosylate 5 (7.05 g, 21.5 mmol) was dissolved in dry dimethyl formamide (120 mL), to this was added diisopropylethylamine (3.06 g, 23.7 mmol) and iodoacetamide (4.38 g, 23.7 mmol). The mixture was stirred at 23° C. for 24 h. then concentrated under reduced pressure to provide an oil. This oil was diluted with water (300 mL) and the resulting solid collected by filtration and washed with ethyl acetate, providing the desired compound 6 (yield: 7.39 g, 89%); $^1$H NMR [400 MHz, $(CD_3)_2SO$] δ 7.96 (d, J=7.1 Hz, 1H), 7.74 (s, 1H), 7.66 (d, J=8.2 Hz, 2H), 754 (d, J=2.1 Hz, 1H), 7.35 (s, 1H), 7.29 (d, J=8.0 Hz, 2H), 7.00 (dd, J=7.1, 2.2 Hz, 1H), 4.78 (s, 2H), 2.35 (s, 3H).

Step 5:

Compound 6 (3.18 g, 8.27 mmol) was suspended in a mixture of dichloromethane (60 mL) and trifluoroacetic anhydride (60 mL). This mixture was heated at reflux temperature for 3 h. All solvent was removed under reduced pressure and the residue partitioned between ethyl acetate (200 mL) and sat. sodium bicarbonate (200 mL). The ethyl acetate layer was then washed with additional sodium bicarbonate (200 mL), brine (100 mL), and dried (sodium sulfate). The solvent was removed under reduced pressure to give a crude pink solid which was purified by filtration through a plug of silica gel (50% ethyl acetate/hexanes), then the resulting white solid suspended in diethyl ether and collected by filtration. Trifluoroacetamide 7 was isolated as a solid (yield: 1.57 g, 62%); $^1$H NMR [400 MHz, $(CD_3)_2SO$] δ 12.49 (s, 1H), 8.57 (d, J=7.2 Hz, 1H), 8.28 (s, 1H), 7.84 (d, J=1.9 Hz, 1H), 7.13 (dd, J=7.2, 2.0 Hz, 1H).

Step 6:

Trifluoroacetamide 7 (607 mg, 1.97 mmol) was dissolved/suspended in a mixture of methanol (35 mL) and water (23 mL), to which was added potassium carbonate (1.36 g, 9.86 mmol). This mixture was heated at reflux for 2 h, at which point thin layer chromatography (5% methanol/dichloromethane) showed complete reaction of the starting material 7 to give a single, more polar product. The reaction was allowed to cool, diluted with water (100 mL) and extracted with ethyl acetate (4×50 mL). The combined ethyl acetate fractions were then washed with water (2×50 mL), brine (50 mL), dried (sodium sulfate) and the solvent removed under reduced pressure to afford the desired amine 8 as a solid which decomposed rapidly (to baseline overnight) and was used directly in the next step (yield: 375 mg, 97%); $^1$H NMR [400 MHz, $(CD_3)_2SO$] δ 8.24 (d, J=7.1 Hz, 1H), 7.42 (d, J=2.0 Hz, 1H), 7.02 (s, 1H), 6.85 (dd, J=7.0, 2.0 Hz, 1H), 5.27 (v br s, 2H).

Step 7:

Amine 8 (823 mg, 4.18 mmol) was dissolved/suspended in dry tetrahydrofuran (70 mL), the reaction flushed with nitrogen, then ethyl isocyanate (1.80 g, 23.0 mmol) added. This mixture was stirred at 23° C. for 5 h., then all solvent removed under reduced pressure. The resulting crude solid was then purified by chromatography on silica gel, (2% methanol/dichloromethane as eluant) to give a mixture of products 9 and 10 (yield: 777 mg, 66%). This mixture (9:10 in a ratio of 56:44 by $^1$H NMR) was used directly and subsequently separated at step 8.

Step 8:

A mixture of compounds 9 and 10 (777 mg, 2.76 mmol) was dissolved/suspended in dioxane (120 mL) and triethylamine (1 mL). Di-tert-butyldicarbonate (1.20 g, 5.51 mmol) and 4-dimethylaminopyridine (31 mg, 0.28 mmol) were added and the mixture stirred at 23 C for 3 h. All solvent was removed under reduced pressure to afford a crude solid which was purified by chromatography on silica gel. The bis-BOC compound 11 was eluted first (50% ethyl acetate/hexanes as eluant) and discarded then the desired compound 9 was recovered (100% ethyl acetate) as a solid (296 mg); $^1$H NMR [400 MHz, $(CD_3)_2SO$] δ 8.89 (s, 1H), 8.45 (dd, J=7.1, 0.5 Hz, 1H), 7.79 (s, 1H), 7.63 (d, J=1.9 Hz, 1H), 6.99 (dd, J=7.1, 2.0 Hz, 1H), 6.53 (br s, 1H), 3.14 (dq, J=7.2, 5.6 Hz, 2H), 1.06 (t, J=7.2 Hz, 3H).

Step 9:

Compound 9 (135 mg, 0.48 mmol) was suspended in toluene (8 mL), to which was added a solution of the boronic acid 3 (181 mg, 0.72 mmol) in ethanol (2 mL). 2 M Sodium carbonate (2.0 mL) was added and the flask placed under nitrogen. The catalyst Bis(diphenylphosphino)ferrocenepalladium(II) chloride, dichloromethane complex (31 mg, 0.02 mmol) was added last and the reaction mixture heated at reflux temperature for 2 h., at which point all starting material had been consumed by thin layer chromatography (5% methanol/dichloromethane). After allowing the reaction to cool, all solvents were removed under reduced pressure to give a residue which was purified by chromatography on silica gel (2% methanol/dichloromethane as eluant), affording 1-ethyl-3-{7-[6-(2-morpholin-4-yl-ethoxy)-pyridin-2-yl}-urea (12) as a solid after trituration with ethyl acetate (94 mg); Anal. calcd for $C_{21}H_{26}N_6O_3$: C, 61.5; H, 6.4; N, 20.5. Found: C, 61.1; H, 6.3; N, 20.2.

Example 7
Preparation of 1-Ethyl-3-(5-hydroxymethyl-7-pyridin-3-yl-imidazo[1,2-a]pyridin-2-yl)-urea (Example 7A, Compound 12 in Scheme), 1-Ethyl-3-(5-formyl-7-pyridin-3-yl-imidazo[1,2-a]pyridin-2-yl)-urea (13), and 2-(3-Ethyl-ureido)-7-pyridin-3-yl-imidazo[1,2-a]pyridine-5-carboxylic Acid Methyl Ester (Example 7B, Compound 14 in Scheme)
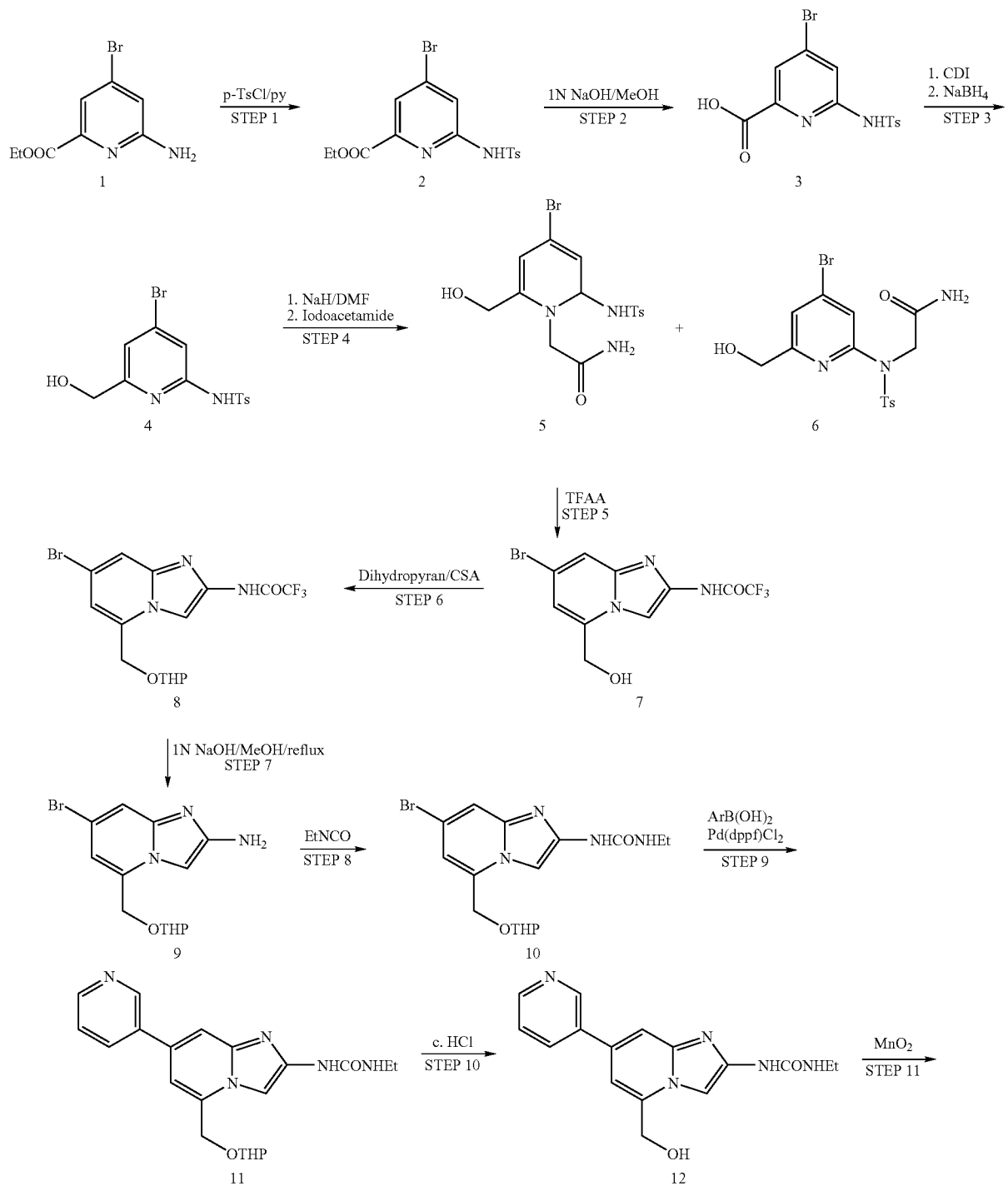

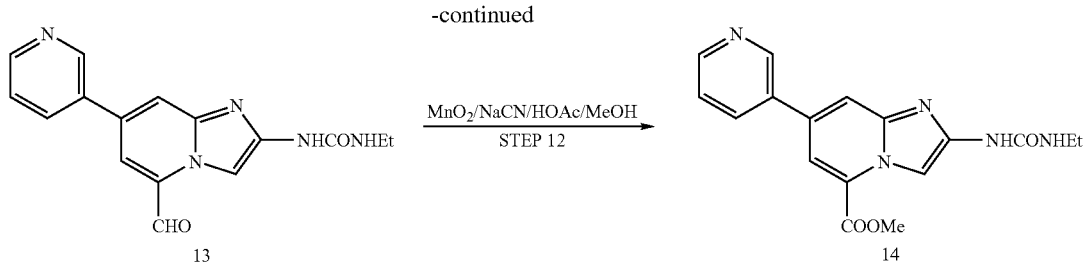

Step 1:

A solution of aminopyridine (1) (0.50 g, 2.04 mmol) and p-toluenesulfonyl chloride (0.43 g, 2.24 mmol) in dry pyridine (10 mL) was warmed at 85° C. for 15 h. The solvent was removed in vacuo and the residue was partitioned between saturated aqueous sodium bicarbonate and ethyl acetate. The ethyl acetate layer was washed well with water and worked up to give an oily solid, which was chromatographed on silica. Elution with ethyl acetate/petroleum ether (3:7) gave (2) as a colorless foam (0.66 g, 81%). APCI-MS Found [M+H]=401, 399.

Step 2:

To a solution of the ester (2) (3.71 g, 9.29 mmol) in methanol (200 mL) was added 1 N sodium hydroxide (27.0 mL, 0.027 mol) and the mixture was stirred at 23° C. for 3 h. After acidification to pH~3 with conc. hydrogen chloride the methanol was removed in vacuo and the residue was extracted with ethyl acetate. The extract was worked up to give the acid (3) as a solid (3.33 g, 96.5%). APCI-MS Found [M+H]=374, 372.

Step 3:

1,1'-Carbonyldiimidazole (2.18 g, 0.013 mol) was added in portions to a solution of the acid (3) (3.33 g, 8.97 mmol) in dry tetrahydrofuran (150 mL) and the solution was stirred at 23° C. for 1 h and then poured into a vigorously stirred solution of sodium borohydride (1.02 g, 0.027 mol) in water (200 mL). After stirring at 23° C. for 30 min the mixture was acidified to pH=3 with conc. hydrogen chloride, diluted with water and extracted three times with ethyl acetate. The combined extracts were washed with 1N hydrogen chloride and worked up to give an oil, which was chromatographed on silica. Elution with ethyl acetate/petroleum ether (1:1) gave the alcohol (4) (3.17 g, 98%) as a solid. APCI-MS Found [M+H]=359, 357.

Step 4:

Sodium hydride (0.57 g of a 60% dispersion in mineral oil, 0.014 mol) was added in portions at 23° C. to a stirred solution of the alcohol (4) (4.22 g, 0.012 mol) in dry dimethyl formamide (60 mL). After 10 min a solution of iodoacetamide (2.68 g, 0.014 mol) in dimethyl formamide (10 mL) was added and the solution was stirred at 23° C. for 16 h. Silica gel was added and the reaction mixture was adsorbed directly onto it by concentration of the mixture to dryness in vacuo. The product was chromatographed on silica. Elution with ethyl acetate gave isomer (6) as a white solid (3.16 g, 63%). Elution with methanol/ethyl acetate (5:95) gave the required product (5) as a foamy solid (4.92 g-contains sodium iodide as well). This material was used directly in the next step. APCI-MS Found [M+H]=416, 414.

Step 5:

The crude product (5) from the above reaction (4.92 g) was dissolved in dichloromethane/trifluoroacetic anhydride (1:1) (40 mL) and the solution was refluxed for 2 h. After removal of the solvents in vacuo the residue was dissolved in methanol (50 mL), saturated aqueous sodium bicarbonate (10 mL) was added and the mixture was stirred at 23° C. for 15 min. The mixture was diluted with water and extracted with ethyl acetate. The combined extracts were concentrated in vacuo. Silica gel chromatography (ethyl acetate gradient to methanol/ethyl acetate (5:95)) provided the product (7) as a solid (1.44 g). APCI-MS Found [M+H]=340, 338.

Step 6:

Dihydropyran (5 mL, 0.055 mol) was added to a solution of the alcohol (7) (1.10 g, 3.25 mmol) and camphor-10-sulfonic acid (1.20 g, 5.16 mmol) in tetrahydrofuran (100 mL) and the solution was stirred at 23° C. for 2 h. Excess aqueous saturated sodium bicarbonate solution was added and the mixture was extracted with ethyl acetate. The combined extracts were concentrated under reduced pressure to give the tetrahydropyran ether (8) as an oil (1.31 g). APCI-MS Found [M+H]= 424, 422.

Steps 7 and 8:

A solution of the trifluoroacetamide (8) (1.60 g, 3.79 mmol) in ethanol (50 ml) and 1N sodium hydroxide (20 mL) was refluxed for 30 min. Most of the ethanol was removed in vacuo and the residue was diluted with water and extracted with ethyl acetate. The extract was concentrated to give the crude amino compound (9) as an oily solid, which was used directly. APCI-MS Found [M+H]=328, 326. The crude amine (9) was dissolved in dry tetrahydrofuran (40 ml) and the solution was flushed with nitrogen. Ethyl isocyanate (0.61 mL, 7.82 mmol) was added and the solution was stirred at 23° C. for 2.5 h. A further 0.20 mL of ethyl isocyanate was added and stirring was continued for a total of 5 h. The solvent was removed in vacuo and the residue was adsorbed onto silica gel. Silica gel chromatography (ethyl acetate/petroleum ether gradient to ethyl acetate) provided the urea (10) as a powder (0.47 g). APCI-MS Found [M+H]=399, 397.

Step 9:

A suspension of pyridyl-3-boronic acid (81 mg, 0.66 mmol) in ethanol (2 mL) was added to a suspension of the bromide (10) (0.17 g, 0.43 mmol) in toluene (5 mL). After a few minutes a clear solution was obtained. 2N Sodium carbonate solution (1.5 mL) was added and the mixture was purged with nitrogen. Bis(diphenylphosphino)ferrocenepalladium(II) chloride, dichloromethane complex (18 mg, 0.022 mmol) was added and the mixture was refluxed under nitrogen for 3 h. The mixture was diluted with water and extracted with ethyl acetate. The extract was concentrated. Silica gel chromatography (ethyl acetate gradient to methanol/ethyl acetate (8:92)) provided the product (11) as a solid (0.13 g). APCI-MS Found [M+H]=396.

Step 10:

Conc. hydrogen chloride (1 mL) was added to a solution of the urea (11) (0.13 g, 0.33 mmol) in methanol (10 ml) and the solution was stirred at 23° C. for 30 min. The solvents were removed in vacuo and the residue was partitioned between saturated aqueous sodium bicarbonate and ethyl acetate. The extract was concentrated to give a powder, which was triturated with diethyl ether, to leave 1-ethyl-3-(5-hydroxymethyl-7-pyridin-3-yl-imidazo[1,2-a]pyridin-2-yl)-urea, (12) as a powder (47 mg). HRFAB-MS Found: [M+H]=312.1457. $C_{16}H_{18}N_5O_2$ requires 312.1460.

Steps 11 and 12:

Activated manganese dioxide (600 mg) was added to a solution of the alcohol (12) (90 mg, 0.29 mmol) in a mixture of ethyl acetate (20 mL) and methanol (10 mL) and the mixture was stirred vigorously at 23° C. for 2 h. APCI-MS Found [M+H]=310. The reaction mixture was filtered through Celite, washing through with more ethyl acetate/methanol. The combined filtrates were concentrated to dryness to give the aldehyde, 1-Ethyl-3-(5-formyl-7-pyridin-3-yl-imidazo[1,2-a]pyridin-2-yl)-urea (13), which was used directly in the next step. To a solution of the crude aldehyde (13) in methanol (20 mL) was added NaCN (75 mg, 1.53 mmol) and acetic acid (26 µL, 0.46 mmol). Activated manganese dioxide (600 mg) was added last and the mixture was stirred at 23° C. for 3 h, then filtered through Celite, washing through with more methanol. The combined filtrates were concentrated to dryness to leave a solid which was adsorbed onto silica. Silica gel chromatography (ethyl acetate gradient to methanol/ethyl acetate (8:92)) provided 2-(3-Ethyl-ureido)-7-pyridin-3-yl-imidazo[1,2-a]pyridine-5-carboxylic acid methyl ester (14) (36 mg). HRFAB-MS Found: [M+H]= 340.1413. $C_{17}H_{18}N_5O_3$ requires 340.1410.

Example 8

Preparation of 1-Ethyl-3-(7-pyrimidin-5-yl-imidazo[1,2-a]pyridin-2-yl)-urea

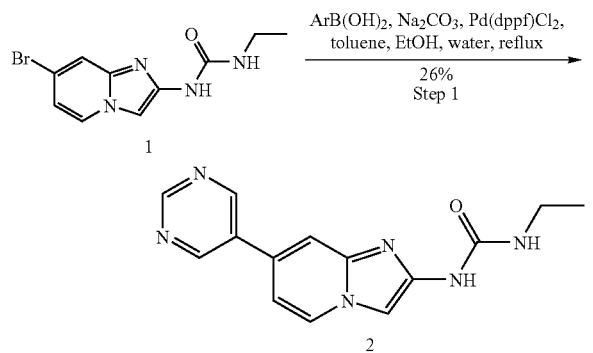

Step 1:

Compound 1 was prepared as described in the experimental provided for Example Number 6 (i.e. compound Number 9 of Example 6). Compound 1 (145 mg, 0.51 mmol) was suspended in toluene (9 mL), then a suspension of pyrimidine-5-boronic acid (96 mg, 0.77 mmol) in ethanol (2.5 mL) was added. 2 M Sodium carbonate (2.2 mL) was added and the flask placed under nitrogen. The catalyst Bis(diphenylphosphino)ferrocenepalladium(II) chloride, dichloromethane complex (23 mg, 0.03 mmol) was added last and the reaction mixture heated at reflux temperature for 2 h. thin layer chromatography (5% methanol/dichloromethane) at this point showed unreacted starting material, thus additional boronic acid (96 mg, 0.77 mmol) and catalyst (23 mg, 0.03 mmol) were added and the reaction heated at reflux for a further 3 h., whereupon the reaction was complete by thin layer chromatography. After allowing the reaction to cool, all solvents were removed under reduced pressure to give a residue which was purified by chromatography on silica gel (2% methanol/dichloromethane), affording 1-ethyl-3-(7-pyrimidin-5-yl-imidazo[1,2-a]pyridin-2-yl)-urea (2) as a solid after trituration with ethyl acetate (yield: 38 mg, 26%). HRMS (EI⁺) calcd $C_{14}H_{14}N_6O$ (M⁺) 282.1229, found 282.1230.

Example 9

Preparation of 1-[7-(3,5-Dimethyl-isoxazol-4-yl)-imidazo[1,2-a]pyridin-2-yl]-3-ethyl-urea

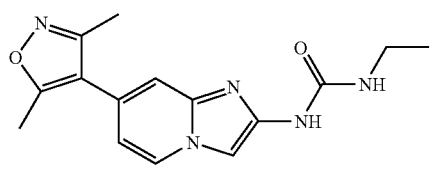

Using the general procedure of Example 8, but substituting the relevant starting material, 1-[7-(3,5-dimethyl-isoxazol-4-yl)-midazo[1,2-a]pyridin-2-yl]-3-ethyl-urea was obtained as a solid. Mp 204-206° C.

Example 10

Preparation of 1-[7-(1-Benzyl-1H-pyrazol-4-yl)-imidazo[1,2-a]pyridin-2-yl]-3-ethyl-urea

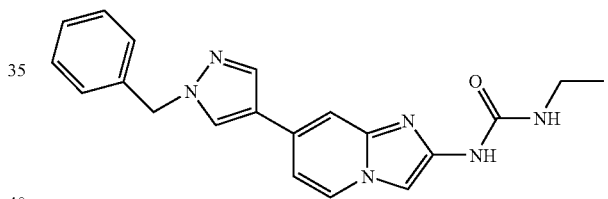

Using the generalized procedure of Example 8, but substituting the relevant starting material, 1-[7-(1-benzyl-1H-pyrazol-4-yl)-imidazo[1,2-a]pyridin-2-yl]-3-ethyl-urea was obtained as a solid following recrystallization. LCMS (APCI⁺) 361.2 (100%, MH⁺).

Example 11

Preparation of 1-Ethyl-3-{7-[6-(4-methyl-piperazin-1-yl)-pyridin-3-yl]-imidazo[1,2-a]pyridin-2-yl}-urea

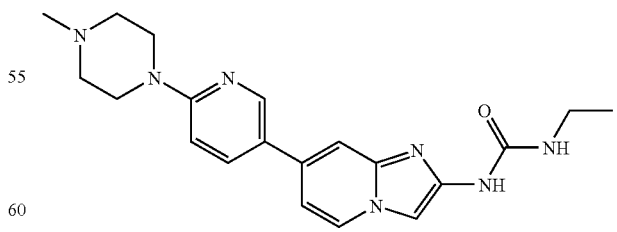

Using the generalized procedure of Example 8, but substituting the relevant starting material, 1-ethyl-3-{7-[6-(4-methyl-piperazin-1-yl)-pyridin-3-yl]-imidazo[1,2-a]pyridin-2-yl}-urea was obtained HRMS (FAB⁺) calcd $C_{20}H_{26}N_7O$ (MH⁺) 380.2200, found 380.2192.

Example 12

Preparation of 1-Ethyl-3-[7-(1-methyl-1H-pyrazol-4-yl)-imidazo[1,2-a]pyridin-2-yl]-urea

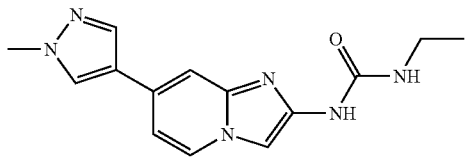

Using the general procedure of Example 8, but substituting the relevant starting material, 1-ethyl-3-[7-(1-methyl-1H-pyrazol-4-yl)-imidazo[1,2-a]pyridin-2-yl]-urea was obtained. HRMS (FAB$^+$) calcd $C_{14}H_{17}N_6O$ (M$^+$) 284.1386, found 284.1386.

Example 13

Preparation of 1-[7-(2,4-Dimethoxy-pyrimidin-5-yl)-imidazo[1,2-a]pyridin-2-yl]-3-ethyl-urea

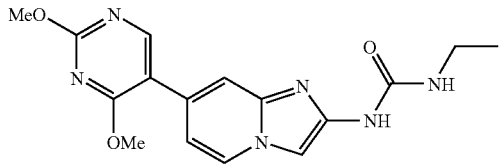

Using the general procedure of Example 8, but substituting the relevant starting material 1-[7-(2,4-Dimethoxy-pyrimidin-5-yl)-imidazo[1,2-a]pyridin-2-yl]-3-ethyl-urea was obtained. LCMS (APCI$^+$) 343.2 (100%, MH$^+$).

Example 14

Preparation of 4-[2-(3-Ethyl-ureido)-imidazo[1,2-a]pyridin-7-yl]-3,5-dimethyl-pyrazole-1-carboxylic Acid Tert-Butyl Ester

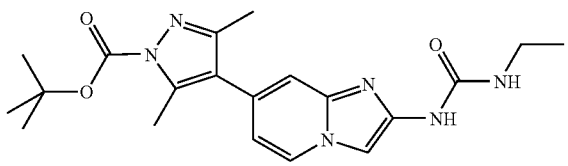

Using the general procedure of Example 8, but substituting the relevant starting material, 4-[2-(3-Ethyl-ureido)-imidazo[1,2-a]pyridin-7-yl]-3,5-dimethyl-pyrazole-1-carboxylic acid tert-butyl ester was obtained LCMS (APCI$^+$) 399.3 (100%, MH$^+$).

Example 15

Preparation of 1-Ethyl-3-[7-(1H-pyrazol-4-yl)-imidazo[1,2-a]pyridin-2-yl]-urea

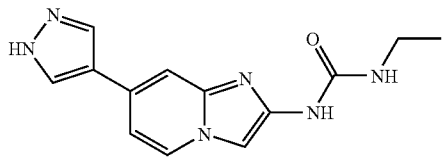

Using the general procedure of Example 8, but substituting the relevant starting material, the target compound 1-Ethyl-3-[7-(1H-pyrazol-4-yl)-imidazo[1,2-a]pyridin-2-yl]-urea was obtained. LCMS (APCI$^+$) 271.1 (100%, MH$^+$).

Example 16

Preparation of 1-(3-Chloro-7-pyridin-3-yl-imidazo[1,2-a]pyridin-2-yl)-3-ethyl-urea

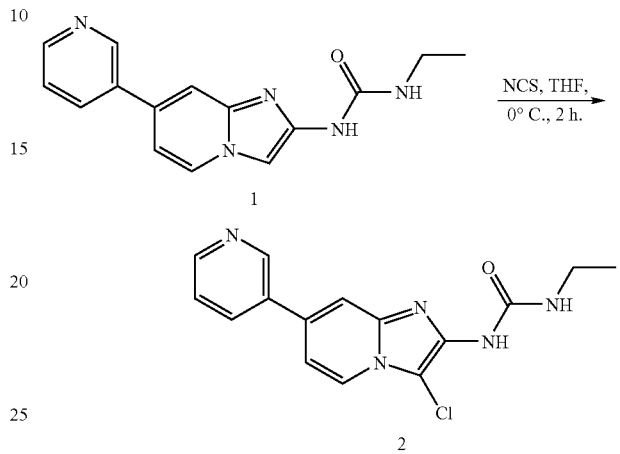

Ethyl-3-(7-pyridin-3-yl-imidazo[1,2-a]pyridin-2-yl)-urea (1) (196 mg, 0.70 mmol), prepared as in Example 1, was dissolved/suspended in tetrahydrofuran (80 mL) and cooled to 0° C., (ice/water). N-chlorosuccinimide (102 mg, 0.77 mmol) was added and the mixture stirred at 0° C. for 2 h. All solids had dissolved and the reaction was complete by LCMS after this time. The solvent was removed under reduced pressure to give a residue which was purified by chromatography on silica gel (2% methanol/dichloromethane), followed by recrystallization from ethyl acetate/methanol to afford 1-(3-chloro-7-pyridin-3-yl-imidazo[1,2-a]pyridin-2-yl)-3-ethyl-urea (2) as a solid (132 mg). HRMS (EI$^+$) calcd $C_{15}H_{14}{}^{35}ClN_5O$ (M$^+$) 315.0887, found 315.0882; calcd $C_{15}H_{14}{}^{37}ClN_5O$ (M$^+$) 317.0857, found 317.0862.

Example 17

Preparation of 1-[3-Chloro-7-(2-dimethylamino-pyrimidin-5-yl)-imidazo[1,2-a]pyridin-2-yl]-3-ethyl-urea

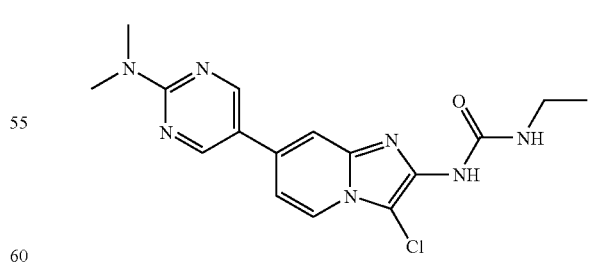

Using the general procedure of Example 16, but substituting the relevant starting material, [3-chloro-7-(2-dimethylamino-pyrimidin-5-yl)-imidazo[1,2-a]pyridin-2-yl]-3-ethyl-urea, was obtained. LCMS (APCI$^+$) 360. HRMS (EI$^+$) calcd $C_{16}H_{18}{}^{35}ClN_7O$ (M$^+$) 359.1261, found 359.1261; calcd $C_{16}H_{18}{}^{37}ClN_7O$ (M$^+$) 361.1232, found 361.1238.

Example 18

Preparation of 2-(3-Ethyl-ureido)-imidazo[1,2-a]pyridine-7-carboxylic Acid Methyl Ester

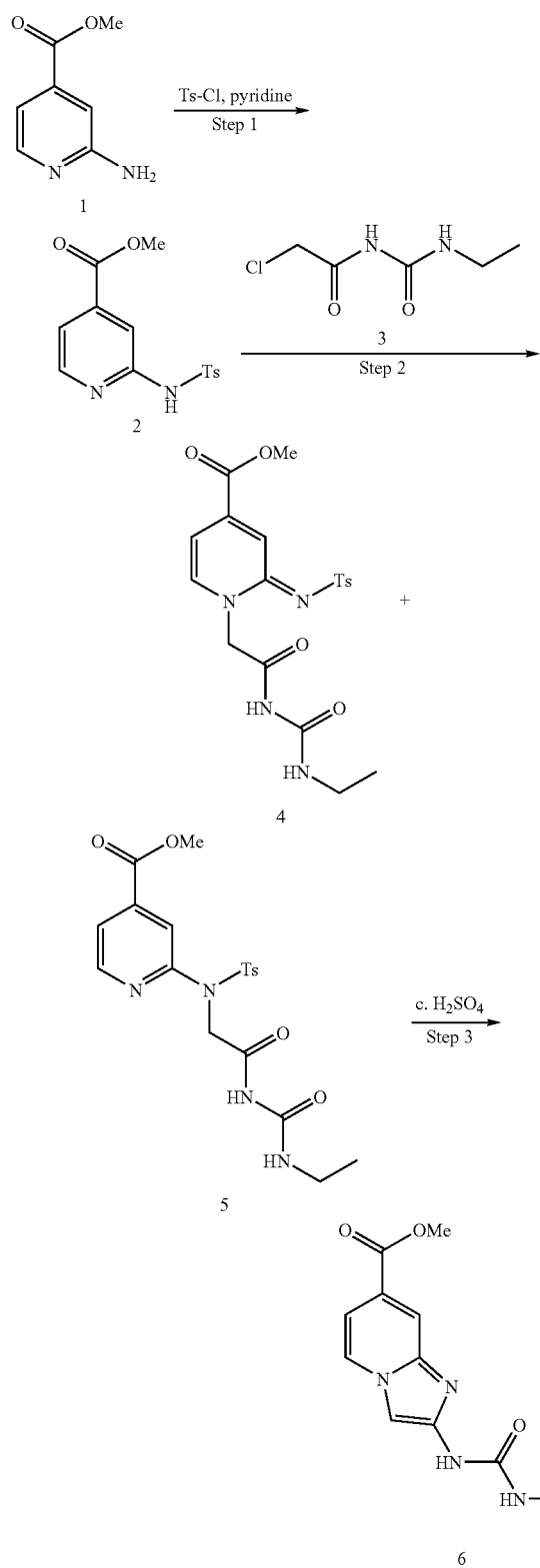

Step 1:

2-Amino-4-methoxycarbonylpyridine (9.33 g, 61.4 mmol) (1) and p-tosyl chloride (12.35 g, 65.5 mmol) were heated at 90° C. with stirring in pyridine (100 ml) for 2 hours. The solvent was then removed. Water (200 ml) was added to the residue and the resultant solid was removed by filtration and washed with water (2×50 ml) providing compound 2 (18.26 g). LCMS (APCI$^+$): 307.1 [100%].

Step 2:

Pyridine 2 (10.80 g, 65.6 mmol) and chloride 3 (18.26 g, 59.7 mmol) were dissolved in dimethyl formamide (100 ml) and diisopropylethylamine (11.4 ml, 65.6 mmol). The mixture stirred at 23° C. overnight. Dimethyl formamide was removed and the residue was dissolved in methanol (50 ml) then poured into water (400 ml). The precipitate was collected by filtration and washed with water (3×100 ml), 2:1 water:methanol (2×30 ml) then oven dried for 1 hour (110°). (22.6 g). LCMS (APCI$^+$): 435.2 [100%], 390.1 [25%], 347.1 [40%], 307.6 [35%].

Step 3:

Concentrated sulfuric acid (200 ml) was added to the above mixture (20.5 g) and stirred at 23° C. for 20 minutes. The mixture was poured onto ice (~1500 g) and made basic (pH=8) with 40% sodium hydroxide (aq). The temperature was not allowed to exceed 15° C. The precipitated product 2-(3-Ethyl-ureido)-imidazo[1,2-a]pyridine-7-carboxylic acid methyl ester (6) was collected by filtration and washed with water (500 ml), then 2:1 water:methanol (2×50 ml) followed by drying (4 hours, 110° C.). (10.27 g). (LCMS (APCI$^+$): 263.2 [100%], 192.1 [90%].

Example 19

Preparation of 2-(3-Ethyl-ureido)-imidazo[1,2-a]pyridine-7-carboxylic Acid Amide

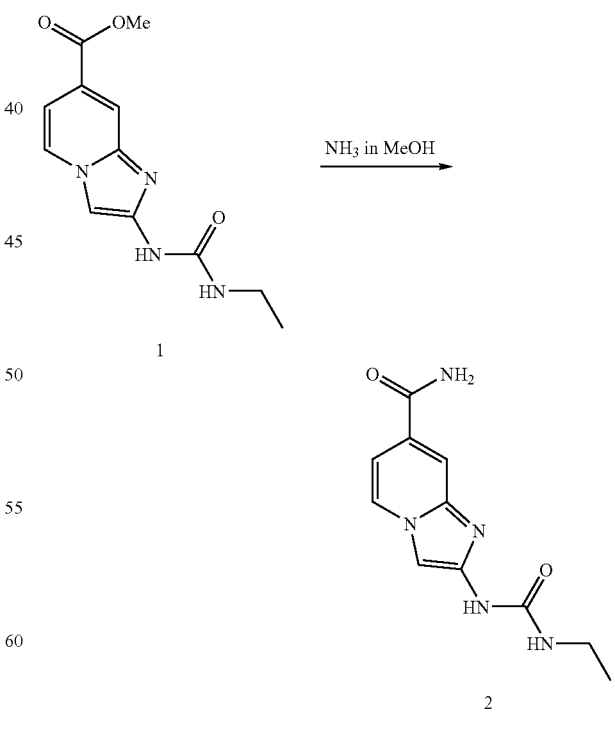

Ester 1 (0.79 g, 3.0 mmol), see Example 18, was heated in a sealed system for 4 days in ammonia methanol (7 N, 40 ml). After cooling to 23° C. the system was chilled in a freezer (−20° C.) and then filtered to give compound 2 (0.66 g). LCMS (APCI⁺): 248.2 [100%], 203.1 [30%], 177.2 [65%], 159.2 [15%]

Example 20

Preparation of 1-Ethyl-3-[7-(5-methyl-2H-[1,2,4] triazol-3-yl)-imidazo[1,2-a]pyridin-2-yl]-urea

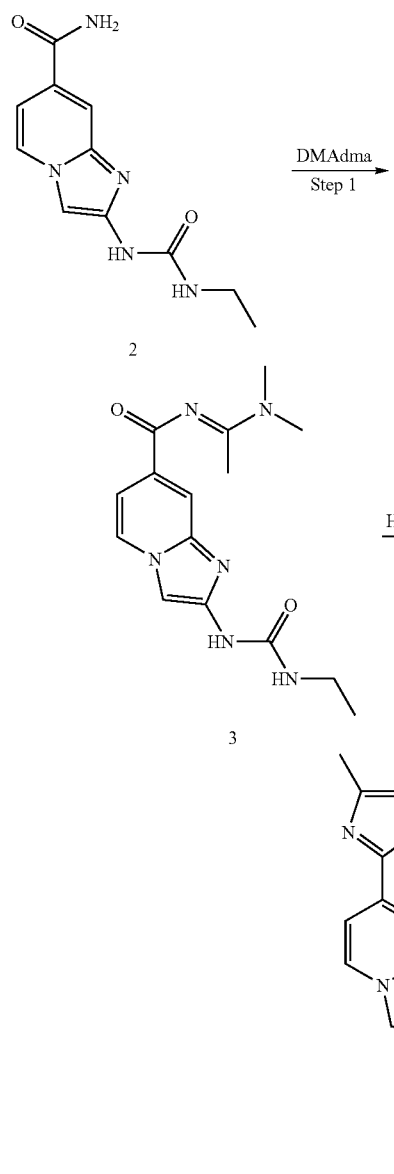

Step 1:
Dimethylacetamide dimethyl acetal (0.40 ml, 2.66 mmol) was added to 2-(3-ethyl-ureido)-imidazo[1,2-a]pyridine-7-carboxylic acid amide (as in Example 19) (0.50 g, 2.0 mmol) then suspended in hot dimethylacetamide (~90° C.) (6 ml). After 10 minutes heating was stopped and the mixture cooled to 23° C. The mixture was diluted with water (60 ml) and extracted with dichloromethane (4×15 ml). The combined extracts were then washed with water (30 ml), then brine solution (30 ml) and dried over sodium sulfate. The drying agent was removed by filtration and the resultant mixture was concentrated to provide 3 as a solid (0.58 g). LCMS (APCI⁺): 317.2 [100%]; 246.2 [30%].

Step 2:
Hydrazine hydrate (100 µL, 2.05 mmol) was added to compound 3 (290.9 mg, 0.92 mmol) dissolved in acetic acid (5 ml) and the mixture heated to 90° C. for 20 minutes. The mixture was concentrated and to the residue was added water (5 ml) and 5% potassium carbonate solution. The resulting solid was recovered by filtration and washed with water (2×5 ml) to give 1-ethyl-3-[7-(5-methyl-2H-[1,2,4]triazol-3-yl)-imidazo[1,2-a]pyridin-2-yl]-urea (4) (249 mg), which was subsequently recrystallized from dimethyl formamide/water. LCMS (APCI⁺): 286.2 [100%], 241.1 [30%], 215.2 [25%].

Example 21

Preparation of 1-[7-(1,5-Dimethyl-1H-[1,2,4]triazol-3-yl)-imidazo[1,2-a]pyridin-2-yl]-3-ethyl-urea and 1-[7-(2,5-Dimethyl-2H-[1,2,4]triazol-3-yl)-imidazo[1,2-a]pyridin-2-yl]-3-ethyl-urea

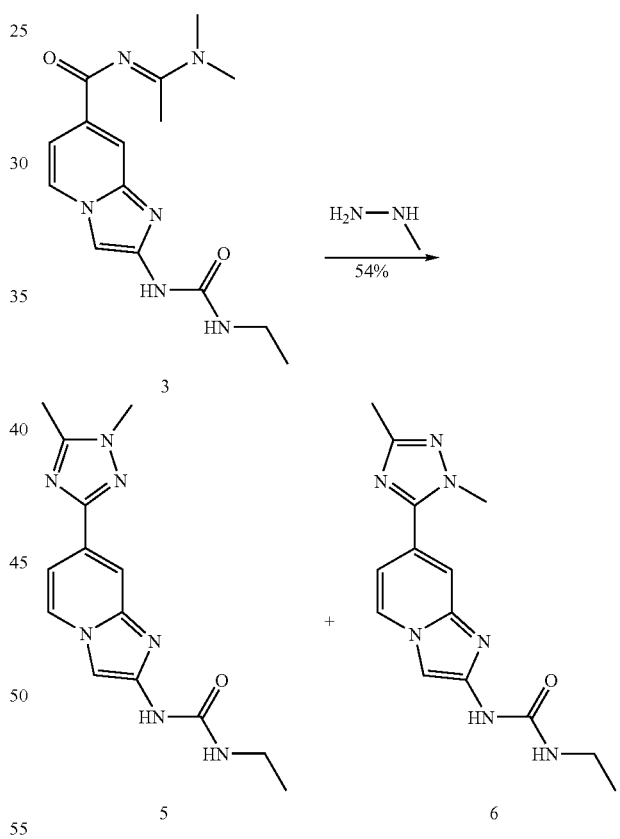

Methyl hydrazine (100 µL, 1.88 mmol) was added to compound 3, produced as in Example 20, (241.0 mg, 0.77 mmol) dissolved in acetic acid (5 ml) and the mixture heated to 90° C. for 30 minutes. The mixture was concentrated and to the residue was added water (5 ml) and 5% potassium carbonate solution. The resulting solid was recovered by filtration and washed with water (2×5 ml) to give 1-[7-(1,5-dimethyl-1H-[1,2,4]triazol-3-yl)-imidazo[1,2-a]pyridin-2-yl]-3-ethyl-urea 5 and 1-[7-(2,5-dimethyl-2H-[1,2,4]triazol-3-yl)-imidazo[1,2-a]pyridin-2-yl]-3-ethyl-urea 6 (123.6 mg). LCMS (APCI⁺): 300.2 [100%], 255.2 [25%], 229.1 [30%].

Example 22

Preparation of 1-Ethyl-3-[7-(5-methyl-[1,2,4]oxadiazol-3-yl)-imidazo[1,2-a]pyridin-2-yl]-urea

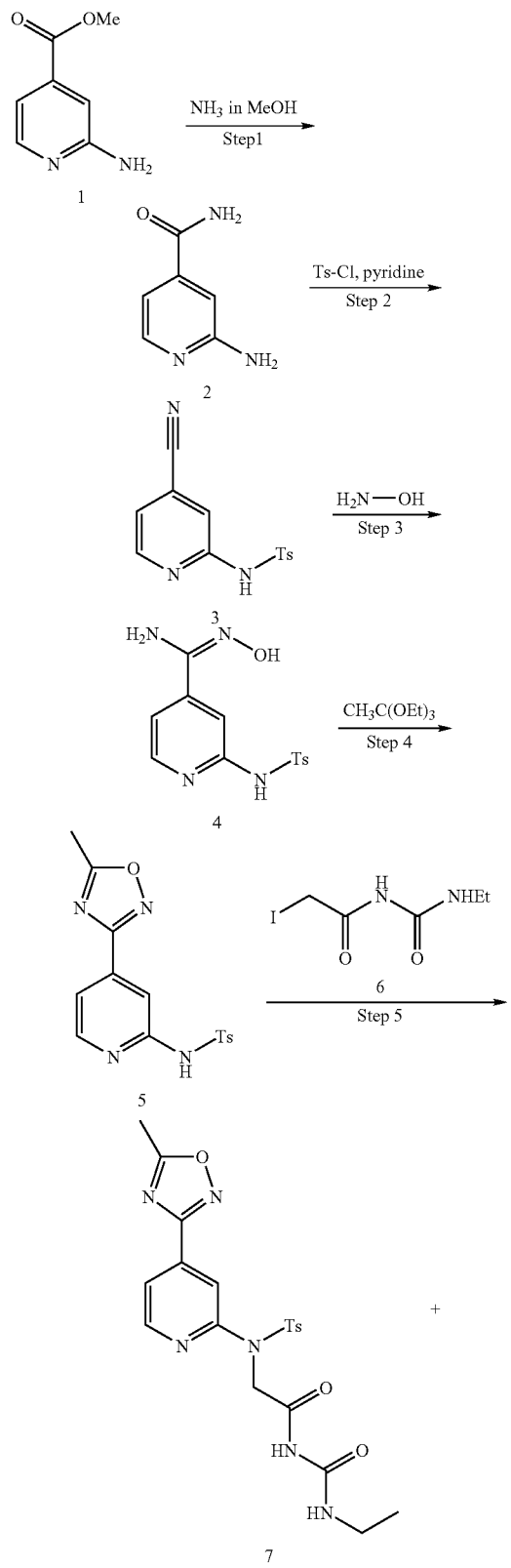

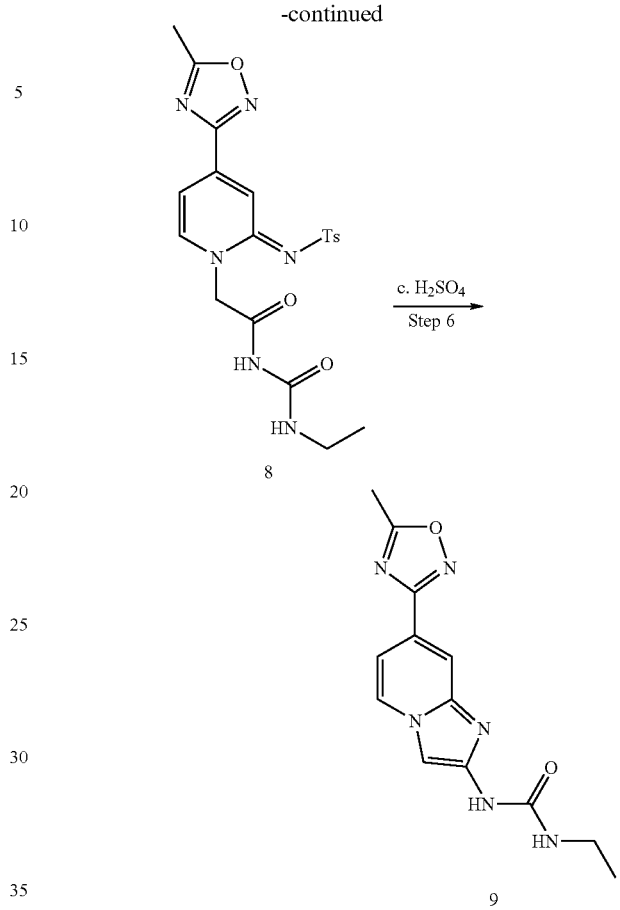

Step 1:

2-amino-4-methoxycarbonylpyridine (1) (0.77 g, 5.1 mmol) was heated overnight with stirring at 60° C. in a sealed system with ammonia methanol (7 N, 20 ml). After cooling to 23° C. the solvent was removed by rotary evaporator to give compound 2 (0.7 g). LCMS (APCI+): 138.2 [100%].

Step 2:

Compound 2 (0.70 g, 5.0 mmol) and p-tosyl chloride (2.45 g, 12.8 mmol) were heated at 90° C. overnight with stirring in pyridine solution (25 ml). Solvent was removed and the residue treated with water (50 ml). Compound 3 precipitated and was collected by filtration and washed with water (10 ml). (1.31 g). LCMS (APCI+): 274.2 [100%].

Step 3:

Hydroxylamine hydrochloride (0.55 g, 7.9 mmol) and potassium carbonate (0.55 g, 4.0 mmol) dissolved in water (10 ml) were added to compound 3 (1.00 g, 3.7 mmol) suspended in ethanol (40 ml). The mixture was heated to reflux with stirring overnight. The mixture was then concentrated and the residue treated with water (30 ml). The precipitated solid (4) collected by filtration and washed with water (2×10 ml). (1.03 g). LCMS (APCI+): 307.1 [100%].

Step 4:

Compound 4 (0.95 g, 2.65 mmol) was heated at reflux with stirring in triethylorthoacetate solution (2.5 ml) containing 2 drops of trifluoroborane diethylether complex for 1 hour. At this time another portion of triethylorthoacetate (0.5 ml) and trifluoroborane diethylether complex (2 drops) were added and the mixture was stirred for an additional 0.5 hours. Ethanol (4 ml) was then added and the mixture cooled to 23° C. overnight. The precipitated solid (5) was collected by filtration and washed with ethanol (2 ml). (0.51 g). LCMS (APCI⁺): 331.1 [100%].

Step 5:

Compound 6 (0.43 g, 1.7 mmol) was added as a solid to a suspension of compound 5 (0.50 g, 1.5 mmol) and diisopropylethylamine (0.30 ml, 1.7 mmol) in dimethyl formamide (5 ml). The mixture was stirred overnight at 23° C. The reaction mixture was concentrated and the residue taken up in methanol (2 ml) which was added to water (30 ml). The precipitated solid was collected by filtration and washed with water (2×5 ml) and water/methanol (1:1, 2×2 ml). (0.68 g). LCMS (APCI⁺): 331.1 [100%].

Step 6:

The mixture of step 5 (0.60 g) was stirred in concentrated sulfuric acid. (6 ml) until all had dissolved and then poured onto ice (~70 g) and made basic (pH=9) with 40% aqueous sodium hydroxide, maintaining the temperature below 20° C. The precipitated solid was collected by filtration and washed with water (100 ml), water/methanol (1:1, 10 ml) and methanol (5 ml) to give a solid (0.29 g). Recrystallization from dimethyl formamide gave target compound 9 as a solid (108.3 mg). LCMS (APCI⁺): 287.2 [100%], 242.1 [25%], 216.1 [40%].

Example 23

Preparation of 1-Ethyl-3-[5-(1-methyl-1H-pyrazol-4-yl)-7-pyridin-3-yl-imidazo[1,2-a]pyridin-2-yl]-urea

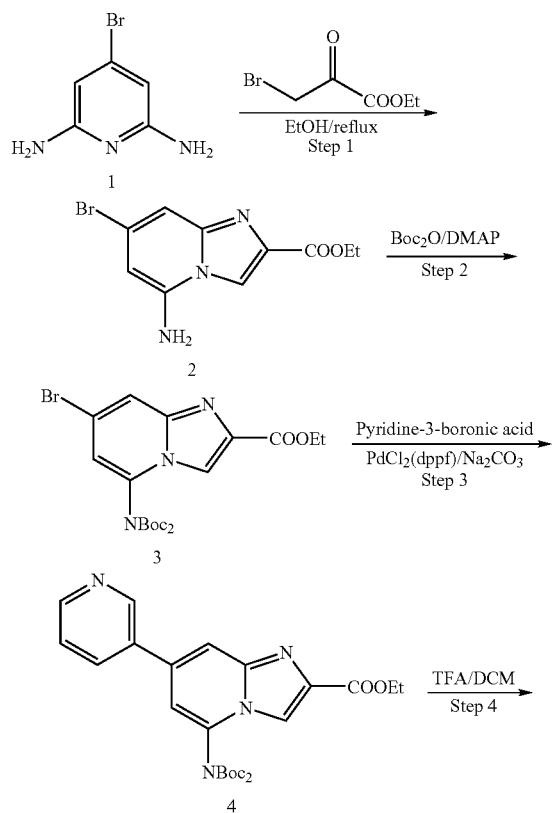

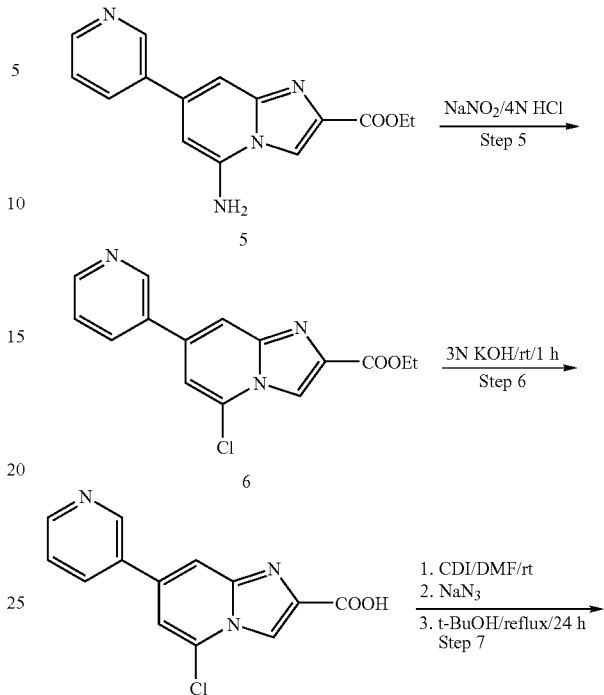

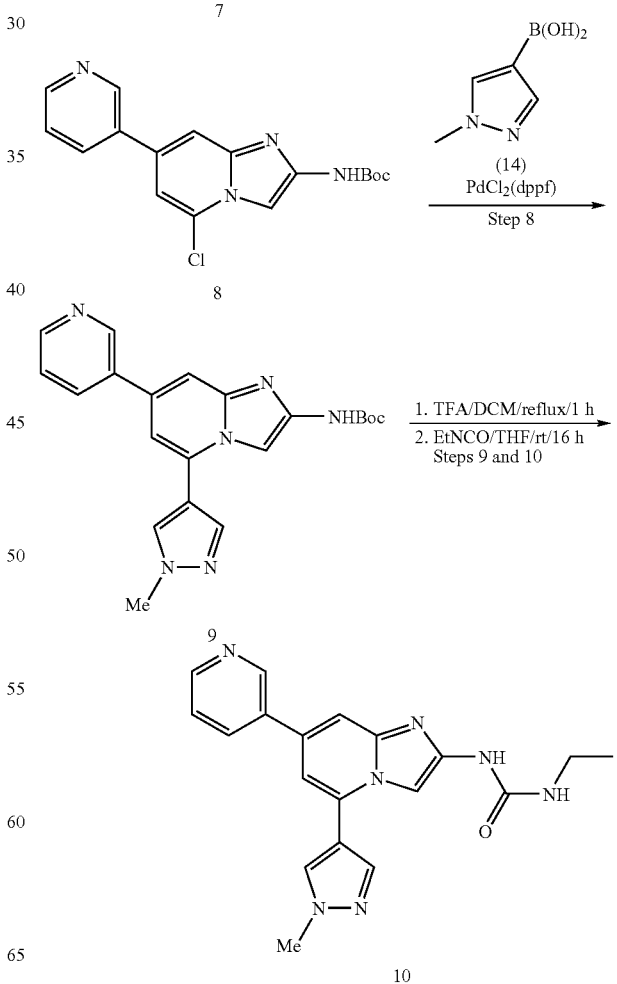

Step 1:

A solution of 4-bromo-2,4-diaminopyridine (1) (1.09 g, 5.80 mmol) and ethyl bromopyruvate (0.85 mL of 90% purity, 6.09 mmol) in ethanol (100 mL) was refluxed for 3 h. The ethanol was removed in vacuo and the residue was slurried with saturated aqueous sodium bicarbonate, then diethyl ether to provide the product (2) as a powder (1.24 g, 75%). APCI-MS Found: [M+H]$^+$=286, 284.

Step 2:

A solution of bromide (2) (1.11 g, 3.91 mmol), di-t-butyl-dicarbonate (1.87 g, 8.57 mmol) and N,N-dimethylaminopyridine (20 mg) in dry tetrahydrofuran (80 mL) was refluxed for 1 h. The solvent was removed in vacuo residue was partitioned between ethyl acetate and brine and worked up to give an oil which was chromatographed on silica. Elution with ethyl acetate/petroleum ether (1:1) gave product (3) as a viscous oil (1.31 g, 69%), which was used directly. APCI-MS Found: [M+H]$^+$=486, 484.

Steps 3 and 4:

To a suspension of the bromide (3) (8.00 g, 0.016 mol) in toluene (120 mL) was added a suspension of pyridine-3-boronic acid (3.02 g, 0.024 mol) in ethanol (30 mL) and the mixture was stirred for 5 min, by which time it was homogeneous. 2N Sodium carbonate (60 mL, 0.12 mol) was added and the mixture was purged with nitrogen. [1,1'-bis(diphenylphosphino)ferrocene]dichloropalladium II (0.26 g) was added last and the mixture was refluxed under nitrogen for 4 h. The mixture was partitioned between ethyl acetate and water and the organic layer was worked up to give crude product (4) as an oil, which was immediately deprotected. APCI-MS Found: [M+H]$^+$=483.

The product was dissolved in a mixture of dichloromethane (100 mL) and trifluoroacetic acid (50 mL) and the solution was refluxed for 1.5 h. The solvents were removed in vacuo and the residue was slurried with saturated aqueous sodium bicarbonate (200 mL) for 30 min. Diethyl ether (200 mL) was added and the mixture was slurried for a further 30 min and filtered. The solid was washed with several portions of diethyl ether and dried, to give product (5) as a powder (3.74 g, 83%), sufficiently pure for the next step. APCI-MS Found: [M+H]$^+$=283.

Step 5:

A mixture of finely powdered amine (5) (4.00 g, 0.014 mol) and 4 N hydrogen chloride (400 mL) was stirred vigorously at 23° C. for 30 min, by which time the hydrochloride salt had precipitated out as a yellow solid. The mixture was cooled to 5° C. and a solution of sodium nitrite (1.46 g, 0.021 mol) in water (5 mL) was added drop wise. The mixture was stirred at this temperature for 30 min, then urea (0.59 g, 9.91 mmol) was added. The mixture was stirred at 23° C. for a further 1 h, then basified by portion wise addition of solid sodium bicarbonate. ethyl acetate was added and the mixture was stirred vigorously for 30 min, then filtered through Celite to remove insoluble black material. The ethyl acetate layer was worked up, adsorbed onto silica and chromatographed. Ethyl acetate eluted foreruns, while ethyl acetate/methanol (95:5) gave the chloride (6) as a solid (1.21 g). APCI-MS Found: [M+H]$^+$=304, 302.

Step 6:

To a solution of ester (6) (0.43 g, 1.41 mmol) in ethanol (40 mL) was added 3N potassium hydroxide (10 mL) and the solution was stirred at 23° C. for 3 h. After careful adjustment of the pH to 4 with conc. hydrogen chloride the solution was concentrated to dryness. The residue was triturated with three 30 mL portions of methanol, filtered and the combined triturates were concentrated to dryness, leaving crude acid (7) as a white solid (0.55 g), contaminated with some salt. This material was used as such in the next step. APCI-MS Found: [M−H]$^-$=274, 272.

Step 7:

To a solution of the crude acid (7) (0.55 g, 2.00 mmol) from step 6, and N,N-dimethylaminopyridine (ca. 5 mg) in dry dimethyl formamide (30 mL) was added N,N-carbonyldiimidazole (0.49 g, 3.00 mmol) and the solution was stirred at 23° C. for 15 min. A solution of sodium azide (2 g) in water (10 mL) was added and the mixture was stirred vigorously for 30 min and then diluted with brine. The mixture was extracted with ethyl acetate and the extract washed well with brine, then worked up to give crude acyl azide as a cream solid. This was dissolved immediately in dry t-butanol and refluxed under nitrogen for 8 h. Removal of the solvent in vacuo gave a solid which was adsorbed onto silica and chromatographed. Elution with ethyl acetate/methanol (92:8) gave the product (8) as a white solid (0.38 g, 78% overall from ester (6)). APCI-MS Found: [M+H]$^+$=347, 345.

Step 8:

To a suspension of the chloride (8) (0.18 g, 0.52 mmol) in toluene (20 mL) was added a suspension of pyrazole-boronic (14) acid (0.16 g, 0.78 mmol) in ethanol (4 mL) and the mixture was stirred for 5 min, by which time it was homogeneous. 2N Sodium carbonate (2 mL, 4.0 mmol) was added and the mixture was purged with nitrogen. [1,1'-bis(diphenylphosphino)ferrocene]dichloropalladium 1 (20 mg) was added last and the mixture was refluxed under nitrogen for 24 h. The mixture was partitioned between ethyl acetate and water and the organic layer was worked up to give crude product (9) as an oil, which was adsorbed onto silica and chromatographed. Elution with ethyl acetate/methanol (95:5) gave foreruns, while ethyl acetate/methanol (9:1) eluted the product (9) as a white solid (0.10 g, 49%). APCI-MS Found: [M+H]$^+$=391.

Steps 9 and 10:

A solution of (9) (0.10 g, 0.26 mmol) in a mixture of dichloromethane (10 mL) and trifluoroacetic acid (10 mL) was refluxed for 1 h and the solvents removed in vacuo. The residue was treated with saturated aqueous sodium bicarbonate, and extracted 6 times with ethyl acetate. The combined extract was worked up to give crude amine (10) as a yellow solid, which was used directly. APCI-MS Found: [M+H]$^+$=291.

The amine (10) was dissolved in dry tetrahydrofuran (25 mL), ethyl isocyanate (0.11 mL, 1.39 mmol) was added and the solution was stirred at 23° C. for 72 h. The product was adsorbed directly onto silica by concentration in vacuo and chromatographed. Elution with ethyl acetate/methanol (9:1) gave foreruns while ethyl acetate/methanol (85:15) eluted product (11) as a yellow solid. Crystallization from tetrahydrofuran/methanol/petroleum ether gave pure material (14 mg). APCI-MS Found: [M+H]$^+$=362.

Example 24

Preparation of 2-(3-Ethyl-ureido)-imidazo[1,2-a]pyridine-7-carboxylic Acid

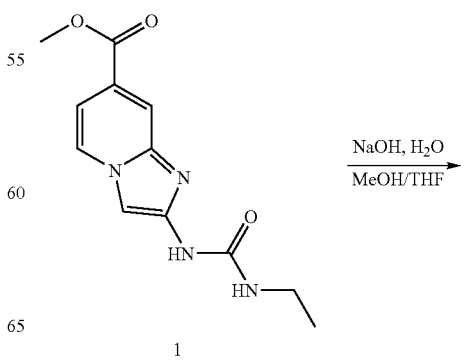

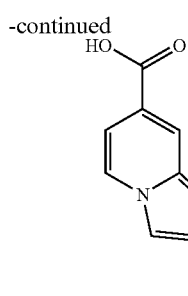

2

Step 1:

Compound 1, prepared as in Example 18, (2.62 g, 10 mmol) was stirred at 23° C. for 6 hours in a mixture of 1 N sodium hydroxide/methanol/tetrahydrofuran (100 mL of a 1:2:2 mixture). The reaction mixture was concentrated and the resultant residue was treated with 1N hydrogen chloride (25 ml) and water (10 ml). The precipitated solid was collected by filtration, washed with water (3×10 ml) and oven dried (110° C.). Recrystallization from dimethyl formamide/water gives the target compound (2) as a powder (2.38 g). LCMS (APCI$^+$): 249.2 [100%], 204.1 [20%], 178.2 [45%].

Example 25

Preparation of 1-[7-(3,5-Dimethyl-1H-pyrazol-4-yl)-imidazo[1,2-a]pyridin-2-yl]-3-ethyl-urea

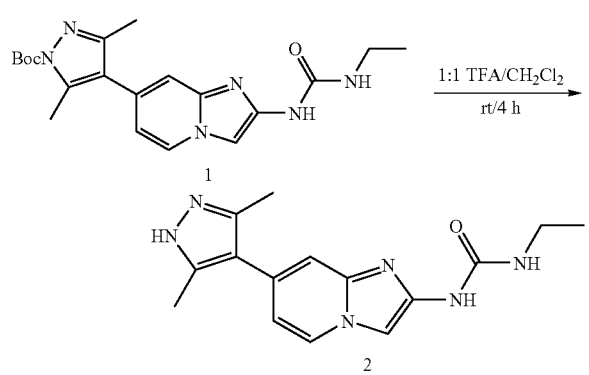

Step 1:

To a solution of Compound (1), prepared as in Example 14, (83 mg, 0.208 mmol) in dry dichloromethane (10 mL) was added trifluoroacetic acid (10 mL), and the mixture was stirred at 23° C. for 4 h. The solvents were removed and the residue was treated with a mixture of ice and aqueous sodium bicarbonate (50 mL). The mixture was extracted with ethyl acetate (6×50 mL) and the combined extracts were concentrated under reduced pressure. The crude product was purified by column chromatography on silica gel (dichloromethane gradient to 5% methanol/dichloromethane), to give the target compound (2) (51 mg). LCMS (APCI$^+$) 299.2 (100%, MH$^+$).

Example 26

Preparation of 1-Ethyl-3-[7-(piperidine-1-carbonyl)-imidazo[1,2-a]pyridin-2-yl]-urea

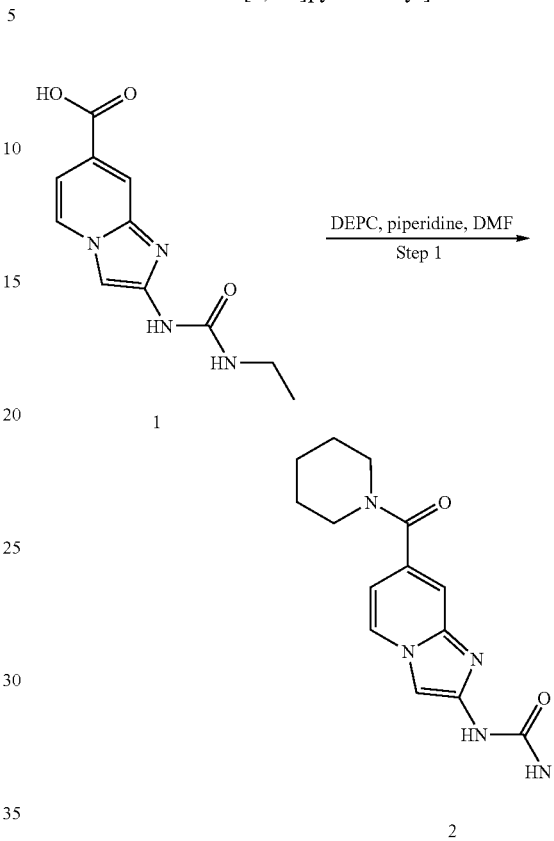

Diethyl pyrocarbonate, DEPC, (0.17 ml, 0.97 mmol) was added by syringe to a suspension of compound (1), prepared as in Example 24, (218.3 mg, 0.88 mmol) and piperidine (0.18 ml, 2.45 mmol) in dimethylformamide (10 ml). The mixture was stirred overnight at 23° C. The reaction mixture was concentrated then triturated with ethyl acetate. Compound (2) was recovered by filtration and washed with ethyl acetate (1 ml) and hexane (2 ml) (255.5 mg). LCMS (APCI$^+$): 316.2 [100%], 271.2 [10%], 245.3 [35%].

Example 27

Preparation of 1-Cyclopropyl-3-(7-pyrimidin-5-yl-imidazo[1,2-a]pyridin-2-yl)-urea

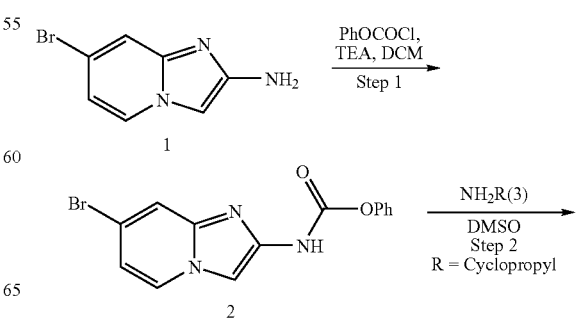

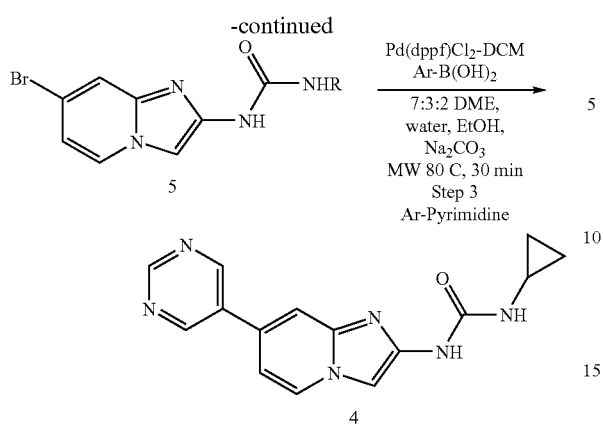

Step 1:
To a solution of 1 (7.2 g, 23 mmol) in 50 mL dichloromethane and 5 mL triethylamine at 23° C. under a nitrogen atmosphere was added phenylchloroformate (5.0 g, 32 mmol) drop wise. After 18 hours the reaction was diluted with diethylether (150 mL) and the precipitated product was collected by filtration, washed with water (50 mL) and dried under vacuum to give 2 (5.0 g). MS (APCI)=332.0, 334.0 [M+H]

Step 2:
To a suspension of 2 (0.5 g, 1.5 mmol) in dimethylsulfoxide (5 mL) at 23° C. under a nitrogen atmosphere was added an amine 3 (7.2 mmol) The reaction was heated to 80° C. until it became homogenous. The reaction was then diluted to 30 mL total volume with water and the precipitated product was collected by vacuum filtration, washed twice with water (10 mL), diethyl ether (2×10 mL) and dried under vacuum to give the urea products 5 that were used crude in Step 3.

Step 3:
A suspension of 5 (0.76 mmol), pyrimidine-5-boronic acid (0.105 g, 0.85 mmol), sodium carbonate (0.292 g, 2.75 mmol), and [1,1'-Bis(diphenylphosphino)ferrocene]dichloropalladium(II) complex with dichloromethane (0.007 g, 8.6 μmol) in 6 mL of 7:3:2 dimethoxyethane/water/ethanol was heated for 30 minutes at 80° C. in a CEM microwave reactor. The reaction was acidified with 2 mL glacial acetic acid and evaporated in vacuo. The residue was purified by silica gel chromatography (gradient elution 0-50% isopropanol in dichloromethane) to give the target compound (4). MS (APCI)=295.1 [M+H].

Example 28

Preparation of 1-Cyclopropylmethyl-3-(7-pyrimidin-5-yl-imidazo[1,2-a]pyridin-2-yl)-urea

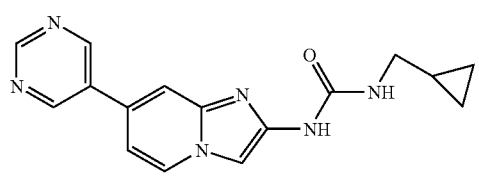

The compound was obtained using the method of Example 27 but substituting aminomethylcyclopropane in step 2. MS (APCI)=309.3 [M+H].

Example 29

Preparation of 1-Propyl-3-(7-pyrimidin-5-yl-imidazo[1,2-a]pyridin-2-yl)-urea

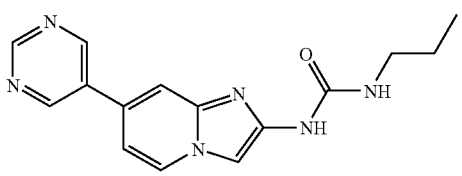

The compound was obtained using the method of Example 27 but substituting n-propylamine in step 2. MS (APCI)=297.1 [M+H].

Example 30

Preparation of 1-Isopropyl-3-(7-pyrimidin-5-yl-imidazo[1,2-a]pyridin-2-yl)-urea

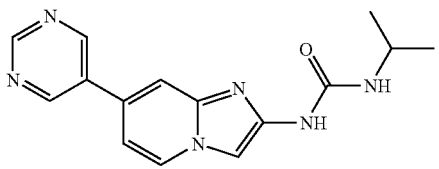

The compound was obtained using the method of Example 27 but substituting isopropylamine in step 2. MS (APCI)=297.1 [M+H].

Example 31

Preparation of 1-(7-Pyrimidin-5-yl-imidazo[1,2-a]pyridin-2-yl)-3-(2,2,2-trifluoro-ethyl)-urea

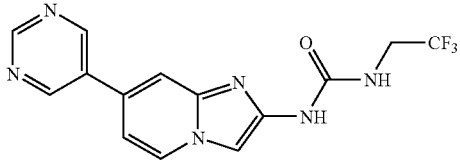

The compound was obtained using the method of Example 27 but substituting (2,2,2-trifluoroethylamine hydrochloride (7.2 mmol) and triethylamine (1 mL, 7.2 mmol) in step 2. MS (APCI)=337.1 [M+H].

Example 32

Preparation of 1-(2-Methoxy-ethyl)-3-(7-pyrimidin-5-yl-imidazo[1,2-a]pyridin-2-yl)-urea

53

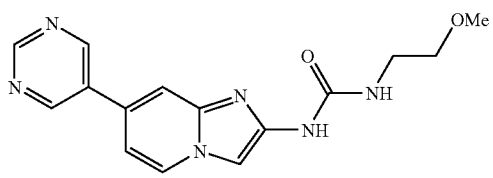

The compound was obtained using the method of Example 27, but substituting 2-methoxyethylamine in step 2. MS (APCI)=285.0 [M+H].

Example 33

Preparation of 1-Cyclobutyl-3-(7-pyrimidin-5-yl-imidazo[1,2-a]pyridin-2-yl)-urea

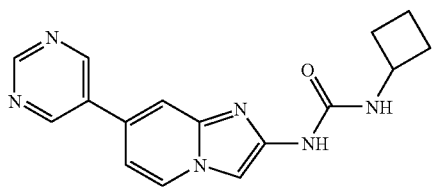

The compound was obtained using the method of Example 27 but substituting cyclobutylamine in step 2. MS (APCI)= 309.1 [M+H]. SN 29659.00

Example 34

Preparation of 1-[7-(6-Amino-pyridin-3-yl)-imidazo[1,2-a]pyridin-2-yl]-3-ethyl-urea

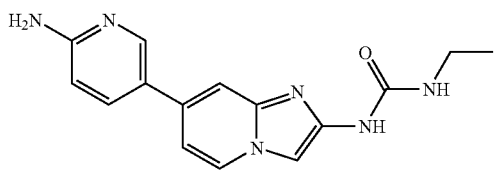

Using the general procedure of Example 8, but substituting 2-amino-5-(4,4,5,5-tetramethyl-1,3,2-dioxaborolan-2-yl) pyridine as the relevant starting material, 1-[7-(6-Amino-pyridin-3-yl)-imidazo[1,2-a]pyridin-2-yl]-3-ethyl-urea was obtained. HRFABMS Calcd for $C_{15}H_{17}N_6O$ m/z (MH$^+$) 297.14638. Found 297.14667.

Example 35

Preparation of N-(7-acetylimidazo[1,2-a]pyridin-2-yl)-N'-ethylurea

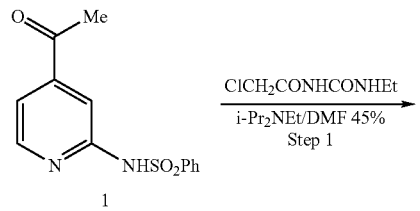

54

-continued

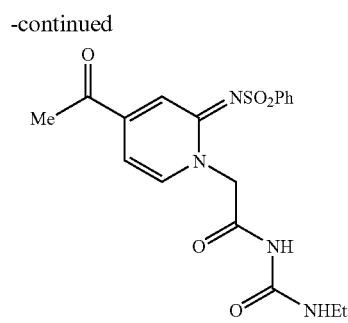

Step 1:

A mixture of 0.276 g (1 mmol) of compound (1), 0.25 g (1.5 mmol) of N-(chloroacetyl)-N'-ethylurea and 0.26 g (2 mmol) N-ethyldiisopropylamine in 5 mL dry DMF ("dimethylformamide") was stirred at room temperature overnight. The mixture was diluted with water and extracted with EtOAc to give an oil which was triturated with methanol to give 0.183 g of (2) as a white solid.

Step 2:

Compound (2) (130 mg, 0.32 mmol) was dissolved in 5 mL conc. $H_2SO_4$ at room temperature and after 5 min the solution was diluted with ice-water and neutralized with aqueous ammonia to give 51 mg of the target compound, N-(7-acetyl-imidazo[1,2-a]pyridin-2-yl)-N'-ethylurea (3). LCMS (APCI$^+$) 247.2 (100%, MH$^+$).

Example 36

Preparation of 1-Ethyl-3-[7-(5-methyl-[1,3,4]oxadiazol-2-yl)-imidazo[1,2-a]pyridin-2-yl]-urea

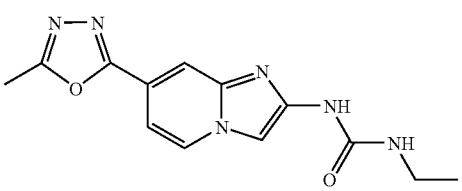

Using the general procedure of Example 35, but substituting N-[4-(5-methyl-[1,3,4]oxadiazol-2-yl)-pyridin-2-yl]-benzenesulfonamide as the relevant starting material, 1-ethyl-3-[7-(5-methyl-[1,3,4]oxadiazol-2-yl)-imidazo[1,2- a]pyridin-2-yl]-urea was obtained. Recrystallization from DMF/H$_2$O gave the compound as a tan solid. LCMS (APCI$^+$): 287.1.

Example 37

Preparation of {4-[2-(3-Ethyl-ureido)-imidazo[1,2-a]pyridin-7-yl]-pyridin-2-yl}-carbamic Acid Tert-Butyl Ester

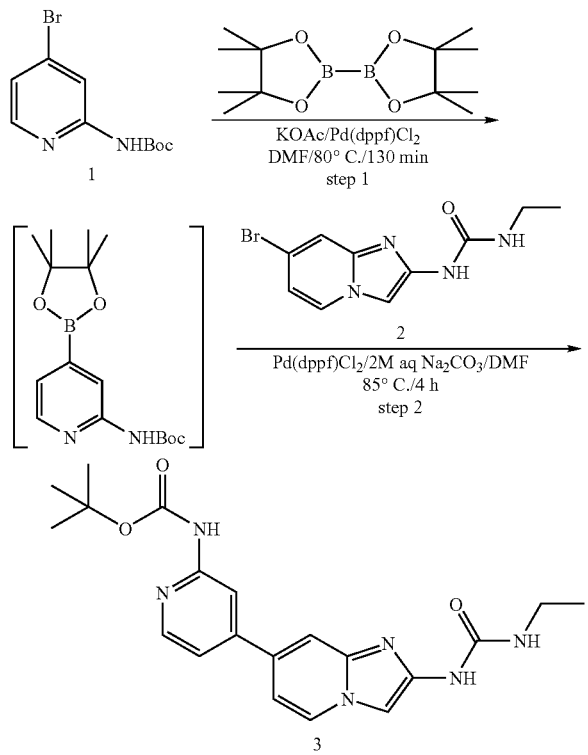

Steps 1 and 2:

To a mixture of compound 1 (301 mg, 1.10 mmol), bis(pinacolato)diboron (309 mg, 1.22 mmol), potassium acetate (356 mg, 3.63 mmol) and [1,1'-bis(diphenylphosphino)ferrocene]dichloropalladium II (48.0 mg, 0.0656 mmol), degassed and sealed under nitrogen, was added dry dimethylformamide (7.5 mL). Following further nitrogen purging, the mixture was stirred at 80° C. for 130 min. After cooling to room temperature, compound 2 (208 mg, 0.734 mmol), [1,1'-bis(diphenylphosphino)ferrocene]dichloropalladium 1 (48.2 mg, 0.0659 mmol) and 2M aqueous sodium carbonate (2.75 mL, 5.5 mmol) were added, and then the mixture was degassed, sealed under nitrogen, and stirred at 85° C. for 4 h. After cooling to room temperature, the reaction mixture was added to aqueous sodium bicarbonate (100 mL) and extracted with ethyl acetate (2×100 mL), 10% methanol in dichloromethane (3×100 mL), and then further ethyl acetate (3×100 mL). The combined extracts were concentrated under reduced pressure. The crude product was purified by silica gel chromatography (gradient elution 100% dichloromethane to 2.5% methanol/dichloromethane) to provide (3) {4-[2-(3-Ethyl-ureido)-imidazo[1,2-a]pyridin-7-yl]-pyridin-2-yl}-carbamic acid tert-butyl ester (122 mg). (MeOH/CH$_2$Cl$_2$/hexane) LCMS (APCI$^+$) 397.2 (100%, MH$^+$).

Example 38

Preparation of 1-Ethyl-3-[7-(2H-pyrazol-3-yl)-imidazo[1,2-a]pyridin-2-yl]-urea

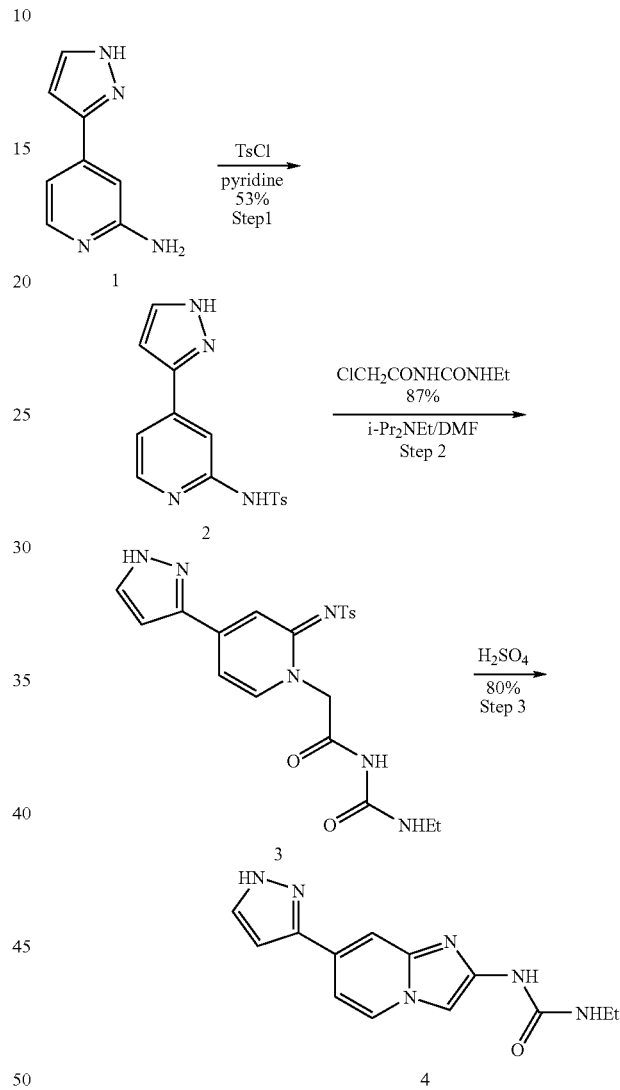

Step 1:

A mixture of (1) (0.49 g, 2.5 mmol), p-toluenesulfonyl chloride (0.58 g, 3 mmol) and Et$_3$N (250 mg, 3 mmol) in pyridine (10 mL) was heated to reflux overnight. After cooling, water was added and the pyridine was removed under vacuum to give 0.41 g of (2).

Step 2:

A mixture of compound (2) (0.4 g, 1.27 mmol), N-(chloroacetyl)-N'-ethylurea (0.3 g, 1.8 mmol) and N-ethyldiisopropylamine (0.33 g, 2.5 mmol) in dry DMF ("dimethylformamide") (5 mL) was stirred at room temperature overnight. The mixture was diluted with water to give 0.49 g of (3) as a solid.

Step 3:

Compound (3) (0.49 g, 1.1 mmol) was dissolved in conc. H₂SO₄ (5 mL) at room temperature and after 5 min the solution was diluted with ice-water and neutralized with aqueous ammonia to give the target compound (0.24 g), (4). Mp (MeOH) 292-295° C. (decomp); LCMS (APCI+) 271.2 (100%, MH+). Anal. Calcd for C13H14N6O.0.25H2O: C, 56.82; H, 5.32; N, 30.58. Found: C, 57.00; H, 5.20; N, 30.23%.

Example 39

Preparation of 1-Ethyl-3-(7-[1,2,3]thiadiazol-4-yl-imidazo[1,2-a]pyridin-2-yl)-urea

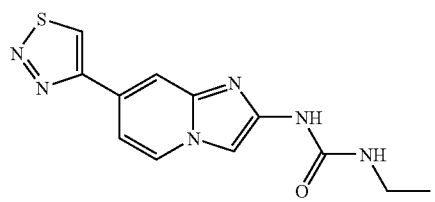

Using the general procedure of Example 35, but substituting N-(4-[1,2,3]thiadiazol-4-yl-pyridin-2-yl)-benzenesulfonamide and 1-ethyl-3-(2-iodo-acetyl)-urea as the relevant starting materials, 1-ethyl-3-(7-[1,2,3]thiadiazol-4-yl-imidazo[1,2-a]pyridin-2-yl)-urea ester was obtained. Recrystallization from DMF/H₂O gave the desired compound. LCMS (APCI⁺): 289.1.

Example 40

Preparation of 1-Ethyl-3-[7-(5-isopropyl-[1,2,4]oxadiazol-3-yl)-imidazo[1,2-a]pyridin-2-yl]-urea

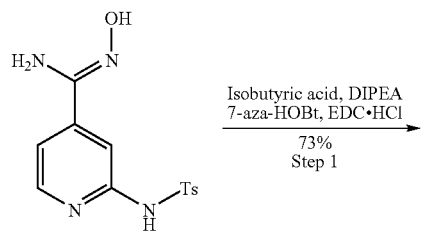

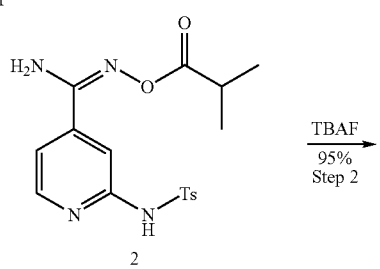

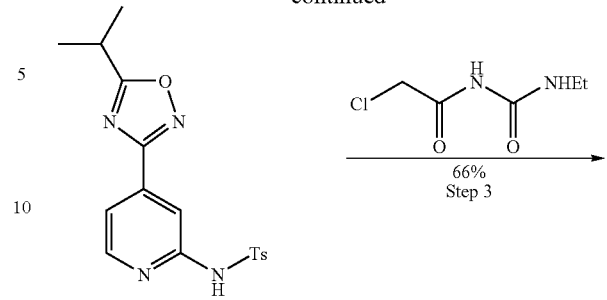

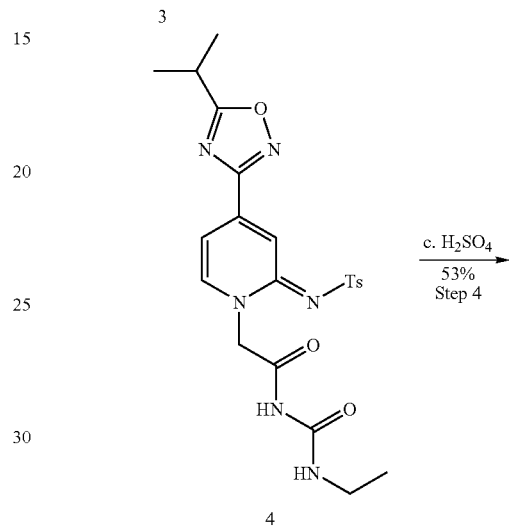

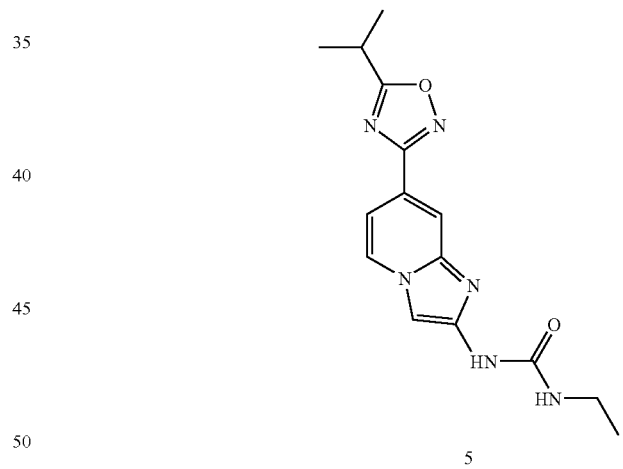

Step 1:

1-Hydroxy-7-azabenzotriazole (1.55 mL, 0.5-0.7 M solution in DMF) and then DIPEA (diisopropylethylamine) (0.50 mL, 2.4 mmol) were added to compound 1 (284.3 mg, 0.93 mmol), isobutyric acid (78 μL, 0.84 mmol), EDC.HCl ("(3-Dimethylamino-propyl)-ethyl-carbodiimide hydrochloride") (182.0 mg, 0.93 mmol) in dry DCM ("dichloromethane") (12 mL) and the mixture stirred overnight at RT. The concentrated then diluted with EtOAc (75 mL), washed with 0.2 N aq. HCl (10 mL), water (10 mL), K₂CO₃ solution (2.5% aq., 10 mL), brine (10 mL), then dried over Na₂SO₄. The mixture was filtered then concentrated to provide compound 2 as a solid.

Step 2:

TBAF ("tetra-n-butyl ammonium fluoride") (1.0 M in THF, 1.25 mL) was added to compound 2 (231.1, 0.61 mmol) dissolved in dry THF (10 mL) and the mixture stirred at reflux for one hour. The mixture was cooled to RT and diluted with EtOAc (60 mL). The solution was washed with 0.2 N aq. HCl (10 mL), water (10 mL), brine (10 mL), dried over $Na_2SO_4$ and concentrated. The residue was purified by silica gel flash column chromatography (eluted with 30% EtOAc/hexanes to give compound 3 as a colorless solid.

Step 3:

$NEt_3$ (0.20 mL, 1.44 mmol) and then 1-(2-chloro-acetyl)-3-ethyl-urea (121.8 mg, 0.74 mmol) were added to compound 3 (210.7 mg, 0.59 mmol) dissolved in DMF (4 mL) and the mixture stirred three days at RT. The mixture was concentrated and the residue was treated with MeOH (1 mL) and then water (20 mL). The precipitated solid was filtered off, washed with water and dried to yield compound 4, 186.6 mg.

Step 4

The product of step 3, (186.6 mg) was stirred in c. $H_2SO_4$ (3 mL) until all had dissolved and then poured onto ice (~50 g) and made basic (pH=9) with 40% aqueous NaOH, maintaining the temperature below 20° C. The precipitated solid was collected by filtration and washed with $H_2O$ (2×5 mL) and oven dried (64.0 mg, 53%). Recrystallization from DMF/$H_2O$ gave pure 5 as a colorless solid (45.0 mg). LCMS ($APCI^+$): 315.2.

Example 41

Preparation of 1-Ethyl-3-[7-(5-oxo-4,5-dihydro-[1,2,4]oxadiazol-3-yl)-imidazo[1,2-a]pyridin-2-yl]-urea

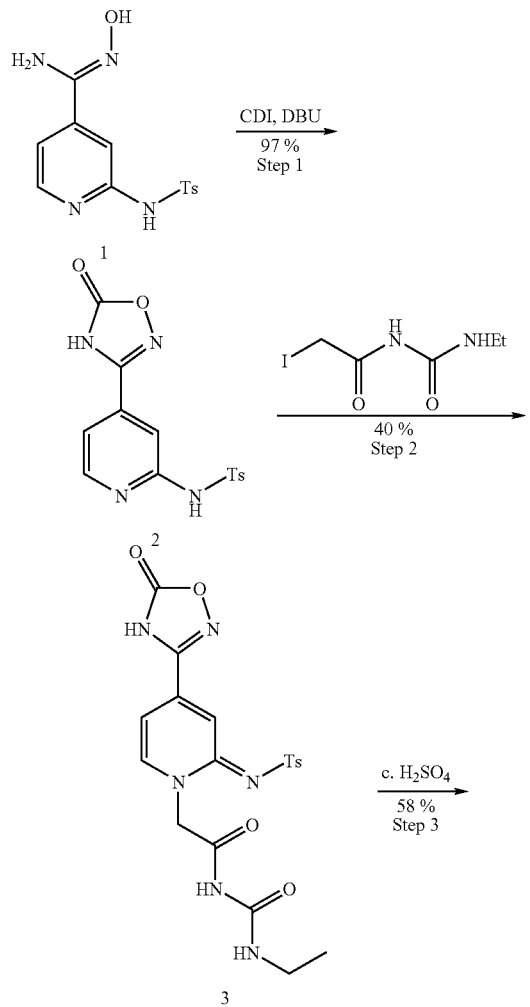

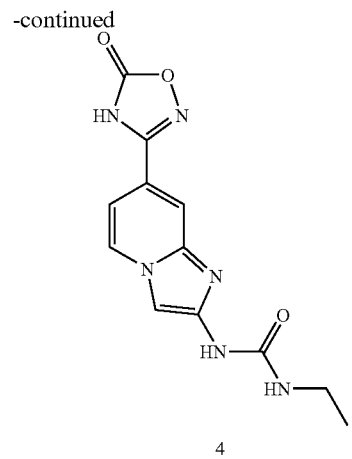

Step 1:

DBU ("1,8-diazabicyclo[5.4.0]undec-7-ene") (0.25 mL, 1.7 mmol) and CDI ("carbonyldiimidazole") (0.18 g, 1.1 mmol) were added to compound 1 (prepared as in Example 22) (0.26 g, 0.9 mmol) dissolved in THF ("tetrahydroduran") & ACN (acetonitrile") (1:1, 14 mL) and the mixture stirred at RT overnight. The solution was then diluted with EtOAc (100 mL), washed with 0.25 N aq. HCl (2×20 mL), water (20 mL), brine (20 mL), dried over $Na_2SO_4$ and concentrated to dryness to yield compound 2.

Step 2:

DIPEA (0.15 mL, 0.86 mmol) and then 1-ethyl-3-(2-iodo-acetyl)urea (239.7 mg, 0.94 mmol) were added to compound 2 (266.7 mg, 0.80 mmol) dissolved in DMF (4 mL) and the mixture stirred overnight at RT. The reaction mixture was diluted with water (70 mL) and extracted with DCM (5×15 mL). The aqueous layer was added to brine (40 mL) and concentrated to near saturation by rotary evaporation. After standing overnight a precipitate had developed and was filtered off, washed with water and dried to yield 3.

Step 3:

Concentrated $H_2SO_4$ (2 mL) was added to compound 3 (149.3 mg, mmol) and the mixture stirred until all had dissolved. The mixture was then poured onto ice (~40 g) and made basic (pH=11) with 40% aq. NaOH, maintaining the temperature below 20° C. The mixture was then re-acidified to precipitate solid 4 collected by filtration and washed with $H_2O$ (5×2 mL). Yield 55.7 mg. LCMS ($APCI^+$): 289.2.

Example 42

Preparation of {4-[2-(3-Ethyl-ureido)-imidazo[1,2-a]pyridin-7-yl]-pyridin-2-yl}-carbamic Acid Tert-Butyl Ester

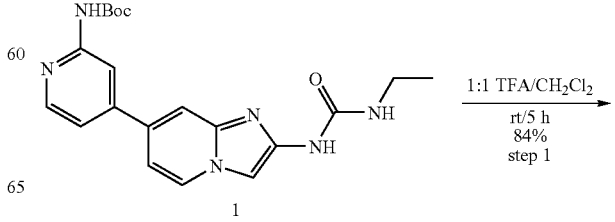

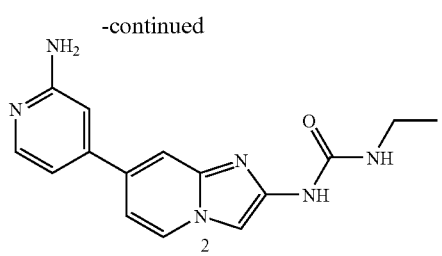

Step 1:
Compound 1, prepared as in Example 37, (145 mg, 0.366 mmol) in dry dichloromethane (15 mL) was treated with trifluoroacetic acid (15 mL) and stirred at room temperature for 5 h. The mixture was concentrated and the residue was treated with a mixture of ice and aqueous sodium bicarbonate (50 mL) and extracted with 10% methanol in dichloromethane (5×50 mL), followed by dilution with ethyl acetate (8×50 mL). Concentration under reduced pressure yielded the crude product which was purified by silica gel column chromatography (dichloromethane gradient to 5% methanol in dichloromethane) to give compound 2 (91 mg) as a yellow solid. LCMS (APCI$^+$) 297.2.

Example 43

Preparation of 1-Ethyl-3-[7-(morpholine-4-carbonyl)-imidazo[1,2-a]pyridin-2-yl]-urea

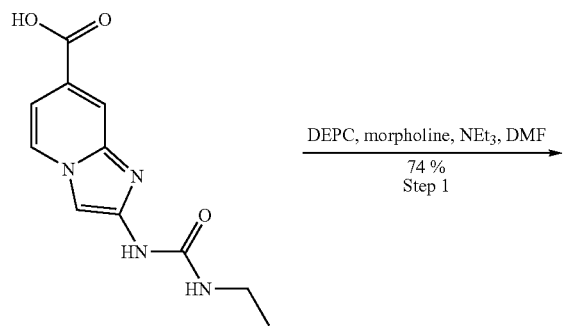

Step 1:
Diethyl phosphoryl cyanide (DEPC) (0.17 ml, 1.12 mmol) was added to a suspension of Compound 1 (prepared as in Example 24) (177.6 mg, 0.72 mmol), NEt$_3$ (0.10 ml, 0.72 mmol) and morpholine (0.13 ml, 1.49 mmol) in DMF (5 ml) and the mixture stirred overnight at RT. The mixture was concentrated to yield the crude product which was purified by alumina column chromatography (EtOAc gradient to 10% MeOH in EtOAc) to yield compound 2 (167.4 mg) LCMS (APCI$^+$): 318.2.

Example 44

Preparation of 1-Ethyl-3-[7-(2-methoxy-pyridin-4-yl)-imidazo[1,2-a]pyridin-2-yl]-urea

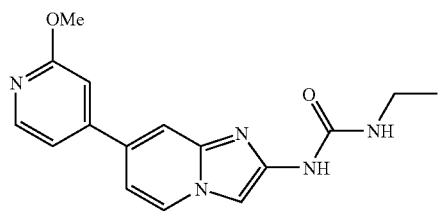

Using the general procedure of Example 37, but substituting 4-bromo-2-methoxy-pyridine as the relevant starting material, 1-ethyl-3-[7-(2-methoxy-pyridin-4-yl)-imidazo[1,2-a]pyridin-2-yl]-urea was obtained. The crude product was purified by silica gel column chromatography (dichloromethane gradient to 2.5% of methanol in dichloromethane) to give the target compound. LCMS (APCI$^+$) 312.2 (100%, MH$^+$).

Example 45

Preparation of 1-Ethyl-3-[5-(3-methyl-[1,2,4]oxadiazol-5-yl)-7-pyridin-3-yl-imidazo[1,2-a]pyridin-2-yl]-urea

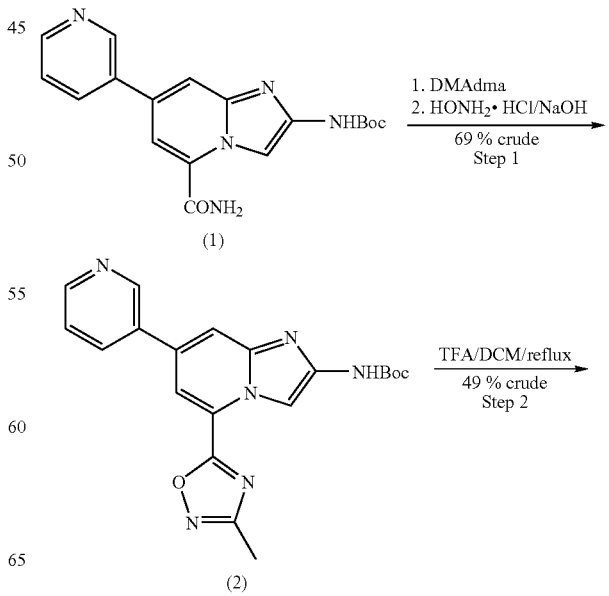

-continued

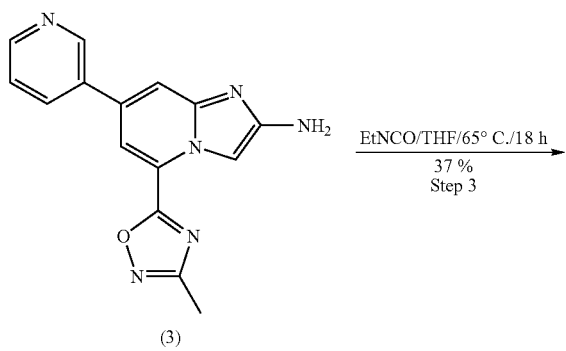

(3)

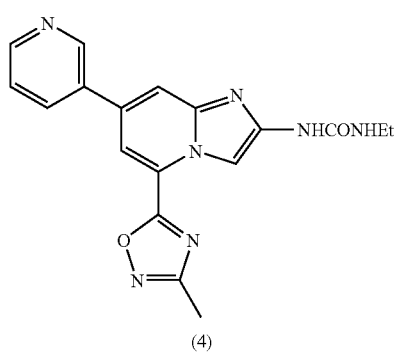

(4)

Step 1:

A solution of the amide (1) (0.30 g, 0.85 mmol) was dissolved in DMA (dimethylacetamide) (15 mL) and the solution was heated to 90° C., dimethylacetamide dimethylacetal (0.63 mL, 4.24 mmol) was added and the mixture was stirred for 2.5 h. Next the mixture was cooled to rt, diluted with water and extracted with ethyl acetate. Concentration yielded an oil, that was dissolved immediately in acetic acid (6 mL), hydroxylamine hydrochloride (87 mg, 1.27 mmol) and 1N NaOH (1.27 mL, 1.27 mmol). The solution was warmed at 90° C. for 30 min, then concentrated to dryness. The residue was slurried with water and filtered. The solid was washed with water and dried to give crude oxadiazole (2).

Step 2:

The crude product from step 1 (compound 2) (0.23 g, 0.59 mmol) was dissolved in trifluoroacetic acid (10 mL) and $CH_2Cl_2$ (10 mL) and the solution was refluxed for 1 h. Next the mixture was concentrated to dryness, then slurried with saturated aqueous $NaHCO_3$ and the mixture was chilled at 5° C. for 2 h before filtration to leave the crude amino compound (3) as a yellow solid.

Step 3:

A solution of the amino compound (3) (50 mg, 0.17 mmol) and ethyl isocyanate (50 µL, 0.72 mmol) in dry THF (10 mL) was warmed in a sealed tube at 60° C. for 18 h. The product was adsorbed directly onto silica by concentration and chromatographed. Elution with methanol/ethyl acetate (5:95) eluted the urea (4) which was triturated with diethyl ether to leave the final product as a tan powder (23 mg), FABMS Found: $[M+H]^+=364.1521$.

Example 46

Preparation of 1-Ethyl-3-[7-(6-fluoro-pyridin-3-yl)-imidazo[1,2-a]pyridin-2-yl]-urea

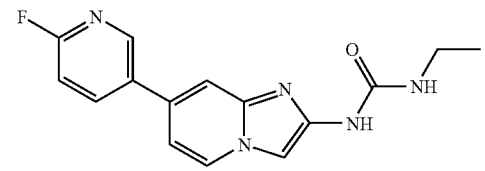

Using the generalized procedure of Example 8, but substituting 6-fluoro-3-pyridinylboronic acid as the relevant starting material, 1-ethyl-3-[7-(6-fluoro-pyridin-3-yl)-imidazo[1,2-a]pyridin-2-yl]-urea was obtained. The crude product was purified by silica gel column chromatography (dichloromethane gradient to 2% methanol in dichloromethane) to give the target compound (121 mg) as a solid LCMS ($APCI^+$) 300.2.

Example 47

Preparation of 1-Ethyl-3-[7-(1-methyl-6-oxo-1,6-dihydro-pyridin-3-yl)-imidazo[1,2-a]pyridin-2-yl]-urea

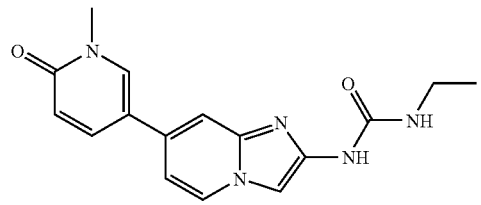

Using the generalized procedure of Example 37, but substituting 5-bromo-1-methyl-1H-pyridin-2-one as the relevant starting material, 1-ethyl-3-[7-(1-methyl-6-oxo-1,6-dihydro-pyridin-3-yl)-imidazo[1,2-a]pyridin-2-yl]-urea was obtained. The crude product was purified by silica gel column chromatography (dichloromethane gradient to 5% methanol in dichloromethane) to give the target compound (132 mg) as a solid. LCMS ($APCI^+$) 312.2.

Example 48

Preparation of 1-Ethyl-3-[7-(6-methyl-pyridin-3-yl)-imidazo[1,2-a]pyridin-2-yl]-urea

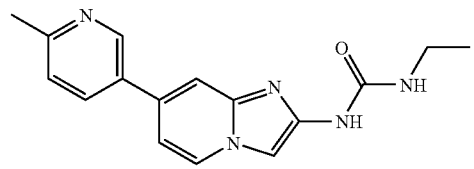

Using the generalized procedure of Example 8 but substituting 6-methyl-3-pyridinylboronic acid as the relevant starting material, 1-ethyl-3-[7-(6-methyl-pyridin-3-yl)-imidazo

[1,2-a]pyridin-2-yl]-urea was obtained. The crude product was purified by silica gel column chromatography (dichloromethane gradient to 4% methanol in dichloromethane) to give the target compound (114 mg) as a solid. LCMS (APCI⁺) 296.2.

Example 49

Preparation of 1-Ethyl-3-[7-(1-methyl-2-oxo-1,2-dihydro-pyridin-4-yl)-imidazo[1,2-a]pyridin-2-yl]-urea

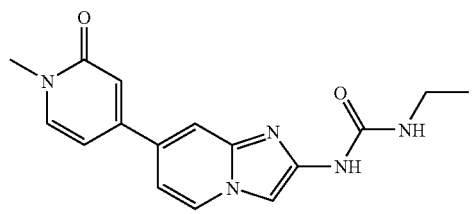

Using the generalized procedure of Example 37, but substituting 4-bromo-1-methyl-1H-pyridin-2-one as the relevant starting material, 1-ethyl-3-[7-(1-methyl-2-oxo-1,2-dihydro-pyridin-4-yl)-imidazo[1,2-a]pyridin-2-yl]-urea was obtained. The crude product was purified by silica gel column chromatography (dichloromethane gradient to 5% methanol in dichloromethane) to give the target compound (121 mg) as a solid. LCMS (APCI⁺) 312.2.

Example 50

Preparation of 7-(2-Dimethylamino-pyrimidin-5-yl)-2-(3-ethyl-ureido)-imidazo[1,2-a]pyridine-5-carboxylic Acid Ethylamide

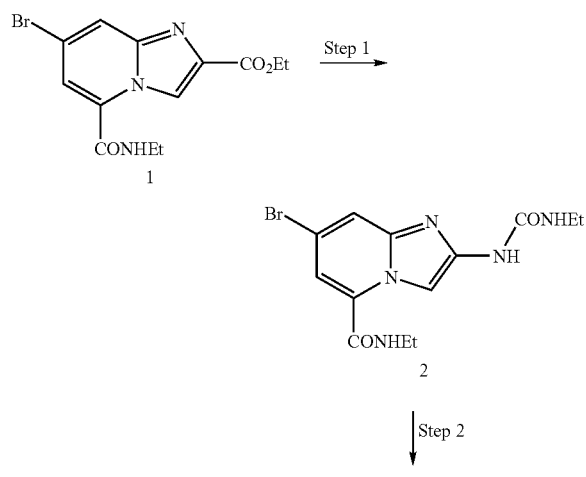

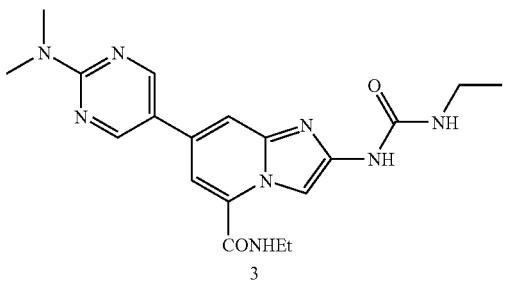

Step 1:

To a suspension of ester 1 (prepared as in Example 51) (1.70 g, 5.00 mmol) in 25 mL ethanol at 23° C. was added 2.5 mL anhydrous hydrazine. The reaction was stirred 24 h then the precipitated solid was collected by vacuum filtration and used without further purification. To a solution of this solid in 50 mL 5% aqueous sulfuric acid at 0° C. was added a solution of sodium nitrite (0.365 g, 5.28 mmol) in 5 mL water. The reaction was warmed to 23° C. and stirred 15 minutes, then it was carefully neutralized with solid sodium bicarbonate, and an additional 150 mL water. The resulting slurry was filtered and the collected solid was partitioned between water and dichloromethane and the organic layer was dried over sodium sulfate then evaporated in vacuo to give the acyl azide as a white fluffy solid. This material was suspended in 25 mL trifluoroethanol and was heated to reflux. The reaction became homogeneous upon reaching reflux temperature and a new precipitate gradually formed. After 2 h, the solvent was removed by evaporation in vacuo and the residue was dissolved in 15 mL dimethylsulfoxide and 15 mL 70% aqueous ethylamine and was heated to 80° C. for 30 minutes then 23° C. for 1 day. The reaction was poured onto water and the precipitate was collected by vacuum filtration, washed 3× water and dried under high vacuum to give 1.00 g (56%) of urea 2.

Step 2:

A suspension of aryl bromide 2 (0.151 g, 0.426 mmol), sodium acetate trihydrate (0.416 g, 2.81 mmol), 2-dimethylamino-pyrimidine-5-boronic acid (0.118 g, 0.711 mmol) in 1.5 mL water, 1.5 mL ethanol and 6 mL toluene was degassed then [1,1'-bis(diphenylphosphino)ferrocene]dichloropalladium II (17 mg, 0.023 mmol) was added and the reaction was heated to 105° C. After 3 h, the reaction was evaporated to dryness and suspended in 10% ethanol/dichloromethane, and filtered. The filtrate was extracted with 2×1N HCl and the combined aqueous layers were neutralized with solid sodium bicarbonate and extracted 3×10% ethanol/dichloromethane. The combined organic layers were dried over sodium sulfate and evaporated onto silica in vacuo. Chromatography (gradient elution: 5% to 60% isopropanol/dichloromethane) to give 3 as 0.037 g (22%) of yellow solid. MS (APCI)=[M+H] 397.1

Example 51

Preparation of 1-[7-(2-Dimethylamino-pyrimidin-5-yl)-5-pyrimidin-2-yl-imidazo[1,2-a]pyridin-2-yl]-3-ethyl-urea

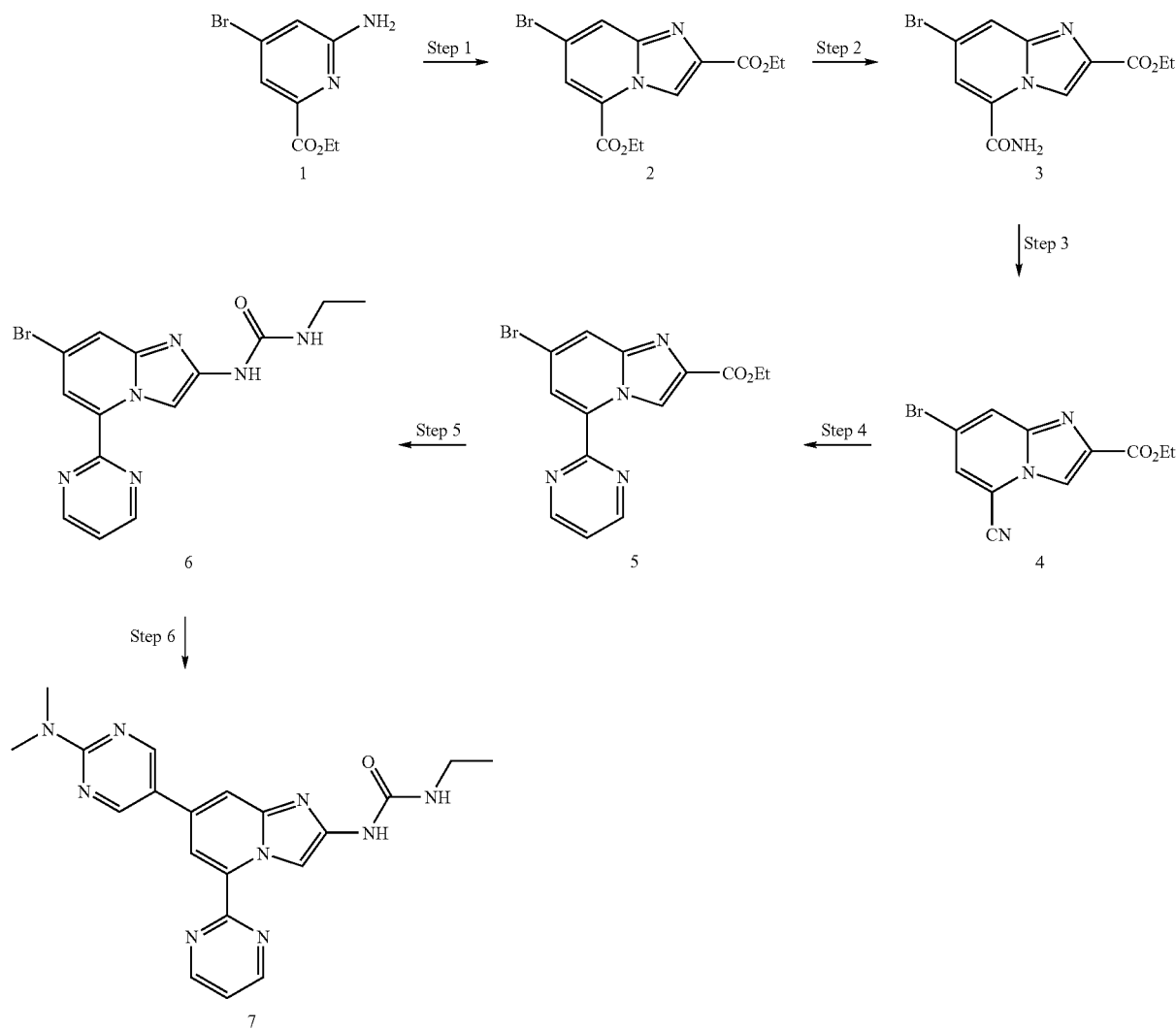

Step 1:
To a solution of aminopyridine 1 (20.9 g, 85.2 mmol) in 200 mL ethanol at 23° C. was added 12.5 mL ethyl bromopyruvate. The reaction was then heated to 80° C. After 3 h, the reaction was cooled to 23° C. and evaporated in vacuo. The residue was stirred in saturated aqueous sodium bicarbonate for 20 h and the suspended solid was collected by vacuum filtration and dried under high vacuum to give 2 as an off-white powder.

Step 2:
To a suspension of diester 2 (10.9 g, 31.9 mmol) in 50 mL ethanol was added 50 mL of 7M methanolic ammonia at 23° C. After 3 h, the copious precipitate was collected by vacuum filtration and dried under a stream of air to give 7.45 g (74%) of amide 3 as a white solid.

Step 3:
To a suspension of amide 3 (7.03 g, 22.5 mmol) in 150 mL tetrahydrofuran at 0° C. was added 10 mL pyridine followed by 5 mL trifluoroacetic anhydride dropwise. The reaction was allowed to warm to 23° C. and gradually became homogeneous. The reaction was then evaporated to ca. ⅓ its original volume then poured into iced 1N sodium bisulfate and extracted 3× dichloromethane. The combined organic layers were washed 2× saturated aqueous sodium bicarbonate, 1× brine and dried over sodium sulfate. Evaporation in vacuo gave nitrile 4 as a white fluffy solid.

Step 4:
A mixture of nitrile 4 (0.500 g, 1.7 mmol), 0.50 g trifluoroacetamide and 0.25 g dimethylaminoacrolein in 5 mL ethanol was heated to 125° C. for 2 h by microwave irradiation (CEM, 300 watt). The reaction was then evaporated in vacuo and the residue was purified by silica gel chromatography (gradient elution: 0-20% ethyl acetate/dichloromethane) to give pyrimidine 5.

Step 5:

To a stirring suspension of ester 5 (0.326 g, 0.939 mmol) in 5 mL ethanol was added 0.3 mL anhydrous hydrazine at 23° C. The reaction was then heated to 80° C. for 3 h then 60° C. for 15 h. The reaction was cooled to RT, diluted with hexane and the yellow ppt was collected by vacuum filtration. The filter cake was washed 2× diethyl ether and dried under a stream of air. The collected solid was then suspended in 5 mL 1N sodium bisulfate and 4N sulfuric acid was added dropwise just until the mixture became a solution. To this solution was then added sodium nitrate (0.065 g, 0.94 mmol) as a solution in 0.5 mL water dropwise and a copious ppt formed. The reaction was stirred 30 min then the solid was collected by vacuum filtration and washed 3× water, and dried under a stream of air. The solid was then suspended in 15 mL trifluoroethanol and heated to reflux for 2 h. The reaction was cooled to 23° C. and evaporated in vacuo. The residue was dissolved in 20 mL 2N ethylamine in tetrahydrofuran and heated to 80° C. After 24 h, 10 mL of 70% aqueous ethylamine were added and the reaction was heated an additional 24 h. It was then poured into water and the resulting precipitate was collected by vacuum filtration and dried under high vacuum to give 0.30 g (88%) of urea 6.

Step 6:

To a suspension of aryl bromide 6 (0.30 g 0.83 mmol), 0.22 g potassium fluoride (0.22 g, 3.7 mmol), and 2-dimethylamino-pyrimidine-5-boronic acid (0.21 g, 1.2 mmol) in 4 mL water, 6 mL isopropanol and 15 mL toluene was added 0.040 g bis[2-ethyl-1,3-oxazoline]palladium(II) acetate (0.040 g, 0.095 mmol) and the reaction was heated to reflux for 2 h. The reaction was then cooled to 23° C. and partitioned between dichloromethane and saturated aqueous sodium bicarbonate. The organic layer was then dried over sodium sulfate and evaporated in vacuo. The residue was purified by silica gel chromatography (gradient elution: 10-50% isopropanol/dichloromethane) to give 0.070 g (21%) of compound 7 as a yellow powder. LCMS (APCI)=[M+H] 404.2 (100%)

Example 52

The in-vitro antibacterial activity of selected compounds was determined against a stain of *Neisseria gonorrhoeae*, GC525 (NG-2888), which is described by Rouquette-Loughlin et al, in *Journal of Bacteriology*, February 2003, p. 1101-1106, at p. 1103. In general, minimum inhibitory concentration (MIC) susceptibility testing followed procedures recommended by the National Committee for Clinical Laboratory Standards (NCCLS[1-2]) or followed the descriptions described below:

Bacterial Cultures

*Neisseria gonorrhoeae* strains were grown on Chocolate Agar II plates (BBL—Becton Dickinson Microbiology Systems, Cockeysville, Md.) and incubated at 35° C. in a humidified 5% $CO_2$ incubator (Forma Scientific, Marietta Ohio). For microbroth dilution MIC testing, *N. gonorrhoeae* were tested in gonococcal broth (GCB):

Gonococcal Broth (GCB)[3]

| Proteose Peptone (BBL) | 15 g |
| Sodium Chloride | 5 g |
| Dipotassium Phosphate | 4 g |
| Potassium Dihydrogen Phosphate | 1 g |

-continued

| Soluble Starch (BBL) | 1 g |
| Sodium Bicarbonate | 420 mg |
| Distilled Water | 1000 mL |
| Isovitalex (BBL) | 10 mL |

Bacterial culture identifications were confirmed by standard microbiological methods.[4] *N. gonorrhoeae* strains were streaked onto appropriate agar plates for visualization of purity and expected colony morphology. Gram stains were also utilized.

Permanent Stock Culture Collection

Bacterial stock cultures are stored as frozen suspensions at −70° C. *N. gonorrhoeae* cultures are suspended in inactivated Horse Serum (Colorado Serum Company, Denver, Colo.) containing 7.5% glucose prior to snap freezing in a dry ice/ethanol bath.

Preparation of Standardized Test Inocula and Plate Inoculation

Frozen stock cultures were used as the initial source of organisms for performing microbroth dilution MIC testing. Stock cultures were passed on their respective growth medium at least one growth cycle (18-24 hours) prior to their use. Bacterial culture suspensions were prepared directly from Chocolate Agar II plates into 10 mL cation-adjusted Mueller-Hinton Broth (CAMHB, BBL, # BB215069). Before use, cultures were adjusted to an optical density value of 1.6-2 on a Perkin-Elmer Lambda EZ150 Spectrophotometer (Wellesley, Mass.) set at a wavelength of 600 nm. Random cultures were plated for validation of actual colony counts. The adjusted cultures were diluted 400-fold (0.25 mL inoculum+100 mL GCB) into gonococcal broth producing a starting inoculum of approximately $5\times10^5$ cfu/mL. These cultures were inoculated into test plates (100 uL/well) using a Biomek® FX workstation (Beckman Coulter Inc., Fullerton, Calif.). The inoculated plates were placed in stacks of no more than 4 and covered with an empty plate. Plates were incubated for 20-24 hours at 35° C. in a humidified $CO_2$ incubator.

Test Compound ("Drug") Preparation

Drug stock solutions (2 mg/mL in DMSO) were prepared on the day of testing. Drugs were weight corrected for assay content where necessary.

Drug Dilution Tray Preparation

Microbroth dilution stock plates were prepared in two dilution series, 64-0.06 ug drug/mL and 1-0.001 ug drug/mL. For the high concentration series, 200 uL of stock solution (2 mg/mL) was added to duplicate rows of a 96-well plate. This was used as the first well in the dilution series. Serial two-fold decremental dilutions were made using a BioMek FX robot (Beckman Coulter Inc., Fullerton, Calif.) with 10 of the remaining 11 wells, each of which contained 100 uL of the appropriate solvent/diluent. Row 12 contained solvent/diluent only and served as the control. For tube one of the low concentration series, 200 uL of a 31.25 ug/mL stock was added to duplicate rows of a 96-well plate. Serial two-fold dilutions were made as described above.

Daughter plates were spotted (3.2 uL/well) from the stock plates listed above using the BioMek FX robot and were inoculated with organism (100 uL/well) as described previously.

Reading the Test

After incubation, the degree of growth in each well was read visually with the aid of a Test Reading Mirror (Dynatech Lab 220-16, Dynex Technologies, Chantilly, Va.). 96-well test plates are read in a darkened room with a single light shining from above. The MIC is the lowest concentration of drug that prevents macroscopically visible growth under the conditions of the test. Each drug dilution series was tested in duplicate; identical results are not always obtained. If MIC values in duplicate tests differ by 1 well (two-fold), the lower value is reported. If duplicate tests vary by 2 dilutions (four-fold), the middle value is reported. Greater than a 4-fold MIC variance between duplicate tests invalidates the result and leads to a repeat of the organism/drug combination.

REFERENCES

[1] National Committee for Clinical Laboratory Standards. Performance Standards for Antimicrobial Susceptibility Testing; Fourteenth Informational Supplement. NCCLS document M100-S14 {ISBN 1-56238-516-X}, NCCLS, 940 West Valley Road, Suite 1400, Wayne, Pa. 19087-1898 USA, 2004.

[2] National Committee for Clinical Laboratory Standards. Methods for Dilution Antimicrobial Tests for Bacteria That Grow Aerobically; Approved Standard-Sixth Edition. NCCLS document M7-A6 {ISBN 1-56238-486-4}, NCCLS, 940 West Valley Road, Suite 1400, Wayne, Pa. 19087-1898 USA, 2003.

[3] Shapiro M A, Heifetz C L, Sesnie J C. Comparison of microdilution and agar dilution procedures for testing antibiotic susceptibility of *Neisseria gonorrhoeae*. J Clin Microbiol 1984; 20:828-30.

[4] Murray P R, Baron E J, Jorgensen J H, Pfaller M A, Yolken R H. Manual of Clinical Microbiology, Eighth Edition. ASM Press {ISBN 1-55581-255-4}, American Society for Microbiology, 1752 N Street NW, Washington, D.C. 20036-2904 USA, 2003.

Results:
The following were obtained:

| Example | MIC |
|---|---|
| 1A | >64.0 ug/mL |
| 1B | 16.0 ug/mL |
| 2A | >64.0 ug/mL |
| 2B | 16.0 ug/mL |
| 3A | >64.0 ug/mL |
| 3B | 16.0 ug/mL |
| 4 | 12.7 ug/mL |
| 5 | >64.0 ug/mL |
| 6 | 45.3 ug/mL |
| 7A | 5.66 ug/mL |
| 7B | 0.500 ug/mL |
| 8 | 5.66 ug/mL |
| 9 | >64.0 ug/mL |
| 10 | 8.00 ug/mL |
| 11 | 64.0 ug/mL |
| 12 | 64.0 ug/mL |
| 13 | >64 ug/mL |
| 14 | 64 ug/mL |
| 15 | 64 ug/mL |
| 16 | 64 ug/mL |
| 17 | >32 ug/mL |
| 18 | >64 ug/mL |
| 19 | >64 ug/mL |
| 20 | >64 ug/mL |
| 22 | >64 ug/mL |
| 23 | 0.13 ug/mL |
| 24 | >64 ug/mL |
| 25 | 64 ug/mL |
| 27 | 64 ug/mL |
| 28 | 32 ug/mL |
| 29 | 16 ug/mL |
| 30 | 32 ug/mL |
| 31 | 64 ug/mL |

-continued

| Example | MIC |
|---|---|
| 32 | >64 ug/mL |
| 33 | 16 ug/mL |
| 34 | 16 ug/mL |
| 35 | 64 ug/mL |
| 36 | 64 ug/mL |
| 37 | 64 ug/mL |
| 38 | 32 ug/mL |
| 39 | 16 ug/mL |
| 40 | >64 ug/mL |
| 41 | >64 ug/mL |
| 42 | 64 ug/mL |
| 43 | >64 ug/mL |
| 44 | 16 ug/mL |
| 45 | 0.25 ug/mL |
| 46 | 16 ug/mL |
| 50 | 2.0 ug/mL |
| 51 | 0.13 ug/mL |

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:
1. A compound of the formula

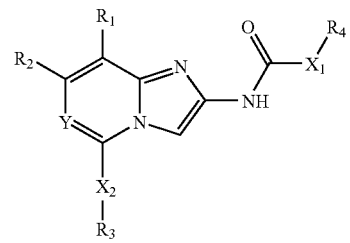

or a pharmaceutically acceptable salt thereof, wherein:
$X_1$ is $CH_2$, NH, or O;
$X_2$ is absent, or is
$(CH_2)_{x'}$, NH, O, or

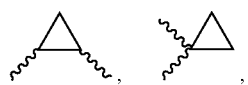

wherein "$\sim\sim\sim$" are points of attachment, or is a tether 2, 3 or 4 atoms in length, selected from

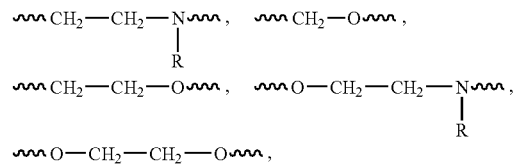

-continued

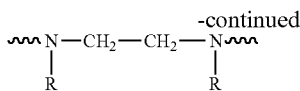

wherein R is H or (C₁-C₆)alkyl, and
wherein """""" are points of attachment and x' is an integer from 1 to 3;

Y is C—H, C—F, or C—OMe;
R₁ is H or halo;
R₂ is (C₃-C₆)cycloalkyl,
(CH₂)ₓ-aryl,
(CH₂)ₓ-heterocyclyl, or
(CH₂)ₓ-heteroaryl,
wherein x is 0, 1, or 2;
R₃ is H,
(C₁-C₆)alkyl,
(C₃-C₆)cycloalkyl,
aryl,
heterocyclyl,
heteroaryl,
C(O)NRₐRᵦ,
C(O)Rₐ,
CO₂Rₐ,
C(O)C(O)NRₐRᵦ,
NO₂,
SO₂Rₐ,
SO₂NRₐRᵦ,
C(Rc)=NORₐ,
C(Rc)=NRₐ,

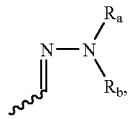

wherein """""" indicates the point of attachment,

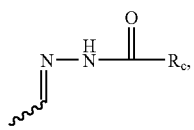

wherein """""" indicates the point of attachment,
and wherein
Rₐ is H,
(C₁-C₆)alkyl,
(C₃-C₆)cycloalkyl,
(CH₂)ᵧ-aryl,
(CH₂)ᵧ-heterocycyl, or
(CH₂)ᵧ-heteroaryl,
wherein y is 0, 1, or 2;
Rᵦ is H,
(C₁-C₆)alkyl,
(C₃-C₆)cycloalkyl,
aryl,
heterocyclyl, or
heteroaryl;
Rc is H,
(C₁-C₆)alkyl,
(C₃-C₆)cycloalkyl,
aryl,
heterocyclyl, or
heteroaryl; and R₄ is (C₁-C₆)alkyl, (C₁-C₆alkyl)-O—(C₁-C₆alkyl), cyclopropyl, CH₂-cyclopropyl, or cyclobutyl.

2. A compound according to claim 1 in which Y is C—H or a pharmaceutically acceptable salt thereof.

3. A compound according to claim 1 in which X₁ is NH, X₂ is absent, or is (CH₂)ₓ', NH, or O;
R₁ is H;
R₂ is
(CH₂)ₓ-heteroaryl,
wherein x is 0, 1, or 2;
R₃ is
H,
aryl,
heterocyclyl,
heteroaryl,
C(O)NRₐRᵦ,
C(O)Rₐ, or
CO₂Rₐ,
and,
R₄ is (C₁-C₆)alkyl, cyclopropyl, CH₂-cyclopropyl or cyclobutyl, or a pharmaceutically acceptable salt thereof.

4. A compound according to claim 1 in which R₂ is heteroaryl or a pharmaceutically acceptable salt thereof.

5. A compound according to claim 1 in which R₂ is heteroaryl and is selected from the group consisting of pyridine, and pyrimidine, either of which may be optionally substituted, or a pharmaceutically acceptable salt thereof.

6. A compound according to claim 1 in which X₂ is absent and R₃ is hydrogen, heteroaryl, C(O)NRₐRᵦ, C(O)Rₐ, or CO₂Rₐ, or a pharmaceutically acceptable salt thereof.

7. A compound according to claim 1 in which R₄ is ethyl or cyclobutyl, or a pharmaceutically acceptable salt thereof.

8. A compound selected from the group consisting of:
(7-pyridin-3-yl-imidazo[1,2-a]pyridin-2-yl)-carbamic acid ethyl ester;
1-ethyl-3-(7-pyridin-3-yl-imidazo[1,2-a]pyridin-2-yl)-urea;
[7-(2-dimethylamino-pyrimidin-5-yl)-imidazo[1,2-a]pyridin-2-yl]-carbamic acid ethyl ester;
1-[7-(2-dimethylamino-pyrimidin-5-yl)-imidazo[1,2-a]pyridin-2-yl]-3-ethyl-urea;
[7-(6-methoxy-pyridin-3-yl)-imidazo[1,2-a]pyridin-2-yl]-carbamic acid ethyl ester;
1-ethyl-3-[7-(6-methoxy-pyridin-3-yl)-imidazo[1,2-a]pyridin-2-yl]-urea;
1-ethyl-3-[7-(2-methoxy-pyrimidin-5-yl)-imidazo[1,2-a]pyridin-2-yl]-urea;
1-ethyl-3-{7-[6-(2-morpholin-4-yl-ethoxy)-pyridin-3-yl]-imidazo[1,2-a]pyridin-2-yl}-urea;
1-ethyl-3-(5-hydroxymethyl-7-pyridin-3-yl-imidazo[1,2-a]pyridin-2-yl)-urea;
1-ethyl-3-(5-formyl-7-pyridin-3-yl-imidazo[1,2-a]pyridin-2-yl)-urea;
2-(3-ethyl-ureido)-7-pyridin-3-yl-imidazo[1,2-a]pyridine-5-carboxylic acid methyl ester;
1-ethyl-3-(7-pyrimidin-5-yl-imidazo[1,2-a]pyridin-2-yl)-urea;
1-[7-(3,5-dimethyl-isoxazol-4-yl)-imidazo[1,2-a]pyridin-2-yl]-3-ethyl-urea;
1-[7-(1-benzyl-1H-pyrazol-4-yl)-imidazo[1,2-a]pyridin-2-yl]-3-ethyl-urea;
1-ethyl-3-{7-[6-(4-methyl-piperazin-1-yl)-pyridin-3-yl]-imidazo[1,2-a]pyridin-2-yl}-urea;
1-ethyl-3-[7-(1-methyl-1H-pyrazol-4-yl)-imidazo[1,2-a]pyridin-2-yl]-urea;
1-[7-(2,4-dimethoxy-pyrimidin-5-yl)-imidazo[1,2-a]pyridin-2-yl]-3-ethyl-urea;
4-[2-(3-ethyl-ureido)-imidazo[1,2-a]pyridin-7-yl]-3,5-dimethyl-pyrazole-1-carboxylic acid tert-butyl ester;

1-ethyl-3-[7-(1H-pyrazol-4-yl)-imidazo[1,2-a]pyridin-2-yl]-urea;
1-(3-chloro-7-pyridin-3-yl-imidazo[1,2-a]pyridin-2-yl)-3-ethyl-urea;
1-[3-chloro-7-(2-dimethylamino-pyrimidin-5-yl)-imidazo[1,2-a]pyridin-2-yl]-3-ethyl-urea;
2-(3-ethyl-ureido)-imidazo[1,2-a]pyridine-7-carboxylic acid methyl ester;
2-(3-ethyl-ureido)-imidazo[1,2-a]pyridine-7-carboxylic acid amide;
1-ethyl-3-[7-(5-methyl-2H-[1,2,4]triazol-3-yl)-Imidazo[1,2-a]pyridin-2-yl]-urea;
1-[7-(1,5-dimethyl-1H-[1,2,4]triazol-3-yl)-imidazo[1,2-a]pyridin-2-yl]-3-ethyl-urea;
1-[7-(2,5-dimethyl-2H-[1,2,4]triazol-3-yl)-imidazo[1,2-a]pyridin-2-yl]-3-ethyl-urea;
1-ethyl-3-[7-(5-methyl-[1,2,4]oxadiazol-3-yl)-imidazo[1,2-a]pyridin-2-yl]-urea;
1-ethyl-3-[5-(1-methyl-1H-pyrazol-4-yl)-7-pyridin-3-yl-imidazo[1,2-a]pyridin-2-yl]-urea;
2-(3-ethyl-ureido)-imidazo[1,2-a]pyridine-7-carboxylic acid;
1-[7-(3,5-dimethyl-1H-pyrazol-4-yl)-imidazo[1,2-a]pyridin-2-yl]-3-ethyl-urea;
1-ethyl-3-[7-(piperidine-1-carbonyl)-imidazo[1,2-a]pyridin-2-yl]-urea;
1-cyclopropyl-3-(7-pyrimidin-5-yl-imidazo[1,2-a]pyridin-2-yl)-urea;
1-cyclopropylmethyl-3-(7-pyrimidin-5-yl-imidazo[1,2-a]pyridin-2-yl)-urea;
1-propyl-3-(7-pyrimidin-5-yl-imidazo[1,2-a]pyridin-2-yl)-urea;
1-isopropyl-3-(7-pyrimidin-5-yl-imidazo[1,2-a]pyridin-2-yl)-urea;
1-(7-pyrimidin-5-yl-imidazo[1,2-a]pyridin-2-yl)-3-(2,2,2-trifluoro-ethyl)-urea;
1-(2-methoxy-ethyl)-3-(7-pyrimidin-5-yl-imidazo[1,2-a]pyridin-2-yl)-urea;
1-cyclobutyl-3-(7-pyrimidin-5-yl-imidazo[1,2-a]pyridin-2-yl)-urea;
1-[7-(6-amino-pyridin-3-yl)-imidazo[1,2-a]pyridin-2-yl]-3-ethyl-urea;
N-(7-acetylimidazo[1,2-a]pyridin-2-yl)-N'-ethylurea;
1-ethyl-3-[7-(5-methyl-[1,3,4]oxadiazol-2-yl)-imidazo[1,2-a]pyridin-2-yl]-urea;
{4-[2-(3-ethyl-ureido)-imidazo[1,2-a]pyridin-7-yl]-pyridin-2-yl}-carbamic acid tert-butyl ester;
1-ethyl-3-[7-(2H-pyrazol-3-yl)-imidazo[1,2-a]pyridin-2-yl]-urea;
1-ethyl-3-(7-[1,2,3]thiadiazol-4-yl-imidazo[1,2-a]pyridin-2-yl)-urea;
1-ethyl-3-[7-(5-isopropyl-[1,2,4]oxadiazol-3-yl)-imidazo[1,2-a]pyridin-2-yl]-urea;
1-ethyl-3-[7-(5-oxo-4,5-dihydro-[1,2,4]oxadiazol-3-yl)-imidazo[1,2-a]pyridin-2-yl]-urea;
{4-[2-(3-ethyl-ureido)-imidazo[1,2-a]pyridin-7-yl]-pyridin-2-yl}-carbamic acid tert-butyl ester;
1-[7-(2-amino-pyridin-4-yl)-imidazo[1,2-a]pyridin-2-yl]-3-ethyl-urea;
1-ethyl-3-[7-morpholinyl-4-carbonyl)-imidazo[1,2-a]pyridin-2-yl]-urea;
1-ethyl-3-[7-(2-methoxy-pyridin-4-yl)-imidazo[1,2-a]pyridin-2-yl]-urea;
1-ethyl-3-[5-(3-methyl-[1,2,4]oxadiazol-5-yl)-7-pyridin-3-yl-imidazo[1,2-a]pyridin-2-yl]-urea;
1-ethyl-3-[7-(6-fluoro-pyridin-3-yl)-imidazo[1,2-a]pyridin-2-yl]-urea;
1-ethyl-3-[7-(1-methyl-6-oxo-1,6-dihydro-pyridin-3-yl)-imidazo[1,2-a]pyridin-2-yl]-urea;
1-ethyl-3-[7-(6-methyl-pyridin-3-yl)-imidazo[1,2-a]pyridin-2-yl]-urea;
1-ethyl-3-[7-(1-methyl-2-oxo-1,2-dihydro-pyridin-4-yl)-imidazo[1,2-a]pyridin-2-yl]-urea;
7-(2-dimethylamino-pyrimidin-5-yl)-2-(3-ethyl-ureido)-imidazo[1,2-a]pyridine-5-carboxylic acid ethylamide, and
1-[7-(2-dimethylamino-pyrimidin-5-yl)-5-pyrimidin-2-yl-imidazo[1,2-a]pyridin-2-yl]-3-ethyl-urea, or
a pharmaceutically acceptable salt thereof.

9. A compound selected from the group consisting of:
1-ethyl-3-(7-pyridin-3-yl-imidazo[1,2-a]pyridin-2-yl)-urea;
1-ethyl-3-[7-(6-methoxy-pyridin-3-yl)-imidazo[1,2-a]pyridin-2-yl]-urea;
1-ethyl-3-[7-(2-methoxy-pyrimidin-5-yl)-imidazo[1,2-a]pyridin-2-yl]-urea;
1-ethyl-3-(5-hydroxymethyl-7-pyridin-3-yl-imidazo[1,2-a]pyridin-2-yl)-urea;
1-ethyl-3-(5-formyl-7-pyridin-3-yl-imidazo[1,2-a]pyridin-2-yl)-urea;
2-(3-ethyl-ureido)-7-pyridin-3-yl-imidazo[1,2-a]pyridine-5-carboxylic acid methyl ester;
1-ethyl-3-(7-pyrimidin-5-yl-imidazo[1,2-a]pyridin-2-yl)-urea;
1-ethyl-3-[5-(1-methyl-1H-pyrazol-4-yl)-7-pyridin-3-yl-imidazo[1,2-a]pyridin-2-yl]-urea;
1-propyl-3-(7-pyrimidin-5-yl-imidazo[1,2-a]pyridin-2-yl)-urea;
1-cyclobutyl-3-(7-pyrimidin-5-yl-imidazo[1,2-a]pyridin-2-yl)-urea;
1-[7-(6-amino-pyridin-3-yl)-imidazo[1,2-a]pyridin-2-yl]-3-ethyl-urea
1-ethyl-3-[7-(2H-pyrazol-3-yl)-imidazo[1,2-a]pyridin-2-yl]-urea;
1-ethyl-3-(7-[1,2,3]thiadiazol-4-yl-imidazo[1,2-a]pyridin-2-yl)-urea;
1-ethyl-3-[7-(2-methoxy-pyridin-4-yl)-imidazo[1,2a]pyridin-2-yl]-urea;
1-ethyl-3-[5-(3-methyl-[1,2,4]oxadiazol-5-yl)-7-pyridin-3-yl-imidazo[1,2-a]pyridin-2-yl]-urea;
1-ethyl-3-[7-(6-fluoro-pyridin-3-yl)-imidazo[1,2-a]pyridin-2-yl]-urea;
7-(2-dimethylamino-pyrimidin-5-yl)-2-(3-ethyl-ureido)-imidazo[1,2-a]pyridine-5-carboxylic acid ethylamide, and;
1-[7-(2-dimethylamino-pyrimidin-5-yl)-5-pyrimidin-2-yl-imidazo[1,2-a]pyridin-2-yl]-3-ethyl-urea, or
a pharmaceutically acceptable salt thereof.

10. A pharmaceutical formulation comprising a compound according to claim 1 admixed with a pharmaceutically acceptable diluent, carrier, or excipient.

* * * * *

UNITED STATES PATENT AND TRADEMARK OFFICE
CERTIFICATE OF CORRECTION

PATENT NO. : 7,563,788 B2  Page 1 of 1
APPLICATION NO. : 10/598841
DATED : July 21, 2009
INVENTOR(S) : Sciotti et al.

It is certified that error appears in the above-identified patent and that said Letters Patent is hereby corrected as shown below:

On the Title page, please correct Item (73) to read as follows:

(73) Assignee: Warner-Lambert Company LLC, Morris Plains, NJ (US)

Signed and Sealed this
Twenty-ninth Day of January, 2013

David J. Kappos
*Director of the United States Patent and Trademark Office*